United States Patent [19]

Snook et al.

[11] Patent Number: 4,932,402
[45] Date of Patent: Jun. 12, 1990

[54] INSPIRATION OXYGEN SAVER

[75] Inventors: James A. Snook, Overland Park; Thomas W. Nelson, Lenexa; Marilyn S. Wyble; Russell L. Trimble, both of Overland Park, all of Kans.

[73] Assignee: Puritan-Bennett Corporation, Lenexa, Kans.

[21] Appl. No.: 108,948

[22] Filed: Oct. 16, 1987

Related U.S. Application Data

[62] Division of Ser. No. 851,132, Apr. 11, 1986.

[51] Int. Cl.$^5$ .................... A61M 16/00; A61B 7/00
[52] U.S. Cl. .................... 128/204.23; 128/204.26; 364/413.03
[58] Field of Search ............ 128/204.23, 205.11, 128/204.26, 205.14; 364/413.01, 413.02, 413.03, 413.3

[56] References Cited

U.S. PATENT DOCUMENTS

| 4,336,590 | 6/1982 | Jacq et al. | 364/413.3 |
| 4,648,395 | 3/1987 | Sato et al. | 128/204.23 |
| 4,665,911 | 5/1987 | Williams | 128/204.23 |
| 4,681,099 | 7/1987 | Sato et al. | 128/204.23 |

Primary Examiner—Francis Jaworski
Assistant Examiner—George Manuel
Attorney, Agent, or Firm—Hovey, Williams, Timmons & Collins

[57] ABSTRACT

A reliable, pulse-flow supplemental oxygen apparatus for alleviating respiratory ailments is provided which yields substantial savings in oxygen while giving the patient the physiological equivalent of a prescribed continuous stream of oxygen. The apparatus preferably includes a demand oxygen valve operated in a pulse mode by means of electronic control circuitry which, through an appropriate sensor, monitors the patient's breathing efforts and gives a variable "custom tailored" pulse volume of oxygen to the patient during the very initial stages of each inspiration. Pulse volume variability is based upon a measured parameter characterizing at least a part of one and preferably a plurality of the patient's preceding breaths; advantageously, the elapsed time interval of the patient's three preceding breath cycles is measured to effectively measure breath rate. These breath-characterizing parameters, together with data characterizing the prescribed continuous oxygen flow to be matched, enable the apparatus to give the desired "on the go" dose variability. The apparatus is also designed to revert to conventional, continuous-flow operation upon a power failure or circuit malfunction, and for this purpose a specialized dual flow control restrictor valve is provided in the form of the invention designed for hospital use. In the event of abnormally low or high breath rates on the part of the patient, the device automatically delivers a relatively long continuous pulse, then stops to again sample the breath rate. If the rate is normal, the usual pulse flow operation is resumed; if the rate remains abnormal, the long pulse volume-rate sampling is repeated. Actual tests with the apparatus hereof demonstrate an oxygen saving of over 50% as compared with continuous flow regimens.

11 Claims, 11 Drawing Sheets

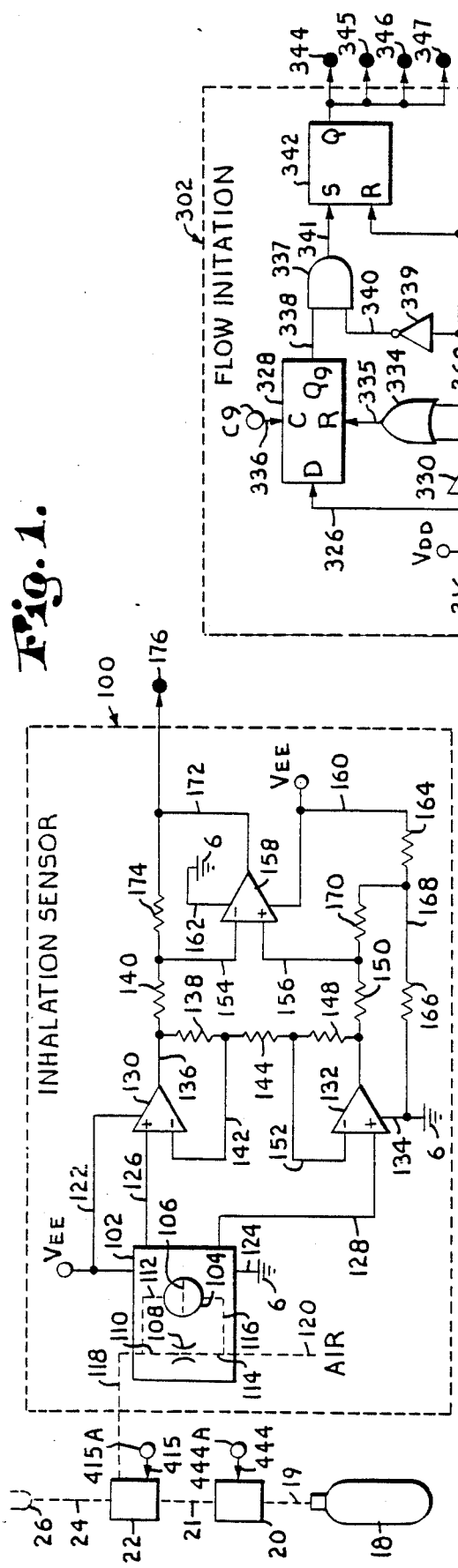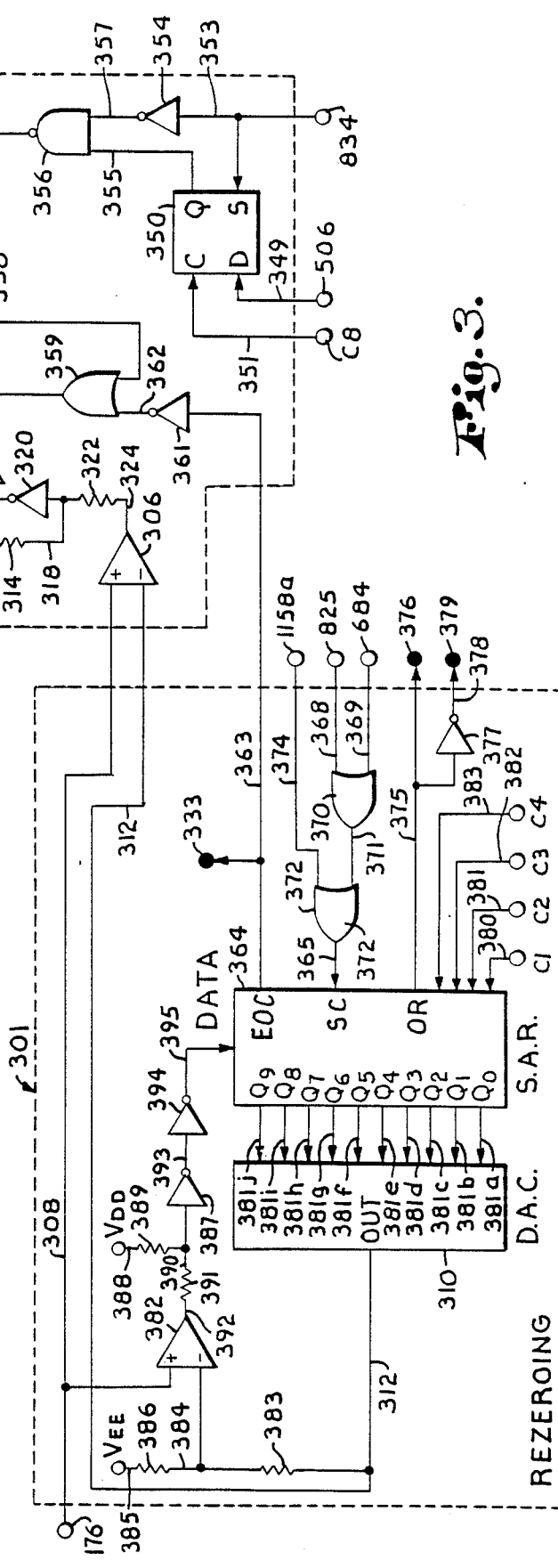
Fig. 1.
Fig. 3.

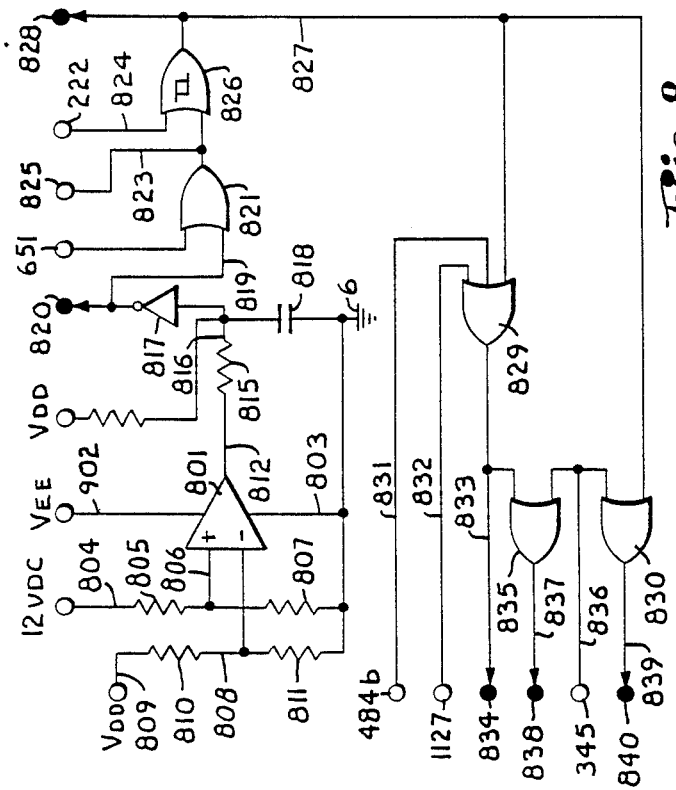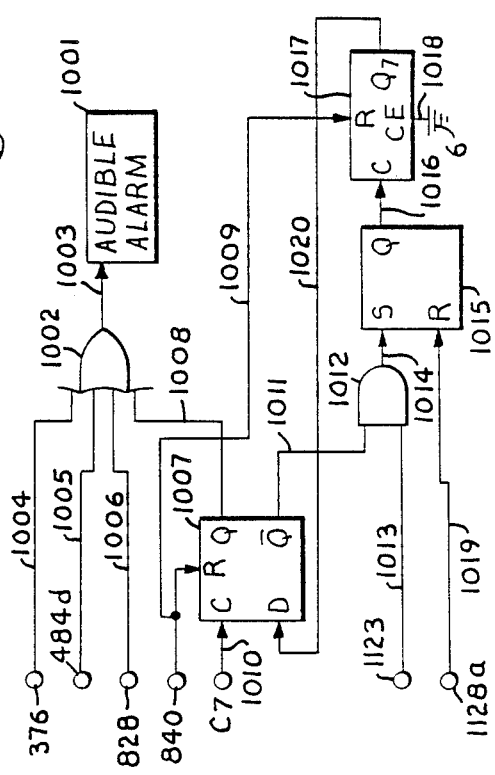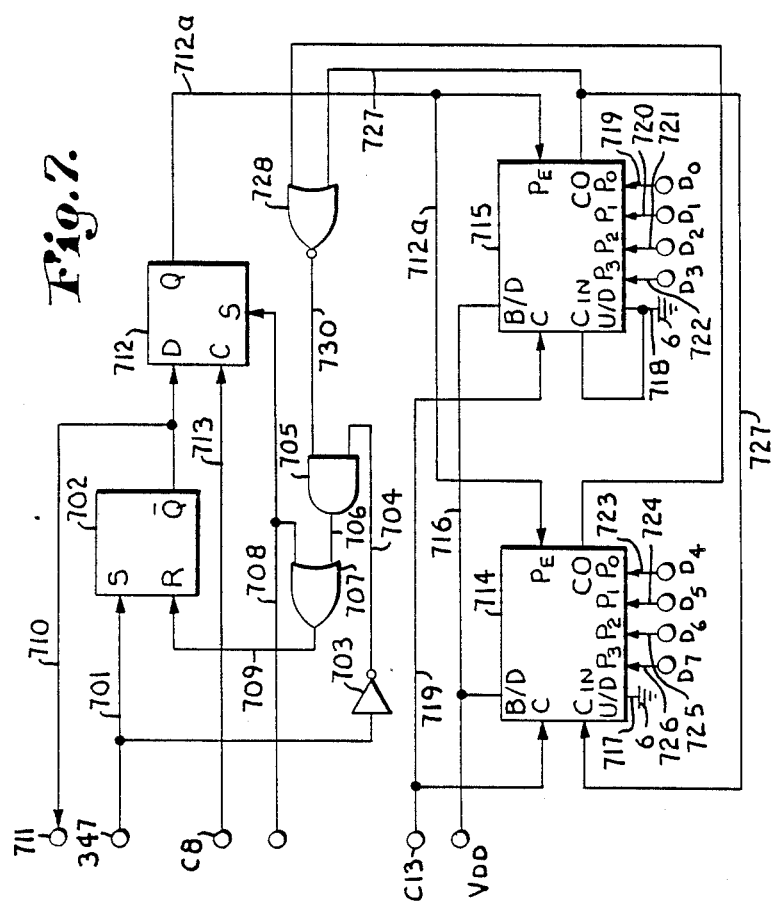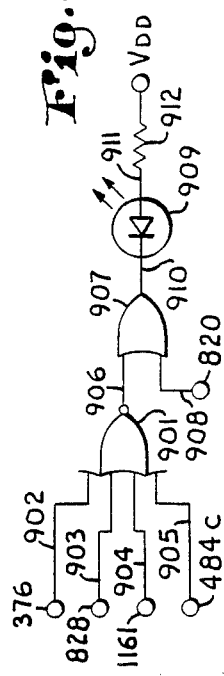
Fig. 8.
Fig. 10.
Fig. 7.
Fig. 9.

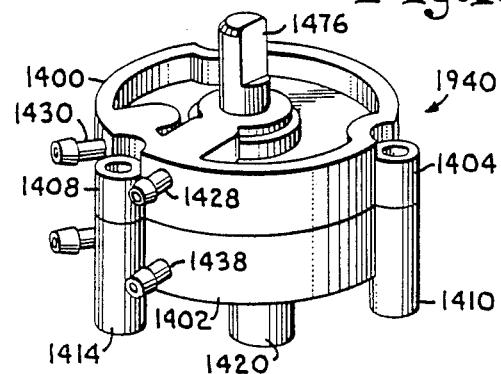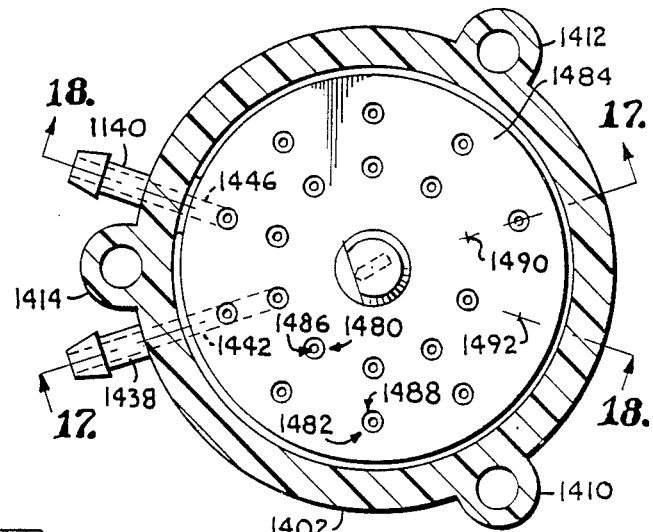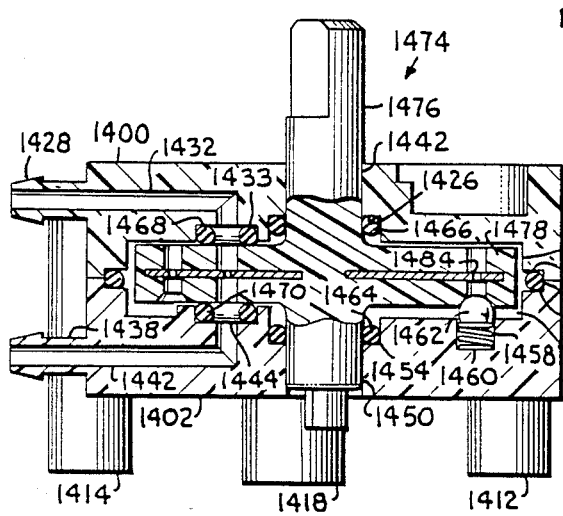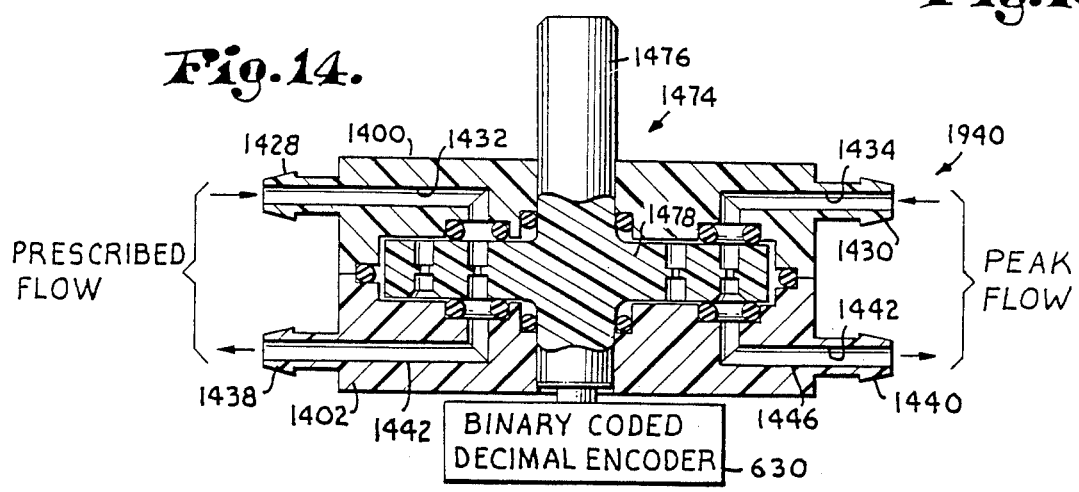

INSPIRATION OXYGEN SAVER

This is a division of application Ser. No. 06/851,132, filed on Apr. 11, 1986.

BACKGROUND OF THE INVENTION

1. Field of the Invention

The present invention is concerned with supplemental medicinal gas delivering devices designed to supply to a patient effective amounts of medicinal gases such as oxygen. Devices of this character are commonly used in the treatment of various lung ailments, for example, emphysema. More particularly, the invention is concerned with a greatly improved gas therapy apparatus which is designed to save substantial quantities of medicinal gas, as compared with the conventional and time-honored approach of simply supplying a continuous stream of such gas to the patient. This savings is accomplished by controlling the length as well as the timing of the periods during which oxygen is supplied to the patient in a unique manner in response to the timing of the patient's own breathing efforts. Moreover, the invention comprehends a unique flow control valve designed for use in such gas therapy applications, together with electronic circuitry to provide precise, reliable control under normal and extraordinary conditions encountered in the treatment of patients.

2. Description of the Prior Art

Many patients suffering from diseases of the respiratory system are treated through the use of supplemental oxygen or other gas. Very commonly, and particularly in the case of supplemental oxygen, the administration technique has involved nothing more than applying a continuous stream of oxygen to the patient through a nose cannula or similar device. Thus, a physician may prescribe a given flow rate of oxygen for a patient, and a simple control valve is set to deliver the prescribed flow rate.

While this approach does provide the patient with supplemental oxygen, it is extremely wasteful from the standpoint of oxygen usage. That is to say, physiological studies have demonstrated that much of the oxygen delivered to a patient during a breathing cycle is wasted; it may simply be directly exhaled or never reach the lungs. In fact, prior studies have established that the physiological equivalent of continuous oxygen delivery can be achieved by administering relatively short, high flow rate pulse volumes of oxygen at the beginning of the inspiration cycle, and that if properly done such a therapy is just as effective as continuous administration of relatively lower flow rates of gas.

Apart from the gas waste inherent in continuous systems, it is also generally necessary to humidify a gas which is being continuously delivered to a patient. This may be accomplished by bubbling the gas through a humidifier prior to delivery to the cannula. While such humidifiers are well known, they present a problem inasmuch as the moist environment of the humidifier can be a significant vector for the transmission of infection. This problem can be especially acute in the case of weak or non-ambulatory patients, as will be readily appreciated.

U.S. Pat. No. 4,457,303 to Durkan describes a respirator apparatus designed for intermittent demand oxygen flow and apneic event detection. The structure described in this patent provides a selectively settable device which, at an appropriate time during a patient's breathing cycle, will deliver a predetermined quantity of gas in the form of a fixed time duration pulse. A prime deficiency of this approach, however, is the fact that the device cannot automatically adjust the pulse volume delivered over time to accommodate different patient breathing rates and conditions. Thus, the Durkan apparatus is preset to deliver a constant, predetermined pulse volume, and does so notwithstanding variations in demand on the part of the patient or other external factors Thus, if the patient begins to breathe rapidly, the effective result may be a near-continuous flow of gas, whereas if the patient breathes more slowly only relatively small, widely spaced doses are delivered. In short, the Durkan device provides no "on-the-go" operational flexibility, but rather supplies a constant dose of oxygen under all conditions once set.

SUMMARY OF THE INVENTION

The present invention provides a greatly improved device for supplying supplemental doses of medicinal gases in a manner to obtain equal (or more favorable) physiological results, as compared with the prior technique of continuous gas administration. A prime feature of the invention stems from the fact that the volume of gas delivered in each individual pulse is varied depending upon the patient's ongoing breathing rate. As such, the invention provides "custom-tailored" supplemental gas pulse volumes which are specifically and continuously adJusted to match the breathing rate of the patient and the physician prescribed dose. In addition, clinically this invention delivers a preprogrammed volume of gas per unit of time depending upon the physician-selected prescription. This volume may advantageously be constant or could be programmed to vary in a nonlinear fashion depending upon medical need.

In more detail, the apparatus of the invention is adapted for connection between a source of medicinal gas (e.g., pressurized oxygen) and a patient-coupled gas delivery device such as a nasal cannula or like expedient. The apparatus is designed for supplying pulse volumes of the gas to the patient from time to time during the patient'breathing cycles, and, in the case of oxygen, at the very beginning of inspiration during each breathing cycle. In general, the apparatus includes selectively actuatable valve means which may be a valve, flow proportioner, or the like adapted for coupling between the gas source and the delivery device for selectively establishing and interrupting gas flow communication therebetween. In addition, electronically controlled actuating means is provided for selectively operating the valve means, and includes breathing cycle sensing means and electronic means operably coupled with the sensing means for measuring a parameter characteristic of at least one of the patient's breathing cycles, and for providing a value correlated with the measured time interval. Finally, means is connected between the measuring means and the valve means for actuating the latter: in order to establish the gas flow communication for a period of time which varies in response to the assigned parameter value.

In preferred forms of the invention, the sensing means is in the form of an extremely sensitive pressure or flow sensing device or the like operatively coupled through the valve and gas delivery device to the patient's breathing passages. Other types of breathing cycle sensing means could also be used, e.g., those measuring breath flow rate, breath flow direction, breath temperature, breath humidity, breath oxygen content, breath carbon dioxide content or breath sounds; the goal in each case, of course, is to sense a parameter characterizing the breathing cycle. The preferred measuring apparatus includes structure for measuring a time interval which characterizes at least a part of one of the patient's breathing cycles (e.g., the duration of inhalation). This time interval is advantageously the duration of a plurality of breathing cycles including both inhalation and exhalation. The connecting means between the time measurement apparatus and valve means comprises control circuitry designed to receive input data from the measuring apparatus, to provide a value correlated therewith, and to correspondingly generate an output signal in response to such input data which controls the valve actuation timing. Thus, in preferred forms, the period of time during which the valve means is open, and hence gas is being delivered, varies in relation to the input signal values received.

In one particular embodiment of the invention designed for hospital or institutional use, a demand valve of the type described above is employed. In addition, however, a secondary dual flow control arrangement in series with the demand valve is also provided which, in the normal pulsemode position of the overall apparatus, delivers a relatively high flow rate of gas to the downstream demand valve which in turn is operated in the desired pulse mode. However, during abnormal or upset conditions, the series flow control device delivers a continuous flow of gas at a lower predetermined prescribed flow rate. This dual flow rate device thus permits the unit to be set to the physician's prescribed flow rate, and thereby achieve substantially the physiological equivalent of such prescribed flow rate in both the pulse mode and the continuous flow mode.

In another embodiment of the invention principally designed for home use, the dual flow control device is eliminated. In this case, physiologically equivalent pulse volumes are assured by virtue of the fact that, during the relatively long time that the demand valve is closed during each breathing cycle, excess gas builds up in the equipment between the valve and gas source (e.g., a dynamic pressure regulator). As a consequence, when the valve is again opened to deliver a pulse of gas, the excess pressure is quickly released to give a desired, high peak rate pulse of gas to the patient.

The pulse volume supply apparatus of the invention is also equipped with numerous safety features assuring that, in the event of a malfunction or abnormal breathing efforts on the part of the patient, the unit is switched to a continuous mode at the prescribed flow rate. Hence, one such feature involves provision of means for sensing the breath rate of the patient. If this breath rate is above or below preselected limits, the device is shifted to the continuous flow mode for a substantial period of time greatly in excess of a usual peak pulse time (e.g., 7.5 seconds). At the end of this continuous flow time period, the unit then reverts to the pulse flow mode for at least a minimum period of time, until another abnormal breathing condition is detected. In like manner, in the event of a power outage to the unit or circuit failure, the device is automatically shifted to the continuous flow mode. To this end, the demand valve employed is preferably a three-way solenoid valve mechanically biased to the continuous flow condition thereof. Thus, upon power outage, the valve simply shifts to the continuous flow orientation thereof.

The gas pulses generated by the apparatus of the invention are designed for delivery to the patient at the very early stages of inspiration during each breathing cycle. In practice, pulse flow is initiated within about 15 to 60 milliseconds after the patient begins to inspire. As a consequence of this operational characteristic, an extremely sensitive inhalation sensor is employed. By virtue of this extreme sensitivity, the sensor device itself is subject to ambient-induced signal drift, which, if uncorrected over time, could lead to inaccuracies in pulse volume delivery. However, the present invention overcomes this potential problem by provision of automatic rezeroing circuitry which, at the end of 30 each delivered gas pulse when the inhalation sensor is pneumatically isolated from the gas delivery device, electronically puts into memory an appropriate inhalation sensor rezeroing signal to be used as a reference during the next breathing cycle. In this way, the system is continuously rezeroed so as to compensate for any ambient-induced drift in the sensor.

BRIEF DESCRIPTION OF THE DRAWINGS

FIG. 1 is a schematic representation of the preferred arrangement of pneumatic components and electronic circuitry of the inhalation sensor portion of the overall controller device of the invention, with significant pneumatic components of the "hospital" embodiment of the invention also being illustrated;

FIG. 3 is an electrical schematic drawing illustrating the preferred flow initiation and rezeroing circuitry of the overall device;

FIG. 7 is an electrical schematic drawing illustrating the circuitry associated with the blanking function of the complete controller device;

FIG. 8 is an electrical schematic drawing depicting the preferred reset and power monitoring circuitry of the device;

FIG. 9 is an electrical schematic drawing showing the preferred failure indicator circuitry of the device;

FIG. 10 is an electrical schematic drawing depicting the audible alarm circuitry making up a portion of the overall controller device;

FIG. 14 is an essentially schematic cross-sectional view illustrating the configuration of the preferred dual flow control valve used in the invention;

FIG. 15 is a perspective view of the dual flow control valve;

FIG. 16 is a cross-sectional view of the valve illustrated in FIG. 15, depicting in detail the construction of the central flow control disc;

FIG. 17 is a partially sectional view taken along line 17—17 of FIG. 16;

FIG. 18 is a partially sectional view taken along line 18—18 of FIG. 16;

DETAILED DESCRIPTION OF THE PREFERRED EMBODIMENTS

I. Pneumatic Circuits and Operation

Figure 2:
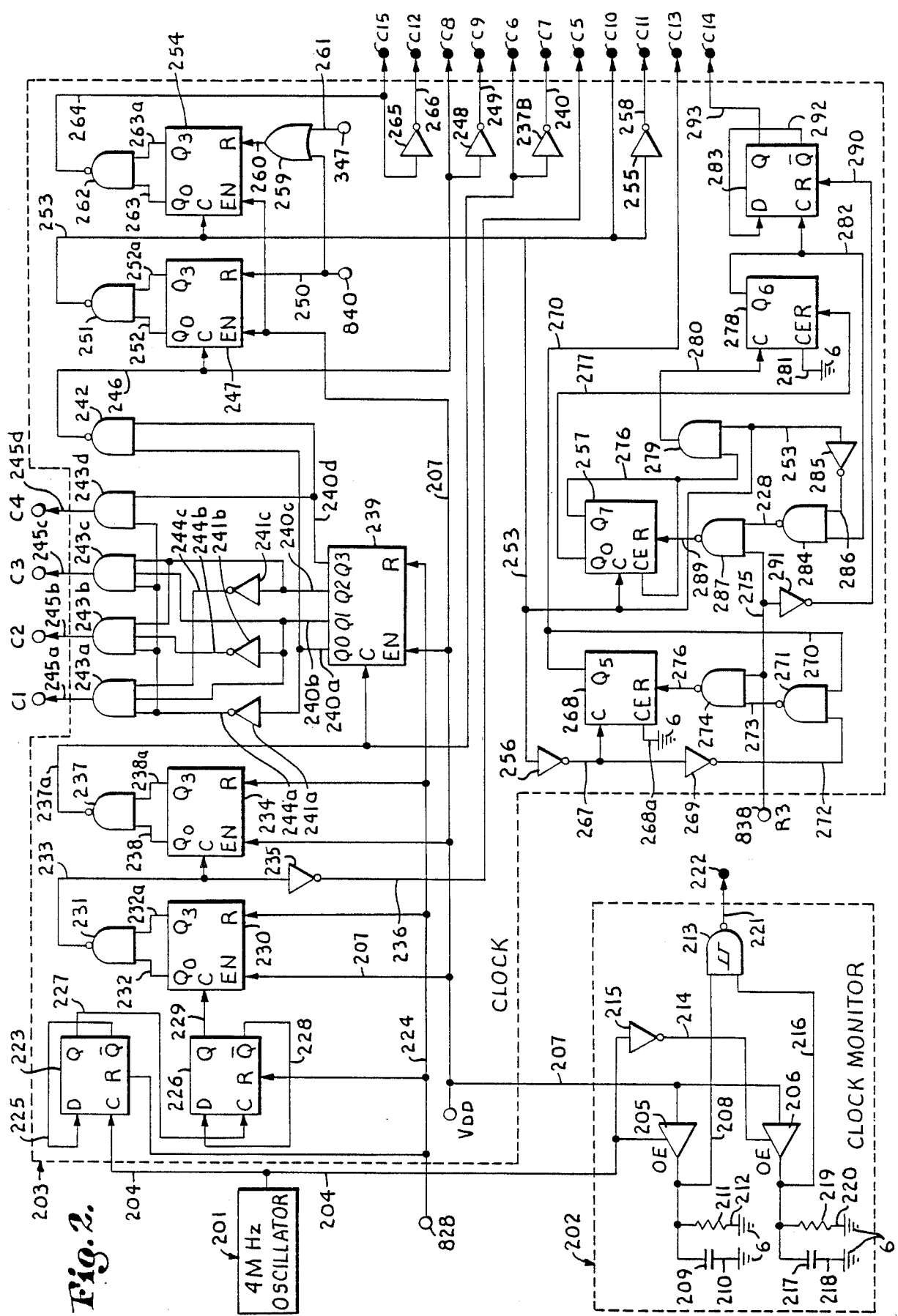
FIG. 2 is an electrical schematic drawing illustrating the preferred clock and monitor circuit forming a part of the overall controller device.

A. The oxygen control apparatus in accordance with the present invention, in broad outline, includes a pneumatic circuit and a corresponding electrical control circuit. In the presently contemplated forms of the invention, there is provided a so-called "hospital" unit (FIG. 19) designed to be used in the institutional setting of a hospital or similar health care facility, and also a "home" unit (FIG. 20) designed to be used by the patient at home. In addition, it is also within the ambit of the invention to provide units designed for other specific purposes such as patient transport, and also for use in conjunction with an oxygen concentrator.

The supplemental medicinal gas supply systems of the invention (see, e.g., FIG. 1) normally include a pressurized source of medicinal gas 18, which would typically be oxygen, together with an electrically operated three-way demand solenoid valve generally referred to by the numeral 22 which is operatively coupled to the source 18 and is operated through the electrical control circuitry in a manner to be described in detail. Further, a gas output line 24 is operatively secured to the demand solenoid valve 22, and has the usual nasal cannula 26 secured thereto for delivery of medicinal gas to the patient.

Figure 19:
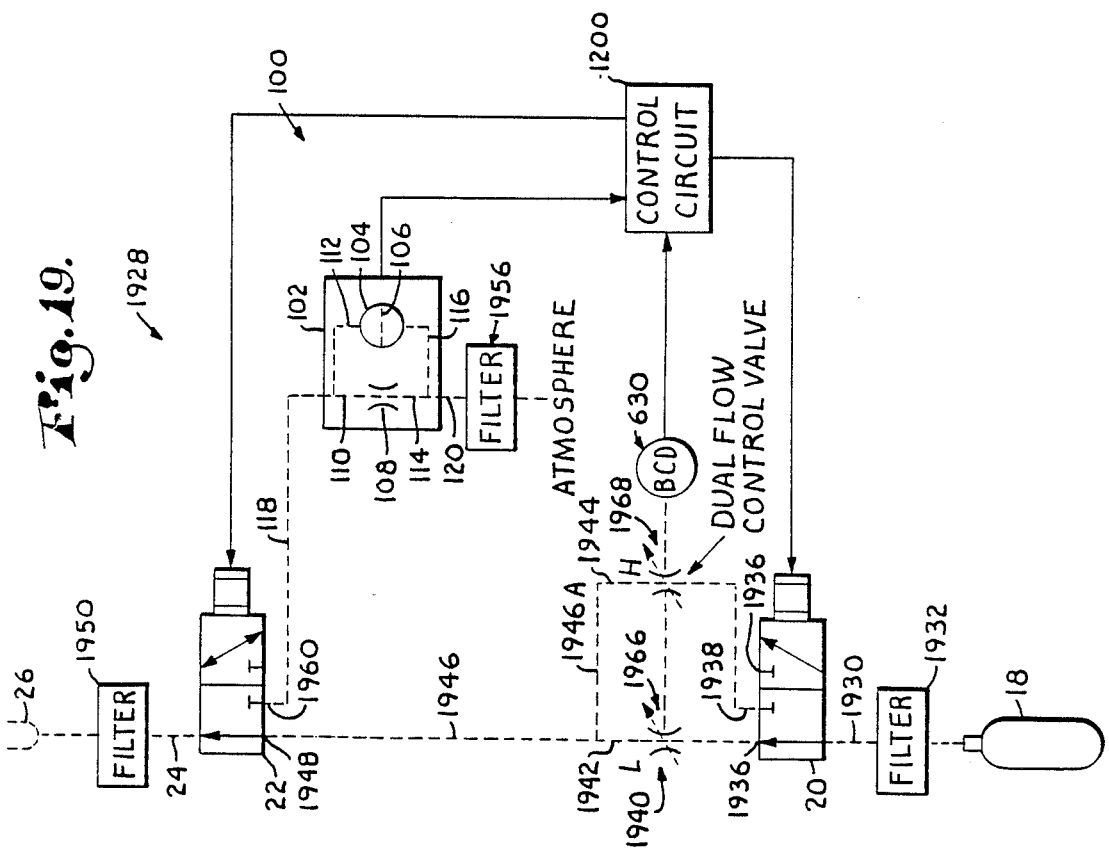
FIG. 19 is a block diagram illustrating the pneumatic components of the preferred "hospital" embodiment of the invention.

Attention is next directed to FIG. 19 which illustrates in schematic form the so-called "hospital" unit and particularly the pneumatic circuitry and components associated therewith. Such hospital unit is broadly designated by the numeral 1928, and includes the noted oxygen source 18 and solenoid valve 22. In addition, however, and as shown in FIG. 19, the unit 1928 is provided with a line 1930 from the source 18, with a conventional filter 1932 interposed within the line 1930.

As illustrated, the line 1930 is operatively connected to an inlet port of a three-way flow solenoid valve 20. This valve 20 includes a pair of outlet ports 1936, 1938 which are each connected to corresponding inlets provided with a dual flow control valve broadly referred to by the numeral 1940. This valve 1940, illustrated in detail in FIGS. 14–18, will be described more fully below. For purposes of the present discussion, however, it is sufficient to recognize that the valve 1940 includes a pair of respective, low and high flow outlets 1942, 1944. These flow outlets are in turn operatively connected through lines 1946 and 1946a to one inlet 1948 of the demand solenoid valve 22. As is typical in devices of this character, a conventional filter 1950 is interposed within patient gas output line. 24 between valve 22 and cannula 26.

The overall device 1928 further includes pneumatic/electrical sensing apparatus broadly referred to by the numeral 100 which is designed to sense the beginning of the patient's inhalation, such being significant to the proper operation of the overall device In detail, the sensing apparatus 100 includes a pressure sensor 102, a restrictor 108 and a filter 1956. A pneumatic line 118 is provided between the second inlet port 1960 of valve 22 and pressure sensor 102. Moreover, another pneumatic line 114 is operatively coupled with line 118 ahead of sensor 102, and filter 1956; moreover, it will be seen that the restrictor 108 is interposed within the line 114. Finally, another pneumatic line 116 is operatively coupled to the sensor 102 and line 114 between restrictor 1954 and filter 1956.

The pressure sensor 102 includes an internal diaphragm 106, the operation of which is described in full detail below The dual flow control valve 1940 is operable for permitting selection of a prescribed flow of medicinal gas to the patient by means of an external knob and selector dial. Internally, and again in a generalized sense, the valve 1940 includes a low or prescribed flow restrictor in the form of a plurality of differently sized orifices as will be explained, together with a high, pulse flow restrictor 1968, which again is in the form of a plurality of differently sized apertures. Finally, the valve 1940 includes a binary coded decimal encoder 630 which serves to output binary electrical data corresponding to the gas flow rate selected by the user when employing the valve 1940.

The electrical aspects of the overall device 1928 includes control circuitry 1200 which is associated with the above-described pneumatic components by the schematically illustrated full lines. Thus, the control circuitry is operatively connected to the flow solenoid valve 20, the encoder 630, pressure sensor 102, and demand solenoid valve 22. Here again, the specific interconnections and details regarding control circuitry 1200 are set forth hereinafter.

The device 1928 is designed to normally operate in a manner to deliver to the patient relatively high flow rate, short time pulses of oxygen at precisely timed intervals during the patient's breathing cycle, which are designed to be essentially the physiological equivalent of delivery of relatively low flow rates of gas to the patient on a continuous basis. However, the safety and control features of the device are associated with the valves 20, 22 in such manner that the unit is shifted to the conventional continuous flow mode of operation upon the occurrence of power failure, abnormally high or low breath rates or various circuit failures within the control circuitry 1200.

In any event, during such normal operation the user first rotates a dial (not shown) associated with the dual control valve 1940, to a position corresponding to a continuous flow rate of gas prescribed by the physician. That is to say, physicians almost universally prescribe a certain rate of oxygen or other gas to the patient, e.g., 5 liters per minute. The knob associated with the valve 1940 would then be turned to a position corresponding to such flow rate, although it will be understood that the overall device does not normally supply such flow rate on a continuous basis; rather, during normal operation, the substantially physiological equivalent of the prescribed flow rate is supplied using the precisely timed, high flow rate pulses of gas to the patient.

When the valve 1940 is manipulated as described, the high flow rate restrictor 1968 is adjusted to position an appropriately sized aperture for communication with outlet port 1944 of the valve 1940. At the same time, the binary coded decimal encoder 630, being operatively connected to the handle, generates a digital electrical output which is directed to control circuitry 1200 in order to "set" this circuitry in operation in accordance with the prescribed flow rate.

Again referring to the normal operation of the device 1928, the control circuitry 1200 serves to normally continuously energize the flow solenoid valve 20 in order to continuously communicate gas line 1930 with outlet port 1938 of the valve 20. On the other hand, the control circuitry 1200 selectively energizes and de-energizes the demand solenoid valve 22 so as to deliver the noted "pulses" of oxygen or other medicinal gas to the patient. Thus, and considering the period of initial inspiration wherein oxygen is to be delivered to the patient, the demand valve 22 is in the position illustrated in FIG. 19, i.e., it is de-energized. In this condition, it will be appreciated that gas from the source 18 travels via line 1930 through valve 20 to outlet port 1938. Thereupon, gas passes through the selected orifice forming a part of the high or pulse restrictor 1968, and thence through high flow outlet 1944. The gas then passes through the lines 1946a and 1946 to the inlet port 1948 of de-energized valve 22 for ultimate delivery via line 24 to cannula 26.

On the other hand, during those stages of the patient's breathing cycle where no oxygen is being delivered, the demand solenoid valve 22 is energized, and is moved leftwardly from the position depicted in FIG. 19. As can be seen this moves the port 1960 into communication with gas flow line 24 and port 1948 cut of communication with line 24, thereby stopping flow of oxygen to the patient.

Furthermore, in this energized position of the solenoid valve 22, the line 118 is in communication with gas line 24 leading to the cannula 26 The patient inhales a very small amount of ambient air through filter 1956 and restrictor 108. This correspondingly creates a pressure differential across the restrictor 108 which is communicated to both sides of the diaphragm 106 forming a part of pressure sensor 102, via the pneumatic lines 118, 116. Of course, during exhalation when the solenoid 22 is energized, exhaled air passes likewise through the line 24, valve 22, and lines 118, 114. Therefore, both during inspiration (except when the gas pulse is being delivered) and exhalation, corresponding pressure differentials are created across the restrictor 108, such being sensed by the diaphragm 106 of sensor 102. The diaphragm 106 is equipped with appropriate electrical, variable resistors on the face thereof in such a manner that upon diaphragm distortion an electrical signal analog of the sensed pressure differential is created. Such differential pressure analogs, created during the patient's breathing cycle when the valve 22 is energized, are communicated by appropriate electrical lines to the control circuitry 1200.

As noted above, under certain unusual or upset conditions, the device 1928 operates in the conventional continuous flow mode. In order to accomplish this operation, both of the solenoid valve 20, 22 are continuously de-energized, to the condition depicted in FIG. 19. As a consequence, it will be seen that gas from source 18 passes through line 1930 and thence through outlet port 1936 of valve 20. Such gas thereupon flows through the selected orifice of the low flow restrictor 1966 and thence through outlet 1942 to line 1946. Such line is coupled through the solenoid valve port 1948 to line 24 and ultimately to cannula 26.

As will be explained further below, the operating mechanism forming a part of the dual flow control valve 1940 serves to set both the low and high flow restrictors, as well as BCD encoder 630. Thus, when a physician prescribes a given continuous flow rate of oxygen, and the valve 1940 is correspondingly set, the appropriate high flow restrictor orifice is positioned for flow communication purposes, and simultaneously the appropriately or continuous flow aperture is also set to accommodate the power off or upset conditions giving rise to continuous flow operation. In addition, of course, manipulation of the control valve also sets the encoder 630, to communicate the dial setting to control circuitry 1200.

Figure 20:
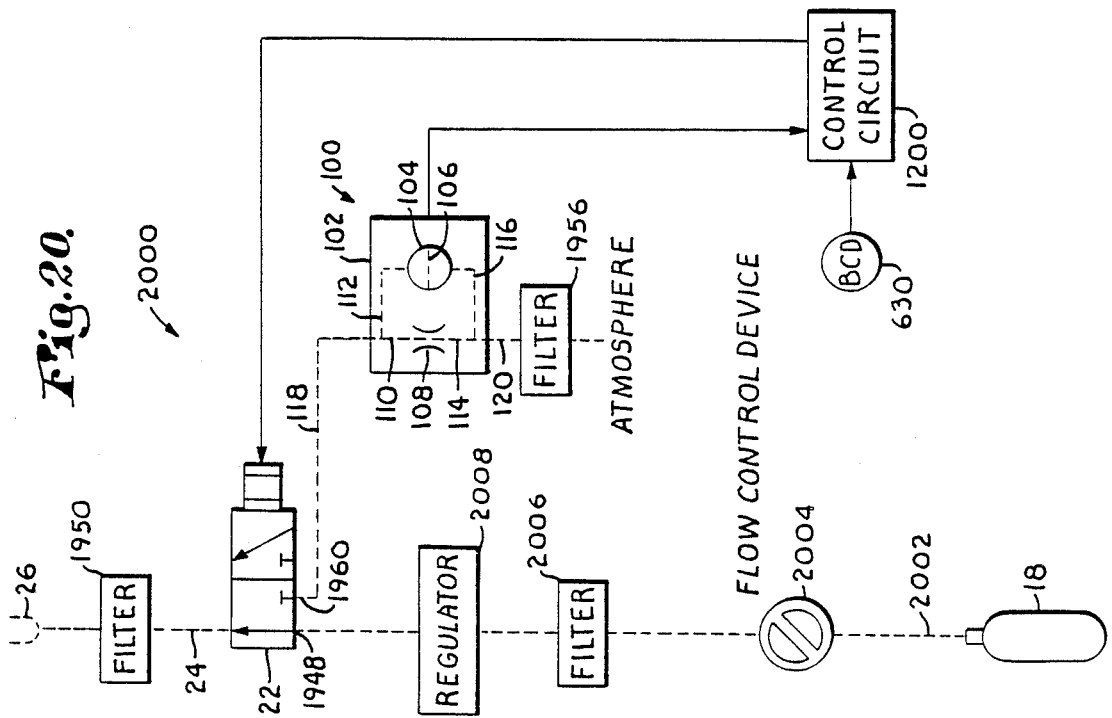
FIG. 20 is a block diagram illustrating the pneumatic components of the preferred "home" embodiment of the invention.

Attention is next directed to FIG. 20 which illustrates in schematic for the pneumatic/ electrical components of the so-called "home" controller 2000. The structural differences between the unit 2000 and the unit 1928 described above are principally based upon the fact that in hospital or institutional settings, the pressure of oxygen or other medicinal gas supplied to the system is essentially uniform (e.g., 50 psig). On the other hand, in the home context the gas pressures can vary widely, and therefore precautions must be taken to properly accommodate such pressure variations.

In any event, the device 2000 is in many respects similar to that of FIG. 19, and where appropriate like reference numerals have been employed. The device 2000 therefore is used in conjunction with a supply 18 coupled with a flow line 2002. A variable flow control device 2004 is interposed within line 2002, along with a filter 2006 and a pressure regulator 2008. The flow control device 2004 is a manually operated unit designed to restrict the flow of gas from the supply 18 at a setting corresponding to the prescribed continuous flow of gas. On the other hand, the regulator 2008 is designed to supply a continuous, constant pressure output of gas at a given level, as long as the input pressure to the regulator is at least this given level. Thus, the pressure regulator may be set to deliver gas at a pressure of 20 psig, and will do so as long as the input to the regulator is of at least this magnitude.

The output from regulator 2008 is fed via a line 2010 to the three-way demand solenoid valve 22. This unit is identical with that described with reference to FIG. 19, and accordingly includes a pair of inlet ports 1948, 1960. The outlet from the valve 22 travels through line 24 to cannula 26, all as illustrated in FIG. 20.

In like manner, the device 2000 includes a pressure sensor 102 associated with a flow restrictor 108 and gas flow lines 118, 114 and 116, as well as filter 1956.

The unit 2000 further is provided with binary coded decimal encoder 630 which is identical with the encoder 630 described with reference to FIG. 19. However, in this instance, the encoder 630 is individually set, i.e., it is not simultaneously set along with a flow control valve.

The use of the home unit illustrated in FIG. 20 proceeds as follows. First, the continuous flow rate prescription received from the physician is set on the flow control device 2004 and on the encoder 630. Setting of the last mentioned component in turn communicates the corresponding digital information to control circuitry 1200. Normal operation of the device 2000 after initial setting thereof proceeds as follows. First, and considering when pulses of oxygen or other gas are to be delivered to the patient, the control circuitry 1200 de-energizes solenoid valve 22 so that the latter assumes the position depicted in FIG. 20. In this orientation, it will be seen that oxygen passes from regulator 2008 and line 2010 to inlet port 1948. Such gas thereupon passes through valve 22 through line 24 to cannula 26. The time during which the valve 22 is de-energized is of course controlled by means of the circuitry 1200 in a manner to be explained.

In any event, during the majority of the patient's breathing cycle when no gas is being delivered, the solenoid 22 is energized thereby communicating inlet port 1960 of the valve with line 24 In this orientation, it will be seen that cannula 26 is in communication with pressure sensor 102 and the related apparatus previously described, so as to sense and monitor the patient's breathing cycle, in the same manner as described with reference to the FIG. 19 apparatus.

Figure 13:
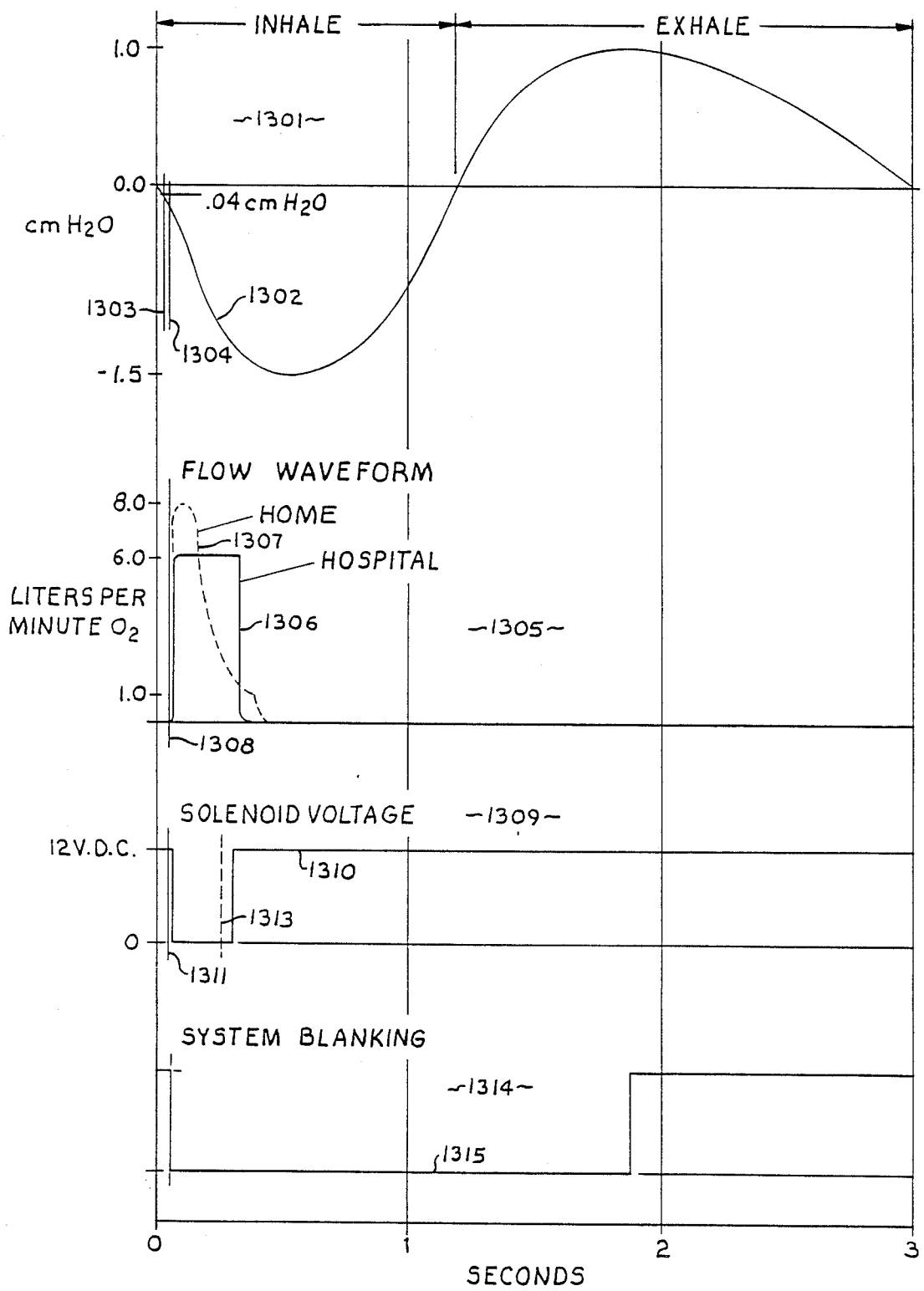
FIG. 13 is a series of four time graphs respectively illustrating the patient respiratory pressure wave form, the pulse flow wave form of delivered gas pulses for both the "home" and the "hospital" embodiments, the time operational characteristics of the demand solenoid valve of the invention, and wave form of the output from the system blanking circuitry.

Inasmuch as the device 2000 includes the upstream pressure regulation system ahead of valve 22, the wave form of gas flow actually delivered to the patient varies somewhat as compared with the wave form generated using the device of FIG. 19. That is to say, in the FIG. 19 device, because of the essentially constant gas pressures encountered, the wave form of the delivered pulse is essentially rectangular. On the other hand, in the FIG. 20 device, during the time when valve 22 is energized, gas pressure will build up within regulator 2008 and line 2010. This follows from the fact that gas is continuously communicated from the source 20 to the regulator, even though the valve 22 is energized. As a consequence, when the valve 22 is de-energized to permit pulse flow of gas, an initial "puff" of such gas may be delivered. This in turn means that the wave form of the pulse of oxygen delivered is not rectangular, but includes an initial spike followed by an exponential decay. Of course, the patient still receives the substantially physiological equivalent of the prescribed oxygen flow, but the wave forms of the delivered pulses are somewhat different as compared to the hospital unit of FIG. 19. These wave forms are illustrated in FIG. 13.

As in the case of the FIG. 19 embodiment, the FIG. 20 device provides for continuous oxygen flow to the patient in the event of a power outage, or abnormal breathing or circuitry malfunction conditions. In this operational mode, the control circuitry de-energizes the solenoid valve 22, thereby directly opening the flow path between source 18 and cannula 26 for delivery of oxygen at the prescribed, continuous flow rate.

B. Dual Flow Control Valve

Attention is next directed to FIGS. 14-18 which illustrates the preferred dual flow control valve 1940. The valve broadly includes a pair of essentially circular, centrally-apertured valve bodies 1400, 1402 each provided with three circumferentially-spaced, outwardly-projecting annular connection bosses 1404-1408 and 1410-1414. As illustrated, the bosses 1404-1408 are designed for alignment with the corresponding bosses 1410-1414, in order to provide through-holes for mounting screws so as to clamp the bodies 1400, 1402 together and mount the same. In addition, the lowermost valve body 1402 includes a total of three integral, downwardly-directed mounting feet 1416-1420 respectively located between and radially inwardly of the circumferential bosses 1410-1414.

The uppermost valve body 1400 is provided with a central axial bore 1422 which communicates with a radially outwardly-extending irregular recess 1424. The recess 1424 includes a seal-receiving region 1426 at the junction between bore 1422 and the recess 1424. The body 1402 further includes a pair of outwardly-projecting connection nipples 1428 and 1430 for inflow of gas to the valve. The nipple 1428 is provided with a central bore 1432 which extends inwardly into the valve body 1402 a selected distance, whereupon the bore turns downwardly for communication with an annular enlarged region 1433. Similarly, the nipple 1430 is provided with a central bore 1434 which extends radially inwardly within body 1402 for a lesser length than the bore 1432 (compare FIGS. 17 and 18), whereupon the bore 1434 turns downwardly and communicates with an annular region 1436. Finally, the body 1402 is provided with a continuous, circumscribing, seal-receiving recess 1438 adjacent the lower and outer margin thereof.

The corresponding lower body 1402 is in many respects similar to the body 1400. Thus, the body 1402 is provided with a pair of gas outlet nipples 1438, 1440 which are directly beneath the corresponding inlet nipples 1428, 1430. The nipple 1438 is provided with an inwardly-extending bore 1442 which extends into body 1402 the same distance as corresponding nipple bore 1432, whereupon the bore 1440 turns upwardly to communicate with enlarged annular zone 1444. Similarly, the bore 1440 is provided with a somewhat shorter, inwardly-extending bore 1446 which extends into body 1402 the same distance as corresponding bore 1434, and turns upwardly to terminate at an enlarged annular region 1448. The body 1402 further includes a central bore 1450 which communicates with a recess 1452. The latter is provided with annular seal-receiving zones 1454 and 1456 adjacent bore 1450 and proximal to the outer margin of the body 1404, respectively.

The lower valve body 1402 is also provided with a deadend bore 1458 in the region thereof remote from nipple 1438 and oriented radially inwardly from the outer surface of the body 1402 a distance equal to the radially inward spacing of the annular regions 1436, 1448, for purposes which will be made clear. The bore 1458 houses a coil spring 1460, the latter yieldably supporting a detent ball 1462.

The valve bodies 1400, 1402 are designed for mating interconnection thereof to cooperatively present a through-bore comprising the aligned central bores 1422, 1450, together with a radially outwardly-extending recess presented by the recesses 1424, 1452 of the respective valve bodies. In addition, it will be observed that the bores 1432 and 1442 are oriented in a directly opposed relationship for communication, whereas the shorter bores 1434. 1446 are similarly positioned for communication therebetween. Finally, it will be seen that appropriate O-ring seals 1464, 1466, 1468, 1470 and 1472 are provided for creating a gas-tight valve construction. These seals 1464-1472 are oriented as illustrated in FIG. 17, within the previously described recesses and annular regions.

The overall valve 1940 further includes a rotatable selector 1474 which includes an elongated upright central shaft 1476 which extends through the bores 1422, 1450 as illustrated. A selector knob (not shown) is adapted for connection to the projecting portion of shaft 1476 which extends above valve body 1400. This knob cooperates with a flow rate selector dial, also not shown, which is provided with the valve assembly.

The selector 1474 further comprises a radially outwardly-extending, disc-like extension 1478 which is integral with the shaft 1476 and located within the central recess presented by the cooperating valve bodies. The extension 1478 is provided with two sets of circularly arranged apertures therethrough which are respectively oriented for communication with the bores 1432, 1442 and 1434, 1446. That is to say, the innermost set of apertures 1480 are oriented for communication with the longer bore set 1432, 1442, whereas the radially outer bore set 1482 are positioned for communicating the shorter bore set 1434, 1446.

Each of the individual through-bores making up the sets 1480, 1482 extend completely through the extension 1478 and are of the same diameter. It will be noted, however, that the bore making up the radially outer set 1482 are provided with a circular bevel at the lower ends thereof adjacent valve body 1402; the importance of this feature will be explained below. In order to provide settable, different flow rates of gas through the valve structure, the extension 1478 carries a rigid metallic central apertured disc 1484. This disc 1484 is correspondingly provided without sets of orifices 1486, 1488 therethrough. The orifices making up set 1486 are aligned with the apertures making up the set 1480 provided in extension 1478, whereas the orifices making up the outer set 1488 are respectively in alignment with the apertures making up the set 1482. It will further be observed that each of the orifices is of a different diameter, so that the effective cross-sectional area presented for gas flow at each of the orifice-aperture sets is different.

in order to provide an indexing function for the valve arrangement, the detent ball 1462 is designed to successively seat within the extension apertures making up the radially outer set 1482. As can be appreciated, this provides a sensory "click" or feel as the selector 74 is rotated, and further insures that the selector is properly positioned for each of the possible gas flow rates.

In order to provide an "off" function, each of the aperture sets 1480, 1482 is provided with a deadend bore which does not extend completely through the extension 1478. These bores are located at the circumferentially offset points 1490, 1492 (see FIG. 16) so that when the selector 1474 is rotated 180° from the FIG. 16 position, the deadended "off" bores serve to interrupt fluid communication between the nipple bore sets 1432, 1442 and 1434, 1446.

As schematically illustrated in FIG. 14, and further explained hereinabove with reference to FIG. 19, the shaft 1476 of the selector 1474 is operatively connected to the binary coded decimal encoder 630; hence, when a prescribed flow rate is selected using selector 1478, the BCD 630 is simultaneously operated.

The operation of the valve 1940 will now be apparent from the foregoing description. Specifically, when the user is advised by a physician of a prescription flow rate of medicinal gas, this flow rate (which would conventionally be prescribed in liters per minute) is selected using the knob end dial (not shown). This serves to rotate the extension 1478 until the appropriate aperture/orifice set for the selected flow rate comes into communication with this nipple orifices 1432, 1442 and 1434, 1446. For example, if a prescribed flow rate of 5 liters per minute is selected, the appropriate aperture/orifice set communicating the prescribed or continuous flow nipples 1428, 1438 would permit a continuous flow rate of 5 liters per minute. On the other hand, the corresponding aperture/orifice set communicating the peak or pulse flow nipples 1430, 1440 would permit a somewhat higher flow rate than that specifically described, so that the device can deliver the desirable physiological equivalent of the prescribed continuous flow rate in a pulse mode.

With particular reference to the FIG. 19 schematic representation, it will also be clear that the outlet port 1936 of solenoid valve 20 is operatively coupled with the continuous flow inlet nipple 1428 of the valve 1940, whereas the outlet port 1938 of the solenoid valve 1934 is coupled with the peak or pulse flow inlet nipple 1430. Correspondingly, the continuous flow output nipple 1438 corresponds to the previously described outlet 1942, with the pulse flow outlet nipple 1440 corresponding to the outlet 1944. The lines interconnecting the restrictors 1966 and 1968, and the encoder 630, likewise correspond with the previously set selector shaft 1476 and its associated structure.

II. Electrical Circuits and Operation

A. Overview

Broadly speaking, the main purpose of the preferred electrical circuitry described in detail in Part II.B. below is to de-energize demand solenoid 22 near the beginning of the patient's inhalation to allow oxygen to flow, and then to re-energize demand solenoid 22 a short time later to thereby provide a precise pulse of oxygen substantially physiologically equivalent to a prescribed continuous flow. In order to accomplish this purpose reliably, safely, and with precision, the circuitry and associated pneumatic apparatus does the following: senses valid inhalation; calculates the duration of the oxygen pulse based on both the duration of the three previous breaths and the prescribed flow rate with an assumed inhalation-exhalation ratio; de-energizes demand solenoid 22 for a period correlated with such calculated time and then re-energizes it; prevents spurious re-triggering of the system during the balance of the inhalation cycle; and compensates for drift in the sensitivity of the inhalation sensor.

Additionally, the electrical circuitry allows for component warm-up after power is initially turned on, adjusts the operation if the patient breath rate is outside a predetermined normal range, adjusts the operation if the patient ceases inhaling through the cannula, and provides r for continuous oxygen flow in the event of power failure or system failure.

The basic system cycle starting time reference for the electrical circuitry is derived from the patient breath cycle and is more particularly, that point in patient inhalation when the patient's nasal vacuum reaches or exceeds 0.04 cm. water. The four graphs of FIG. 13 illustrate the breath cycle and other events during normal system operation. The four graphs all have a common time ordinate Graph 1301 includes plot 1302 of patient nasal pressure in centimeters water during a typical breathing cycle versus time. Vertical line 1303 crosses plot 1302 when nasal pressure is −0.04 cm. water which occurs typically between about 5 to 50 milliseconds after inhalation begins. Vertical line 1304 crosses the time ordinate 10 milliseconds after vertical line 1303; hence the starting time is 10 milliseconds plus the time for patient nasal vacuum to reach 0.04 cm.

Graph 1305 represents the flow wave form in liters per minute of oxygen flow versus time. Plot 1306 represents a typical oxygen pulse for a hospital unit with the patient breathing at 20 breaths per minute with a prescribed continuous rate of two liters per minute. Plot 1307 (dashed line) represents a typical oxygen pulse for the home unit also at 20 breaths per minute and prescribed continuous rate of two liters per minute. Vertical line 1308 indicates the beginning of oxygen pulses 1306 and 1307 and coincides with line 1304.

In the preferred embodiment of the present invention an inhalation to exhalation [I/E] ratio of 1:1.5 is incorporated within a read only memory of the device later described. That is, inhalation time is taken to be 40% of the time of a total breath cycle. With this ratio in mind then, the preferred embodiment, when operated in the pulse mode, delivers a constant "minute volume" of gas to the patient irrespective of breath rate (within normal limits). That is to say, for example, if the prescribed continuous flow rate is 1 liter per minute (1000 milliliters per minute) the volumetric sum of all the pulses averaged per minute equals 400 milliliters (40% of 1000 milliliters). at all normal breath rates. Of course, other I/E ratios such as 1:2 could also be employed. Furthermore, it is to be understood that the present invention contemplates that the I/E ratio is a parameter which may be independently measured by direct measurements of both inhalation and exhalation times, to thus produce another independent variable along with breath rate and prescribed flow rate. This may be desirable in some circumstances; however, use of a constant I/E ratio factor is preferred for a variety of reasons including marketing economics.

Graph 1309 is a plot 1310 of the voltage applied to the coil of the demand solenoid 22. When the coil is de-energized, demand solenoid 22 allows oxygen to flow to the patient. When the coil is energized, demand solenoid valve 22 prevents oxygen flow. Vertical line 1311 indicates the time point in the breath cycle at which the demand solenoid is de-energized which also coincides with lines 1308 and 1304. Dotted vertical line 1313 represents the end of the calculated time of the pulse width. The demand solenoid remains de-energized, however, for ar additional 11 milliseconds to allow for rezeroing which is explained in more detail in the discussion below. This extra 11 milliseconds during which the demand solenoid is de-energized causes the oxygen pulse width to be 11 milliseconds longer than it would be otherwise; however, this is taken into account in the data used by the circuitry to calculate pulse duration.

In graph 1314, plot 1315 represents the time, called blanking time, during which the electrical circuitry does not reinitiate an oxygen flow pulse in response to patient inhalation. If system blanking did not occur, additional oxygen flow pulses might occur after the first pulse because the patient is still inhaling at the end of the oxygen flow pulse. Thus, the beginning of the blanking time coincides with lines 1304, 1308, and 1311; blanking time extends well into the exhale portion of the breathing cycle as shown on graph 1314.

Figure 12:
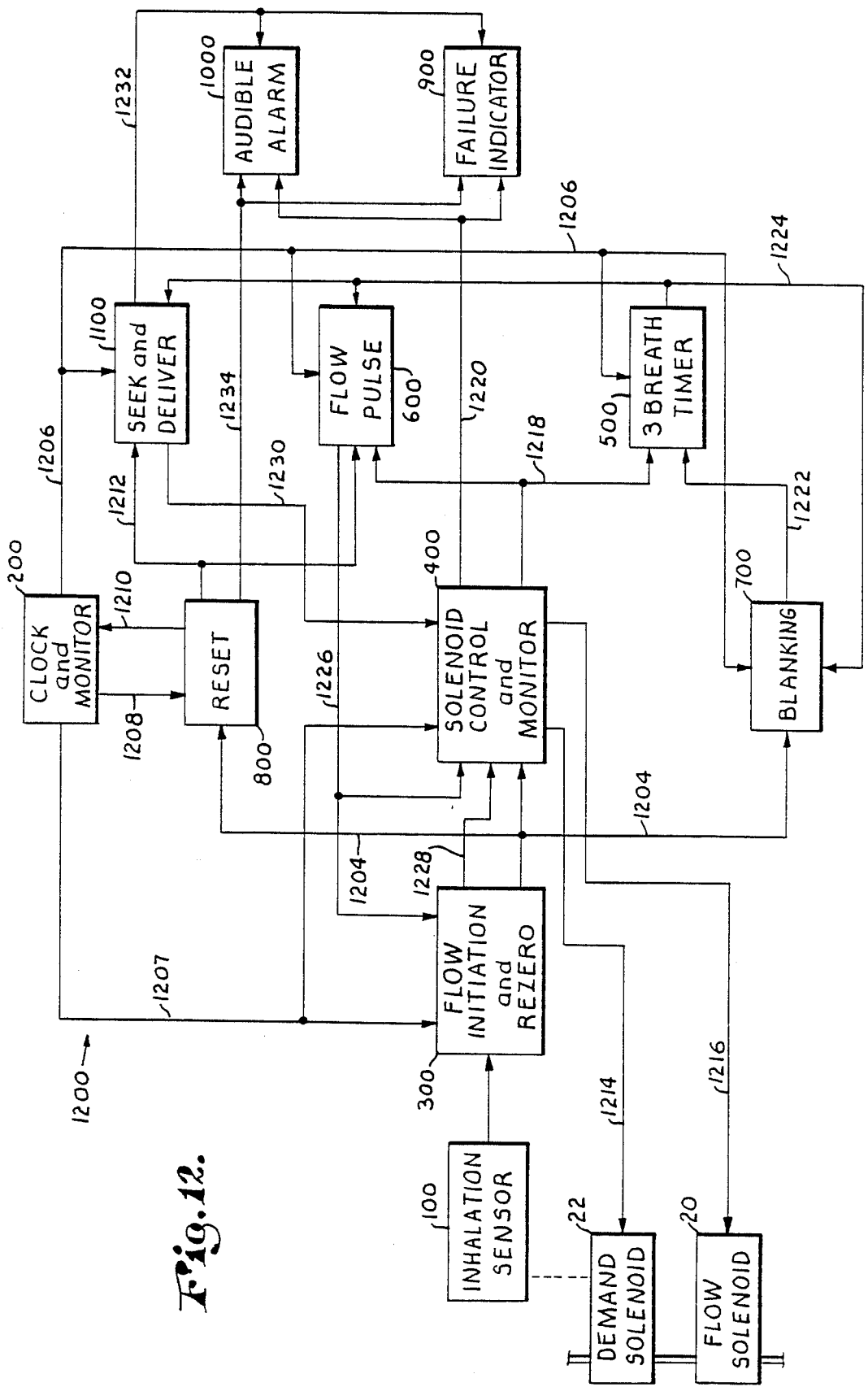
FIG. 12 is a block diagram illustrating the primary interconnections between the functional modules of the device.

FIG. 12 illustrates in block diagram form the primary modules and interconnections of control circuit 1200 and thereby the primary relationships therebetween. Circuit 1200 includes Inhalation Sensor 100, Clock and Monitor 200, Flow Initiation and Rezero 300, Solenoid Control and Monitor 400, Three-Breath Timer 500, Flow Pulse 600, Blanking 700, Reset 800, Failure Indicator 900, Audible Alarm 1000, and Seek/Deliver 1100

Circuit 1200 also includes the primary electrical connection lines which are enumerated and described in the discussion below.

By way of overview and to provide a broad outline of primary functions, the control modular level with reference to FIG. 12. Then, individual modules and the components thereof will be described in greater detail under II.B. below.

Inhalation Sensor 100 provides a continuous direct current output voltage 36 corresponding to the patient's breathing cycle (except when solenoid 22 is de-energized). When demand solenoid 22 is de-energized, sensor 100 is pneumatically isolated from the patient cannula and the output voltage is a nominal, mid-range, no-flow reference voltage—that is, a value representing no inhalation and no exhalation.

Flow Initiation and Rezero [FIR] 300 receives the breathing cycle signal from sensor 100 via line 1202 as input to a comparator; the comparator also receives an analog reference voltage produced by FIR 300 from a value stored in memory. If the breathing cycle voltage decreases to below the reference voltage, then the output from the comparator goes "off", that is, drops to volts from 5 volts D.C. (the balance of the circuits described in this section are also digital circuits whose outputs are "on" at +5 volts D.C. and "off" at 0 volts D.C.). If the breathing cycle signal voltage is greater than the reference voltage, then the comparator output is on. The purpose of the reference voltage comparison is to compensate for electronic drift of the output from sensor 100. Sensor 100 is so sensitive that ambient temperature and other factors may cause sensor 100 output voltage to drift up or down from nominal. The reference voltage is equal to the sensor 100 output voltage which existed during the previous breath cycle when demand solenoid 22 was de-energized and sensor 100 was thus pneumatically isolated from the patient cannula. Flow Initiation and Rezero 300 also biases the sensor 100 reference voltage so that the comparator goes off when patient nasal vacuum equals or exceeds 0.04 cm. water. This is done to prevent spurious indication of inhalation during the normal breath pause following exhalation.

Flow Initiation and Rezero 300 also incorporates a time delay so that FIR 300 produces an on output via line 1204 only if the comparator is off for 10 milliseconds. The end of this 10 millisecond delay corresponds to vertical lines 1304, 1308, and 1311 on the graphs in FIG. 13. This time delay provides additional validation that genuine patient inhalation has occurred. The FIR 300 on output is transmitted via line 1204 to Reset 800, Solenoid Control and Monitor 400, and Blanking 700.

Clock and Monitor 200 uses a standard Colpitts oscillator with a ceramic element to produce a 4 megahertz square wave signal. Clock and Monitor 200 then scales the 4 MHZ. signal into a series of various 5 V.D.C. square wave signals ranging in frequency from 0.1 HZ. to 100 KHZ. which signals are conveyed over a number of connections represented by lines 1206 and 1207 to the various circuit modules. Some of these output clock pulses are inverted depending on needs of the individual circuit which uses the pulses.

Clock and Monitor 200 also includes a circuit for detecting a malfunction of the oscillator; these malfunctions include steady on, steady off, and frequency too low or too high. If the monitor detects an oscillator abnormality, it produces an output transmitted via line 1208 to Reset 800. Clock and Monitor 200 also receives an input from Reset 800 via line 1210 which resets and resynchronizes various frequency scaling circuits when Reset 800 receives a flow initiation signal via line 1204.

Reset 800, upon reception of a flow initiation signal via line 1204, resets Clock and Monitor 200 as mentioned above and also resets via line 1212 Seek/Deliver 1100, Audible Alarm 1000, and Failure Indicator 900, which resetting indicates to these circuits that a valid inhalation has occurred.

Solenoid Control and Monitor [SCM] 400, upon receiving a flow initiation signal via line 1204, de-energizes demand solenoid 22 via line 1214 which allows oxygen to flow to the patient and which pneumatically isolates sensor 100. In normal operation, SCM 400 keeps flow solenoid 20 energized via line 1216. Simultaneously with de-energizing demand solenoid 22, SCM 400 turns off its normally on output signal via line 1218 to low Pulse 600 and Three-Breath Timer 500.

SCM 400 also monitors both solenoid valves 22 and 24 for electrical malfunction via lines not shown. In the event an abnormality is detected, SCM 400 de-energizes both solenoids 22 and 24 which puts the pneumatic system in a continuous flow mode. SCM 400 also provides an on signal represented by line 1220 to Audible Alarm 1000 and Failure Indicator 900 when such an abnormality occurs.

Blanking 700 receives the flow initiation signal via line 1204 at which time blanking 700 turns off its normally one signal via line 1222 to Three-Breath Timer 500. Blanking 700 also receives count data via databus 1224 from Three-Breath Timer 500. Upon receiving the flow indication signal, blanking 700 begins counting down the count received from Three-Breath Timer 500 at an appropriate clock pulse rate received from Clock and Monitor 200 via line 1207. The length of time required to complete the countdown is the blanking time represented on graph 1314 of FIG. 13. At the end of the blanking time, Blanking 700 output via line 1222 goes on again.

Three-Breath Timer [3BT] 500 includes four pulse counters, each of which receives clock pulses via line 1206 from Clock and Monitor 200. In normal operation, at any one point in time, three of the counters are actively counting pulses while the fourth is delivering its accumulated count data via databus 1224 to Blanking 700, Flow Pulse 600, and Seek/Deliver 1100. Three-Breather Timer 500 advances to the next counter in sequence when either of inputs received via lines 1218 and 222 from SCM 400 and Blanking 700 respectively go off This advancement freezes the count on the selected counter and resets the formerly selected counter to enable it to begin counting pulses again. The selected counter continuously supplies its count data to databus 1224. Because the counters are selected in sequence, the count on the selected counter represents the accumulated count over the three previous breath cycles.

Flow Pulse 600 receives input from SCM 00 via line 1218 and data from 3BT 500 via databus 1224 Flow Pulse 600 also receives data in binary encoded decimal form from the flow rate selector valve 1940 indicating the prescribed continuous flow rate. By using the prescribed flow rate information and the count from the three previous breaths an address, Flow Pulse 600 selects from a read-only-memory (ROM) element a value (ROM value) which value is also based on the inhalation-exhalation ratio. This ROM value is used to convert an input clock pulse received via line 1206 to a ROM frequency. The ROM frequency is used as the frequency with which to count the 3BT 500 count data received via databus 1224. Thus, the 3BT data is used by flow pulse 600 for two purposes: as part of the address for the ROM (in the home embodiment) and as the reference count for the ROM frequency. When Flow Pulse 600 completes the count, it turns on an output via line 1226 to FIR 300.

Flow Initiation and Rezero 300, upon receiving the on signal from Flow Pulse 600 via line 1226, begins the rezeroing cycle. At this time, the analog output voltage from inhalation sensor 100 reflects the no-flow condition because sensor 100 is pneumatically isolated from the patient cannula due to demand solenoid 22 being de-energized. This sensor 100 voltage is converted to a digital value by a digital-to-analog converter contained within FIR 300. This voltage is put in memory by 10 iterations of a successive approximation register, a process which takes about 11 milliseconds. The reference voltage thus stored in memory will be used on the next breath cycle by the comparator as its reference voltage In this way, FIR 300 rezeroes during every breath cycle to produce a reference voltage which is very recent in time which it uses to compensate for any drift of sensor 100 output voltage.

After rezeroing is complete, FIR 300 provides an on output via line 1228 to SCM 400 which enables SCM 400 to re-energize demand solenoid 22. This FIR 300 output signal marks the end of the oxygen pulse shown on graph 1309 of FIG. 13. SCM 400 also turns on output via line 1218 to 3BT 500, but the Blanking 700 signal via line 1222 is still off which prevents 3BT 500 from advancing to the next timer. Blanking 700 disables 3BT 500 via the off status on line 1222. This is done because at the end of the oxygen pulse, patient nasal vacuum still exceeds 0.04 cm. water and the comparator of FIR 300 turns off when sensor 100 is pneumatically reconnected as demand solenoid 22 is re-energized. Blanking 700 output via line 1222 goes on at the end of the blanking time which occurs well into the exhale portion of the patient breath cycle, but by this time the comparator output of FIR 300 is off and no triggering will occur until the patient next inhales. Upon the next inhale, the cycle described above repeats and continues to do so indefinitely thereby providing a pulse of oxygen near the beginning of the inhalation portion of every breath cycle.

Seek/Deliver 1100 is activated upon detection of an abnormal patient breath rate—for example, below 8 or above 22 breaths per minute. Seek/Deliver 1100 receives inputs from Clock and Monitor 200 via line 1206, Reset 800 via line 1212, and 3BT 500 via databus 1224 and produces an output to SCM 400 via line 1230. Seek/Deliver 1100 compares the count data received from 3BT 500 with an internal reference count. If the 3BT 500 count is less than the reference, which indicates a high breath rate, then Seek/Deliver 1100 turns on its output for $7\frac{1}{2}$ seconds. Additionally, Seek/Deliver 1100 uses an internal $7\frac{1}{2}$ second pulse count timer which begins its timing cycle after the receipt of a signal from Reset 800 via line 1212 indicating that a valid inhalation has occurred. If another reset signal is not received prior to timing out $7\frac{1}{2}$ seconds, which circumstance indicates a breath rate below 8 per minute, then Seek/Deliver 1100 turns on the output to SCM 400.

The output on signal to SCM 400 causes it to de-energize both solenoids 22 and 24 for $7\frac{1}{2}$ seconds thereby delivering continuous oxygen to the patient during this time. At the end of this 7½ second delivery time, Seek/Deliver 1100 returns to the seek mode and again determines patient breath rate. Seek/Deliver continues cycling in this way indefinitely; however, at the end of 97.5 seconds without a valid inhalation signal (the 97.5 seconds is determined by use of another internal timer), Seek/Deliver 100 activates Audible Alarm 1000 via output line 1232. Additionally, Seek/Deliver 1100 provides an output over line 1232 to Failure Indicator 900 which illuminates a light emitting diode whenever Seek/Deliver 1100 is activated. A signal from Reset 800 via line 1234 to Audible Alarm 1000 and Failure Indicator 900 resets Audible Alarm 1000 and Indicator 900 whenever a valid inhalation is detected.

Seek/Deliver 1100 also incorporates a 20 second warm-up feature which prevents energizing of solenoids 22 and 24 for this amount of time after power-up. This is to allow the electronic components to stabilize before the system goes on-line.

The purpose of the foregoing discussion is to give a simplified, non-rigorous overview of the functioning of the primary modules of the control circuitry 1200. As such, the FIG. 12 block diagram does not show all of the interconnections between components nor does the above discussion explain all of the functions of the various components. A detailed description and discussion is provided below in Part II.B.

B. Detailed Description of the Electrical Circuitry

The electrical circuits described below are designed to be powered by a conventional direct current power supply (not shown) capable of supplying 12 V.D.C., 8 V.D.C., and 5 V.D.C. In the drawings and discussion the symbol $V_{DD}$ stands for 5 V.D.C. and the symbol $V_{EE}$ stands for +8 V.D.C.

Additionally, the circuits described below are of two types—analog and digital. For example, Inhalation Sensor 100 shown in FIG. 1 is an analog circuit. Flow Initiation and Rezero 300 of FIG. 3 includes both analog and digital components which are explained in detail below.

Preferred values of resistors and capacitors are indicated in parentheses when the resistor or capacitor is first mentioned, when the "K" value refers to thousand ohms, and "pf" refers to picofarads. The circuits of FIGS. 2, 4, 5, 6, 7, 8, 9, and 10, and 11 are digital circuits. The digital circuits operate at +5 V.D.C. and when a particular output, input or signal is described as being "on" at a state of "one", or "high", this means +5 V.D.C. When the expressions "off", state of "zero", or "low" is used, this means 0 V.D.C. A system ground in common use throughout is designated by the appropriate symbol and the numeral "6".

The digital circuits described below are designed for incorporation on one or more semiconductor chips by the use of conventional techniques using conventional masking cells for gates and memory elements. As such, the particular circuit elements such as AND, OR, NAND, NOR gates, inverters, flip-flops, counters and so forth are conventional devices well known in the art and are represented by conventional symbols The fact that certain circuits are designed or designated as digital or analog is not to be considered as a limitation but rather as the preferred embodiment of the present invention for reasons including economics, size, power efficiency, and reliability.

1. FIG. 1, Inhalation Sensor 100

Inhalation Sensor 100 includes pressure sensor 102 which is a conventional device such as type 176PC14HD22 supplied by Microswitch Corporation. Pressure sensor 102 includes the following pneumatic components: diaphragm chamber 104, silicon diaphragm 106, restrictor 108, and pneumatic tubes (dotted lines), 110, 112, 114, and 116. Tubes 110 and 112 pneumatically interconnect one side of restrictor 108 with one side of diaphragm 106 at chamber 112, and both are also interconnected via tube 118 to three-way demand solenoid 22. Tubes 114 and 116 pneumatically interconnect the other side of restrictor 108 with the other side of diaphragm 106 at chamber 104, and both also interconnect via tube 120 to ambient air. The balance of the pneumatic arrangement includes oxygen source 18 connected with flow solenoid valve 20 by representative tube 19, representative tube 21 connects valves 20 and 22, and the patient cannula 26 is connected via line 24 to valve 22 as shown. (See part I above for a detailed description of the pneumatic system, discussion here is for the limited purpose of electrical description). When electrical line 415 energizes the coil of valve 20, valve 20 shifts from the prescription flow orifice to the appropriate high flow orifice (see pneumatic description of part I above). When valve 22 is de-energized, oxygen from source 18 flows via tube 19 through valve 20 and via tube 21 through valve 22 and tube 24 to cannula 26. In the de-energized position, valve 22 blocks tube 118. When valve 22 is energized via line 415, tube 21 is blocked and ambient air communicates with cannula 26 via tubes 120 and 114, restrictor 108, tubes 110 and 118, valve 22 and tube 24.

Diaphragm 106 includes a Wheatstone bridge arrangement (not shown) with null and temperature compensation which is implanted on diaphragm 106 by ionization. Power is supplied to the bridge at 8 V.D.C. by line 122 from $V_{EE}$. Another point of the bridge is grounded by line 124 and ground 6. The output from the bridge exits pressure sensor 102 via lines 126 and 128.

In typical use, the prongs of cannula 26 are inserted in the patient's nostrils. Valve 20 is energized and valve 22 is de-energized allowing ambient air communication with cannula 23. When the patient inhales, the nasal vacuum causes the air to flow toward the patient through restrictor 108. The differential pressure created by the air flow through restrictor 108 is transmitted to opposite sides of diaphragm 106 via tubes 110 and 112, and tubes 114 and 116. Because of the direction of the inhale airflow, the lower side (at tube 116) of diaphragm 106 receives the higher pressure and distorts slightly upwardly. This distortion of diaphragm 106 also distorts the resistors of the Wheatstone bridge implanted thereon which thereby changes the resistance value of one or more the resistors on the bridge. This change in resistance value changes the output voltage across lines 126 and 128. When the patient exhales, restrictor 108 airflow reverses as the distortion of diaphragm 106. Similarly, the bridge resistors also distort, changing the resistance thereby, and causing a corresponding output voltage change across lines 126 and 128.

· The remaining electrical components of inhalation sensor 100 provide the means to reference and scale the output voltages of pressure sensor 102 to usable values so that, in this preferred embodiment, the output of inhalation sensor 100 nominally ranges from +4.0 V.D.C. at maximum patient exhalation to +1.0 V.D.C. at maximum patient inhalation with a mid-range value of +2.4 V.D.C. when there is no flow through restrictor 108. To accomplish this result, sensor 102 outputs via lines 126 and lines 128 are coupled to the positive inputs of conventional operational amplifiers 130 and 132 respectively. Amplifier 130 is biased at +8 V.D.C. via line 122 and amplifier 132 is biases to ground 6 via line 134. Amplifier 130 provides an output via line 186 to one side each of resistors 138 (100K) and 140 (499K.). The other side of resistor 138 provides feedback to the negative input of amplifier 130 via line 142 to determine amplifier 130 gain and also couples with one side of resistor 144 (16.2K).

Amplifier 132 provides an output via line 146 to one side of each of resistors 148 (100K) and 150 (499K). The other side of resistor 148 provides feedback to the negative input of amplifier 132 via line 152 to determine amplifier 32 gain and also couples with the other side of resistor 144. Resistor 144 is chosen to have a value which will give the desired differential of the output span of inhalation sensor 100.

The outputs of amplifiers 130 and. 32 are scaled through resistors 140 and 150 respectively and are connected via lines 154 and 56 respectively to the negative input and the positive input respectively of amplifier 158. Amplifier 158 is biased from $V_{EE}$ at +8 V.D.C. via 62.

Resistors 164 (10K) and 166 (4.22K) interconnected by line 168 to form a voltage divider network coupled between lines 160 and 134. The voltage produced by this divider at line 168 is coupled to and through resistor 170 to line 156 to bias the positive input of amplifier 158.

The output of amplifier 158 is transmitted via line 172 to resistor 174 and output terminal 176. The other side of resistor 74 provides feedback to the negative input of amplifier 158 by connection with line 154. The output of the module 100 at terminal 176 is lowest (about 1.0 V.D.C.) when patient inhalation is at a maximum and highest (about 4.0 V.D.C.) when patient exhalation is at a maximum.

The purpose of the particular inhalation sensor described above is to provide information concerning the breath cycle of the patient and is preferred for many reasons including sensitivity, reliability, cost and so forth. One skilled in the art will readily appreciate that other devices would perform equivalently. For example, the particular device could be used in a pressure sensing configuration by dead-ending line 118 at chamber 104 and eliminating restrictor 108. Also, for example, a "hot-wire" anemometer could be used in place of device 102 to provide patient breath cycle data.

2. FIG. 2, Clock and Monitor 200

Clock and Monitor 200 includes oscillator 201, clock monitor 202 and clock 203. Oscillator 201 is a conventional Colpitts oscillator with a ceramic oscillating element which generates a 4 megahertz square wave signal between 0 and +5 volts D.C. having a 50% duty cycle. The signal from oscillator 201 is transmitted to clock monitor 202 and clock 203 via line 204.

Clock and monitor 202 includes two conventional three-state devices 205 and 206 which in the application herein provide for rapid switching operations because of their characteristics of providing a low input impedance when enabled and a high input impedance when not enabled. Each device 205 and 206 receives a constantly on supply voltage $V_{DD}$ via line 207. Device 205 receives the 4 megahertz signal from oscillator 201 via line 204 at its operating enable [OE] terminal.

When device 205 receives the +5 V.D.C. (i.e. "up" or "on") portion of the 4 megahertz square wave received Via line 204 at the OE terminal, supply voltage is transmitted from line 207 through to the output of device 205. When the input at OE is off, the output of device 205 is off. The output from device 205 is transmitted via line 208 to capacitor 209 (33 pf.), the other side of which is connected to ground 6 via line 210, to resistor 211 (100K), the other side of which is connected to ground 6 via line 212, and to Schmitt-trigger NAND gate 213. Device 205 charges capacitor 209 when the output of device 205 is on during the on portion of the oscillator signal. When device 205 is off during the off portion of the oscillator signal, capacitor 209 discharges through resistor 211. The values of capacitor 209 and resistor 211 are chosen such that the exponential decay of capacitor 209 through resistor 211 during the time device 205 is off does not fall below the trigger level of NAND 213 (assuming a normal, as designed, oscillator signal).

The operation of three state device 206 is similar to that of device 205 except that the OE terminal of device 206 is supplied with the oscillator signal via inverter 215 and line 204. Because of inverter 215, device 206 is exactly out of phase with device 205 so that the output of device 206 is on during the off portion of the oscillator signal and is on during the off portion of the oscillator signal. The output from device 206 is transmitted via line 216 to capacitor 217 (33 pf.), the other side of which is coupled to ground 6 via line 218, to resistor 219 (100K), the other side of which is coupled to ground 6 via line 220, and to the second input to NAND 213. The output from device 206 charges up capacitor 217 during the off portion of the oscillator signal. Device 206 is off during the on portion of the oscillator signal and during this time capacitor 217 discharges through resistor 219 to ground. Capacitor 217 and resistor 219 have the same values as capacitor 209 and resistor 211 respectively and the exponential decay of capacitor 217 through resistor 219 is such that normally the value does not fall below the Schmitt-trigger value of NAND 213.

During normal operation, the output of NAND 213 is normally off because the inputs via lines 208 and 216 never fall below the Schmitt-trigger value of about 3 V.D.C. However, if an abnormality would develop in the signal from oscillator 201, one or the other of the inputs via lines 208 and 216 to NAND 213 will go off. For example, if the oscillator fails so that its output is continually on and not oscillating anymore, then the output from device 206 will be off, and NAND 213 will be on. If for example the signal from oscillator 201 goes off and stays off, then the output from device 205 will be off and the output from NAND 213 will then be on. If the oscillation frequency of oscillator 201 decreases significantly capacitors 209 and 217 will discharge through resistors 211 and 219 respectively to values below the Schmitt-trigger level of NAND 213 before being charged up again and the output from NAND 213 will go on. If the oscillation frequency of oscillator 201 goes too high, capacitors 209 and 217 will not become sufficiently charged and their value will decrease during discharge through resistor 211 and 219 respectively to values below the. Schmitt-trigger value of NAND 213. Thus, any number of abnormalities in the signal from oscillator 201 will cause the output from NAND 213 to turn on. The output from NAND 213 is transmitted via line 221 to output terminal 222.

Clock 203 is designed to provide a widerange of specific outputs to supply the various subcircuits. This result is accomplished by scaling the 4 megahertz signal from oscillator 201 through various pulse counter circuits For the sake of clarity, the following discussion assumes that all counters have been initially reset at the "R" terminal on each.

The Clock 203 first performs a division by 2 on the 4 megahertz signal from oscillator 201 received over line 204. This is accomplished using a conventional "D" flip-flop with reset 223. Flip-flop 223 includes clock terminal C, data terminal D, reset terminal R, and output terminals Q and $\bar{Q}$. Flip-flop 223 receives a reset signal at R via line 224. $\bar{Q}$ is connected to D via line 225 and flip-flop 223 produces its output at Q. Flip-flop 223 receives the 4 megahertz square wave signal from oscillator 201 via line 204 at terminal C. Initially, Q is off and $\bar{Q}$ is on. At the first clock pulse at C, Q goes on by virtue of the on signal received at D ($\bar{Q}$ being on when Q is off and vice versa) and $\bar{Q}$ goes off. At the second clock pulse at terminal C, Q goes off because of the off signal at terminal D. At this time $\bar{Q}$ goes on and flip-flop 223 is back to its initial state. This cycle continues so that Q goes on with every other input pulse received at terminal C. In this way flip-flop 223 performs a scale division by 2 of the input received at C and the output of flip-flop 223 at Q is a 2 megahertz square wave signal with a 50% duty cycle.

Conventional "D" flip-flop with reset 226 also performs a division by two scaling operation. Flip-flop 226 includes clock terminal C, data terminal D, reset terminal R, and output terminals Q and $\bar{Q}$. Flip-flop 226 receives the 2 megahertz output from flip-flop 223 via line 227 at terminal C and can receive a reset signal at the same as that of flip-flop 223, flip-flop 226 performs a division by two scaling operation so that the two megahertz signal received at terminal C is scaled to produce a one megahertz 50% duty cycle output at terminal C of flip-flop 226. This output is transmitted via line 229 to counter 230.

Counter 230 in combination with NAND gate 231 scales the one megahertz signal from flip-flop 226 down to a 100 kilohertz downpulse square wave signal. Counter 230 is a conventional binary decade counter which automatically resets itself to zero upon reaching a binary count of decimal ten. Counter 230 includes enable terminal EN, clock terminal C, reset terminal R, least significant bit terminal $Q_0$, and most significant bit terminal $Q_3$ (Terminals for bits $Q_1$ and $Q_2$ are not shown.) A continuously on enable signal is received at terminal EN via line 207 which is supplied by $V_{DD}$ A reset signal can be received at terminal R via line 224. The one megahertz square wave signal from flip-flop 226 is received at terminal C via line 229. Counter 230 provides outputs at terminals $Q_0$ and $Q_3$ via lines 232 and 232a respectively to NAND gate 231. In operation, counter 230 starts with bits $Q_0$-$Q_3$ at a state of zero. The output from NAND 231 is on and stays on until a count of nine is registered on counter 230. Upon reception of the ninth clock pulse at C, bits $Q_0$ and $Q_3$, representing a binary count of decimal nine, both go on and NAND 231 output goes off. At the tenth input clock pulse, counter 230 resets all bits back to zero and NAND 231 output goes on. The cycle then repeats with NAND 231 output going off during one input pulse out of every ten. Thus, the incoming one megahertz square wave signal is converted to an output signal via line 233 to a 100 kilohertz down-pulse square wave signal with a 10% duty cycle. This 100 kilohertz signal is transmitted to counter 234 and inverter 235 via line 233. Inverter 235 converts the incoming signal to a 100 kilohertz up pulse with a 10% duty cycle which is transmitted via line 236 to output terminal C5.

Counter 234 in combination with NAND gate 237 scales its incoming 100 kilohertz signal to a 10 kilohertz signal. Counter 234 is identical to counter 230 and includes terminals EN, C, R, $Q_0$, and $Q_3$ Terminals $Q_1$ and $Q_2$ are not shown. Counter 234 receives a continuously on enable signal at terminal EN via line 207. Counter 230 can receive reset input at terminal R via line 224 and receives the 100 kilohertz downpulse signal via line 233 at terminal C. NAND 237 receives inputs from $Q_0$ and $Q_3$ via lines 238 and 238a respectively. Counter 234 operates on the rising edge of the input signal received at C and adds one binary count each time an arriving pulse is received at terminal C. As with counter 230, 234., $Q_0$ and $Q_3$ go on only when a count of nine is registered. Upon the tenth pulse received at terminal C all bits of counter 234 are reset to zero. The output of NAND 237 is thus a ten kilohertz downpulse with a 10% duty cycle. This output is transmitted via line 237a to counter 239, terminal C6, and inverter 237b. Inverter 237b converts the incoming signal to a ten kilohertz up pulse signal with a 10% duty cycle which is transmitted to terminal C7 via line 240.

Counter 239 is a binary decade counter identical to 230 and 234 but with which the outputs from all four bits are used. Counter 239 includes enable terminal EN, clock input terminal C, reset terminal R, and output bit terminals $Q_0$, $Q_1$, $Q_2$, and $Q_3$ with bit $Q_0$ being the least significant bit and $Q_3$ being the most significant bit. Counter 239 receives a continuously on enable signal at terminal EN via line 207, can receive a reset signal in terminal R via line 224, and receives the ten kilohertz signal from NAND 237 at terminal C. Counter 239 provides outputs at $Q_0$, $Q_1$, $Q_2$, $Q_3$, via lines 240a, 240b, 240c, and 240d, respectively. The output of $Q_0$ via line 240a is transmitted to inverter 241a and NAND gate 242. The output of $Q_1$ is transmitted via line 240b to AND gate 243a, inverter 241b, and to AND gate 243c. The output of terminal $Q_3$ is transmitted via line 240d to AND 243d and AND 242. The output of inverter 241a is transmitted via line 244a to AND 243a, AND 243b, AND 243c, and AND 243d. The output from inverter 241b is transmitted via line 244b and AND 243b. The output from inverter 241c is transmitted via line 244c to AND 243a. The outputs from AND gates 243a-d are transmitted via lines 245a, b, c, and d respectively to terminals C1, C2, C3, and C4, respectively.

The purpose of counter 239 along with inverters 241a-c and AND gates 243a-d is to provide a series of non-overlapping one kilohertz up pulse signals. Counter 239 counts the incoming ten kilohertz downpulses received at terminal C. The pulse count is represented in binary at terminals Inspection of the connections of AND 243a reveals that it provides an on output to terminal C1 only when its three inputs are on, and this occurs only when a count of two exists on counter 239. That is, the output to terminal C1 is only if $Q_0$ is off, $Q_1$ is on, and $Q_2$ is off. In four bit binary these conditions also would be satisfied at a decimal count of 12, but because binary decade counter 239 resets itself upon reaching a count of ten, these conditions are never reached, and thus C1 only comes on a count of two, which occurs once every ten input pulses at terminal C.

By similar analysis, the output at C2 is on only when a count of four exists on counter 239, that is when $Q_0$ and $Q_1$ are off and $Q_2$ is onl. A count of for exists for only one pulse duration out of every ten in the operation of counter 239. Thus the output of C2 is on only for one pulse width out of every ten.

The output at terminal C3 is on only when a count of six exists on counter 239. That is, when $Q_0$ is off and $Q_1$ and $Q_2$ are on.

The output at C4 is on only if a count of 8 exists on counter 239. That is, when $Q_0$ is off and $Q_3$ is on. When $Q_0$ comes back on at a count of nine, AND 243$d$ is no longer satisfied and C4 is off. Thus as with terminals C1, C2, and C3 the output at C4 is on only for one incoming pulse duration out of every ten. The overall effect of this arrangement is that a one kilohertz up pulse square wave output exists at terminal Cl, C2, C3, and C4 with 10% duty cycles, but these outputs are non-overlapping.

The output from NAND 242 is off only if a count of nine exists on counter 239. At all other pulse counts the output from NAND 242 is on. Thus the output of NAND is a one kilohertz downpulse with a 10% duty cycle. This output is transmitted via line 246 to counter 247, terminal C8 and inverter 248. Inverter 248 converts the incoming one kilohertz downpulse signal to a one kilohertz up pulse signal which is transmitted to terminal C9 via line 249.

Counter 247 is identical to counters 230 and 234 and is used in the same way to scale by a factor of ten the incoming one kilohertz downpulse to a 100 hertz output downpulse. Counter 247 receives a continuously on enable signal via line 207 at terminal EN, can receive reset signal at terminal R via line 250 from terminal 840, and receives the one kilohertz downpulses from NAND 242 at terminal C via line 246. Terminals $Q_0$ and $Q_3$ are connected to NAND 251 via lines 252 and 252$a$ respectively. Terminals $Q_0$ and $Q_3$ are both on only when a count of nine exists on counter 247 which occurs only once every ten input cycles as with counters 230 and 234. Thus the output from NAND 251 is a 100 hertz square wave downpulse signal with a 10% duty cycle. The output from NAND 251 is transmitted via line 253 to counter 254, output terminal C10 inverter 255, inverter 256 and counter 257. Inverter 255 converts the incoming 100 hertz down pulse signal from NAND 251 to a 100 hertz up pulse signal which is delivered to terminal C11 via line 258.

Counter 254 is identical to counters 230, 234, and 247 and is used in the same way to scale the incoming clock pulse by a factor of ten Counter 254 receives a continuously on enable signal via line 207 at terminal EN, receives a 100 hertz clock signal from NAND 251 at terminal C, and can receive a reset signal at terminal R from OR gate 259 via line 260. OR gate 259 receives its first input via line 250 from terminal 840 and the second input via line 261 from terminal 347.

Outputs from $Q_0$ and $Q_3$ of counter 254 are transmitted to NAND 262 via lines 263 and 263$a$ respectively. The output from NAND 262 is off only when the count of nine exists on counter 254. Thus the output of NAND 262 is a ten hertz square wave downpulse with a 10% duty cycle which is transmitted via line 264 to terminal C15 and inverter 265 Inverter 265 converts the 10 hertz downpulse signal to a ten hertz up pulse signal to terminal C12 via line 266.

The next clock scaling circuit is designed to convert 100 hertz downpulses to 10 hertz up pulses at terminal C13. Input 100 hertz downpulses delivered to inverter 256 are converted to 100 hertz up pulses and transmitted via line 267 to counter 268 and inverter 269.

Counter 268 is a conventional eight bit Johnson counter and includes enable terminal CE, reset terminal R, clock terminal C, and output bit terminal $Q_5$. (Terminals for bits $Q_0$, $Q_1$, $Q_2$, $Q_3$, $Q_4$, $Q_6$, and $Q_7$ are not shown.) Terminal CE is clamped to ground 6 via line 268A which by means of an internal inverter continuously enables counter 268 to count input pulses. Incoming 100 hertz up pulses are received at terminal C via line 267. At the fifth incoming clock pulse at terminal C, $Q_5$ goes on which output is transmitted via line 270 to terminal C13 and NAND 271.

Inverter 269 converts the 100 hertz up pulse signal received via line 267 to a 100 hertz downpulse signal which it transmit via line 272 to NAND 271. NAND 271 output goes off when $Q_5$ is on and a the end of incoming clock signal via line 272 when the signal goes back on. When both inputs to NAND 271 are satisfied, NAND output 271 goes off which output is transmitted via line 273 to NAND 274. The other input to NAND 274 is received via line 275 from terminal 838. The input from terminal 838 is normally on except when a reset condition exists. The output from NAND 274 is transmitted to R of counter 268 via line 276. When the input to NAND 274 via line 273 goes off, the output from NAND 274 goes on and resets counter 268. As soon as counter 268 is reset, $Q_5$ goes off, NAND 271 is no longer satisfied and its output goes on to NAND 274. At this point both inputs to NAND 274 are on and the output of NAND 274 goes off to remove the reset signal from R of counter 268. This cycle repeats continually so that $Q_5$ comes on for one input pulse cycle duration out of every five received at terminal C and the incoming 100 hertz signal is thus scaled to a 20 hertz up pulse signal with a 20% duty signal which is delivered via line 270 to terminal C13.

The last scaling circuit in clock 203 converts the 100 hertz downpulses from NAND 251 to up pulses at approximately 4.16 hertz at terminal C14. The final scaling process starts with conventional eight-bit Johnson counter 257 f which includes clock enable terminal CE, reset terminal R, clock input terminal C, bit output terminal $Q_0$, and bit output terminal $Q_7$. Output terminals for bits 1, 2, 3, 4, 5, and 6 are not shown. Divider 257 receives 100 hertz downpulses 257 is reset with all bits except $Q_0$ at zero and the input to CE via line 276 is off; by means of internal inverter, divider 257 is enabled to count incoming clock pulses when CE input is off. At the first clock pulse input, $Q_0$ goes off which output is transmitted via line 277 to reset divider 278. Divider 257 continues to clock through clock pulses and upon receiving the seventh clock pulse, $Q_7$ goes on which output is transmitted via line 276 to terminal CE and to AND gate 279. The other input to AND 279 is the 100 hertz downpulse signal received via line 253. As soon as this clock signal goes back on, which is the end of the pulse, then both inputs to AND 279 are on and the output of AND 279 goes on, which output is transmitted via line 280 to divider 278. When $Q_7$ of divider 257 goes on, this disables divider 257 via line 276 to terminal CE and causes it to hold the $Q_7$ output on.

Divider 278 is identical to divider 257 and is likewise a conventional eight-bit Johnson counter. Divider 278 includes enabling terminal CE, reset terminal R, clock input terminal C, and sixth bit output terminal $Q_6$. (Terminals for bits $Q_1$, $Q_2$, $Q_3$, $Q_4$, $Q_5$, and $Q_7$ are not shown.) Terminal CE is clamped to ground 6 via line 281 and thus continuously enabled. Terminal R can receive a reset input via line 277 from terminal $Q_0$ of divider 257. Terminal C receives its input via line 280 from AND 279.

Clock pulses received by AND 279 via line 253 transmit on through AND 279 because the other input to AND 279 is from $Q_7$ of divider 257 which is held on until divider 257 is reset later in the sequence. The clock pulses passing through AND 279 via line 280 are received at terminal C of divider 278 when $Q_7$ of divider 257 goes on. Upon reception of the sixth rising edge clock pulse by divider 278, terminal $Q_6$ goes on. This on output from $Q_6$ is transmitted via line 282 to flip-flop 283 and to NAND 284.

Inverter 285 receives clock pulses via line 253 and upon reception of the very next off pulse, the output of inverter 285 goes on which output is transmitted to NAND 284 via line 286. At this point both inputs to NAND 284 are on and NAND 284 output goes off. The off output of NAND 284 is received by NAND 287 via line 288 The other input to NAND 287 is an input from terminal 838 via line 275 which is normally on unless a reset condition exists. Because the output to NAND 287 via line 288 is off, the output of NAND 287 goes on to reset terminal R of divider 257 via line 289. With divider 257 thus reset, $Q_7$ goes off which removes the signal from terminal CE and enables divider 257 to again count clock pulses. Also, when $Q_7$ goes off, AND 279 goes off and divider 278 no longer receives clock pulses and $Q_0$ of divider 257 goes on to reset divider 278.

The interconnections described above effectively interconnect dividers 257 and 278 into a 12 bit divider so that an output from $Q_6$ of divider 278 occurs once for every 12 pulses of the 100 hertz signal received by divider 257.

Flip-flop 283 is a conventional "D" type flip-flop with reset and is used to scale the incoming signal by a factor of two and is identical to flip-flops 223 and 226 which were used for the same purpose. Flip-flop 283 can receive a reset signal via line 290 from inverter 291 which receives its input via line 275 from input terminal 838. Because of inverter 291, the reset signal on line 290 is normally off unless a reset condition exists. Terminal C receives its input via line 282 from terminal $Q_6$ of divider 278. Terminal D receives its input via line 292 from terminal $\overline{Q}$. Terminal Q provides its output via line 293 to terminal C14 and flip-flop 283 scales the incoming clock pulses received at C by a factor of two. Dividers 257 and 278 as combined with flip-flop 283 scale the incoming 100 hertz downpulses by a factor of 24 so that the output at terminal C14 is at a frequency of 4.16 hertz with a 50% duty cycle.

3. FIG. 3, Flow Initiation and Rezeroing 300

Flow Initiation and Rezeroing module 300 broadly includes rezeroing section 301 and flow initiation section 302. The broad function of flow initiation 302 is to detect patient inhalation, validate that inhalation, and provide an output signal when a valid inhalation is detected.

Flow Initiation 302 begins its function with comparator 306 which is a conventional differential operational amplifier having a positive input terminal (+), negative input terminal (−), and an output. Comparator 306 receives a positive input signal via line 308 from terminal 176 which is the output from inhalation sensor 100. Comparator 306 receives a negative input from digital-analog converter [DAC] 310, which is part of rezeroing section 304, via line 312. The output from DAC 310 via line 312 is a reference voltage equal to the voltage output of inhalation sensor 100 at terminal 176 during the previous breath cycle when solenoid valve 22 was de-energized and no air flow was occurring through restrictor 108. When the positive terminal input voltage is greater than the negative terminal input voltage to comparator 306, then comparator 306 output is on. This is the status existing when patient inhalation is not occurring, that is, when the patient is exhaling, at pause, or when the patient's inhale nasal vacuum is less that 0.04 cm. water. When the positive terminal input voltage is less than the negative terminal input voltage, then the output of comparator 306 is off. This situation exists when the patient is inhaling and nasal vacuum exceeds 0.04 cm. water. Comparator 306 is used in a "negative trigger" mode so that patient inhalation causes comparator 306 output to go off, which triggers the remainder of flow initiation section 302.

Comparator 306 output is biased in order to provide a proper digital voltage. This is accomplished by supplying one side of resistor 314 (100K) with biasing voltage $V_{DD}$ (+5 V.D.C.) via line 316. The other side of resistor 314 is connected via line 318 to inverter 320 and the resistor 322 (1K). The resistor 322 is connected via line 324 to the output of comparator 306.

When comparator 306 output is on (indicating no inhalation is occurring), then the output of inverter 320 is off, which output is transmitted via line 326 to serial register 328 and inverter 330. Because the input to inverter 330 is off, its output is on via line 332 to OR gate 334. By virtue of the on input via line 332, OR 334 output is on via line 335 to the reset terminal R of register 328. Thus, lack of patient inhalation causes a continuous on signal to hold register 328 in a reset condition.

When inhalation occurs (i.e., when patient nasal vacuum exceeds 0.04 cm. water), comparator 306 output goes off, inverter 320 output goes on, and inverter 330 output goes off, which removes the reset signal from register 328. Also when inverter 320 output goes on, terminal D of register 328 receives this on signal via line 326.

Register 328 is a conventional ten bit serial register which successively transfers input data from the first to the last bit with each incoming clock pulse. Register 328 includes data input terminal D, reset terminal R, clock input terminal C, and tenth bit output terminal $Q_9$. Output terminals for bits $Q_0$ through $Q_8$ are not shown because they are not used. Terminal C receives one kilohertz up pulses from terminal C9 via line 336.

The purpose of register 328 is to provide a ten millisecond delay upon the occurrence of patient inhalation to insure that the inhalation signal is not a spurious event; the ten millisecond delay thereby validates inhalation detection. The clock pulses received at terminal C occur at a rate of one per millisecond and the on data signal received at terminal D thereby clocks through the ten bits at a rate of one per millisecond so that after ten milliseconds $Q_9$ goes on. If at any time during the ten milliseconds comparator 306 output goes on, then register 328 will receive a reset signal at R via inverters 320 and 330 and OR 334 which occurrence resets all the bits of register 328 thereby preventing any output signal at $Q_9$.

If comparator 306 output is off for the required ten milliseconds, then, at the end of this time, $Q_9$ goes on to provide an input to AND 337 via line 338. At this point in the cycle, inverter 339 output is on via line 340 to AND gate 337, and AND 337 output goes on via line 341 to "S" flip-flop 342.

Conventional "S" flip-flop with reset 342 includes reset terminal R, data set terminal S, and output terminal Q ($\bar{Q}$ is not shown because it is not used). When terminal S receives an on input via line 341, then Q goes on, which output is transmitted via line 343 to output terminals 344, 345, 346, and 347.

When the Q on output from flip-flop 342 is detected by Three Breath module 500 via Solenoid Control module 400, Three Breath 500 turns off its output to terminal 506 which is transmitted via line 349 to "D" flip-flop 350 of flow initiation 302. (The details of this feedback from Three Breath 500 will be explained in detail below.) Flip-flop 350 is a conventional "D" type flip-flop with set and reset and includes data input terminal D, set terminal S, clock input terminal C, and output terminal Q ($\bar{Q}$ is not shown). Terminal C receives one kilohertz downpulse clock signals from terminal C8 via line 351. The trailing (rising) edge of the downpulse received at terminal C triggers flip-flop 350 to transfer the off data signal at D to output terminal Q. The initial state of flip-flop 350 is set by an input to terminal S from circuit input terminal 834 via line 353 which also supplies inverter 354.

The off output of flip-flop 350 is transmitted via line 355 to NAND gate 356. The other input to NAND 356 is supplied via line 357 from inverter 354. At this point in the cycle, the input to inverter 354 is off so that the output is on; however, when the input to NAND 356 from flip-flop 350 goes off, the output of NAND goes on which is transmitted via line 358 to flip-flop 342, inverter 339 and OR gate 359. When NAND 356 output goes on this resets flip-flop 342 at terminal R causing output Q to go off, which causes the output from inverter 339 to go off, which causes AND 337 output to go off, and resets register 328 via OR 359, line 360, OR 334, and line 335 to terminal R of register 328.

At this point in the cycle the output of inverter 361 via line 362 to OR 359 is off because the input to inverter 361 received via line 363 is on.

To sum up the operation of flow initiation 302, when sufficient patient inhalation occurs, comparator 306 goes off, which removes the reset signal from terminal R of register 328 at which point it begins clocking through the on data input signal. At the end of ten milliseconds the output from register 328 goes on, which is transmitted through AND 337 to flip-flop 342. The output from 342 is transmitted to various circuit components including the Three Breath module 500, which sends back a signal to turn off flip-flop 350, the off output from which then causes NAND 356 to go on, which resets flip-flop 342 and register 328. The net effect is that the output of flip-flop 342 is a single up pulse.

Rezeroing section 304 performs two main operations. First, DAC 310 supplies a reference voltage via line 312 to comparator 306. Secondly, rezeroing 304 updates its reference signal by putting a new signal in memory for use during the succeeding breath cycle.

Rezeroing 304 includes a conventional ten bit successive approximation register [SAR] 364 SAR 364 includes output data terminals $Q_0, Q_1, Q_2, Q_3, Q_4, Q_5, Q_6, Q_7, Q_8, Q_9$, which correspond to the ten bits of SAR 364, with $Q_0$ being the least significant bit and $Q_9$ being the most significant bit. SAR 364 also includes an end-of-conversion terminal EOC, whose output is on and is applied via line 363 to inverter 361 and output terminal 333 after a successful analog-to-digital conversion has occurred; that is, terminal EOC is normally on except when SAR 364 is undergoing the conversion iterations.

Input terminal SC is the start conversion terminal, which initiates the analog to digital conversion process whenever terminal SC receives an input via line 365. An on signal at terminals 825 or 684 is transmitted via lines 368 and 369 respectively to OR 370, whose output is transmitted via line 371 to OR 372, whose output on line 365 terminates at terminal SC. OR 372 also receives an input from terminal 1158a via line 374.

Terminal OR (overrange) of SAR 364 provides an on signal corresponding to an overrange condition of SAR 364. This overrange signal is transmitted via line 375 to terminal 376 and inverter 377. The output from inverter 377 is transmitted via line 378 to terminal 379.

Non-overlapping one kilohertz up pulse clock signals are received via lines 380a, 380b, 380c, 380d, from terminals C1, C2, C3 and C4, respectively. SAR 364 also includes an input terminal labeled DATA at which SAR 364 receives input data voltage corresponding to the analog voltage to be put in the ten bit memory.

Digital-to-analog converter 310 is a conventional ten-bit type which receives bit data from SAR 364 corresponding respectively to bits $Q_0$-$Q_9$ through lines 381a, 381b, 381c, 381d, 381e, 381f, 381g, 381h, 381i, and 381j respectively. DAC 310 also includes output terminal OUT through which DAC 310 conveys its analog voltage output signal via line 312 to comparator 306.

Rezeroing 304 puts new data in the memory of SAR 364 near the end of each flow pulse. When the Flow Pulse module 600 completes the timing of an oxygen pulse (to be explained in more detail below), Flow Pulse 600 produces an on signal at terminal 684, which signal is received at terminal SC of SAR 364, which starts the conversion process. At this time the output from terminal EOC goes off which prevents solenoid 22 from being de-energized Because solenoid 22 remains energized, no air is flowing through restrictor 108 (FIG. 1) and the output from inhalation sensor 100 at terminal 176 represents a no-flow reference voltage.

Analog comparator 382 (a conventional differential operational amplifier) is central to the conversion process and receives the no-flow voltage signal from inhalation sensor 100 via line 308 at its positive input terminal. Analog comparator 382 receives DAC 310 output via line 312, resistor 383 (27.4 ohms), and line 384 at the negative input terminal. The value of resistor 383 is calculated to bias the DAC 310 output signal so that the value put in SAR 364 memory corresponds to inhalation sensor 100 voltage output signal existing when a patient nasal vacuum is 0.04 cm. water. The negative terminal input voltage to comparator 382 is also biased to a chosen mid-range value by way of voltage $V_{EE}$ (+8V.D.C.) connected via line 385 to resistor 386 (20K). The other side of resistor 386 is connected to the negative input terminal of comparator 382 by line 384.

The output of comparator 382 is biased to provide the proper analog voltage to inverter 387 by applying voltage $V_{DD}$ (+5 V.D.C) via line 388 to resistor 389 (100K) and from the other side of resistor 389 via line 390 to resistor 391 (1K) Resistor 391 is also connected to the output of comparator 382 by line 392. Resistor 389 is also coupled to the input inverter 387 by line 390. The output of inverter 387 is connected via line 393 to inverter 394 whose output is connected via line 395 to the DATA terminal of SAR 364.

When the SAR 364 conversion process begins, data received at the DATA terminal of SAR 364 begins clocking through with each pulse received from terminals C1-4, starting with the most significant bit $Q_9$. The clock pulses received at terminal C1-4 are non-overlapping to insure discrete sequencing of data transmission from one bit to the next. During the conversion process, if the input to the positive terminal of comparator 382 is greater than the input received at the negative terminal, then the comparator is on and via inverters 387 and 394, the DATA input to SAR 364 is one. If the voltage signal received at the positive terminal is less than the voltage received at the negative terminal of the comparator 382, then the DATA input to SAR 364 is a zero. Thus, the greatest output voltage from DAC 310 exists when all bits are one. If the feedback to comparator 382 from DAC 310 is greater than the voltage from inhalation sensor 100 than the data input to SAR 364 for that bit is zero. This sequence continues until all ten bits receive a data input. At this point the analog data is in memory and the EOC terminal goes on signalling the end of conversion, which allows solenoid 22 to re-energize to end the oxygen pulse.

Figure 4:
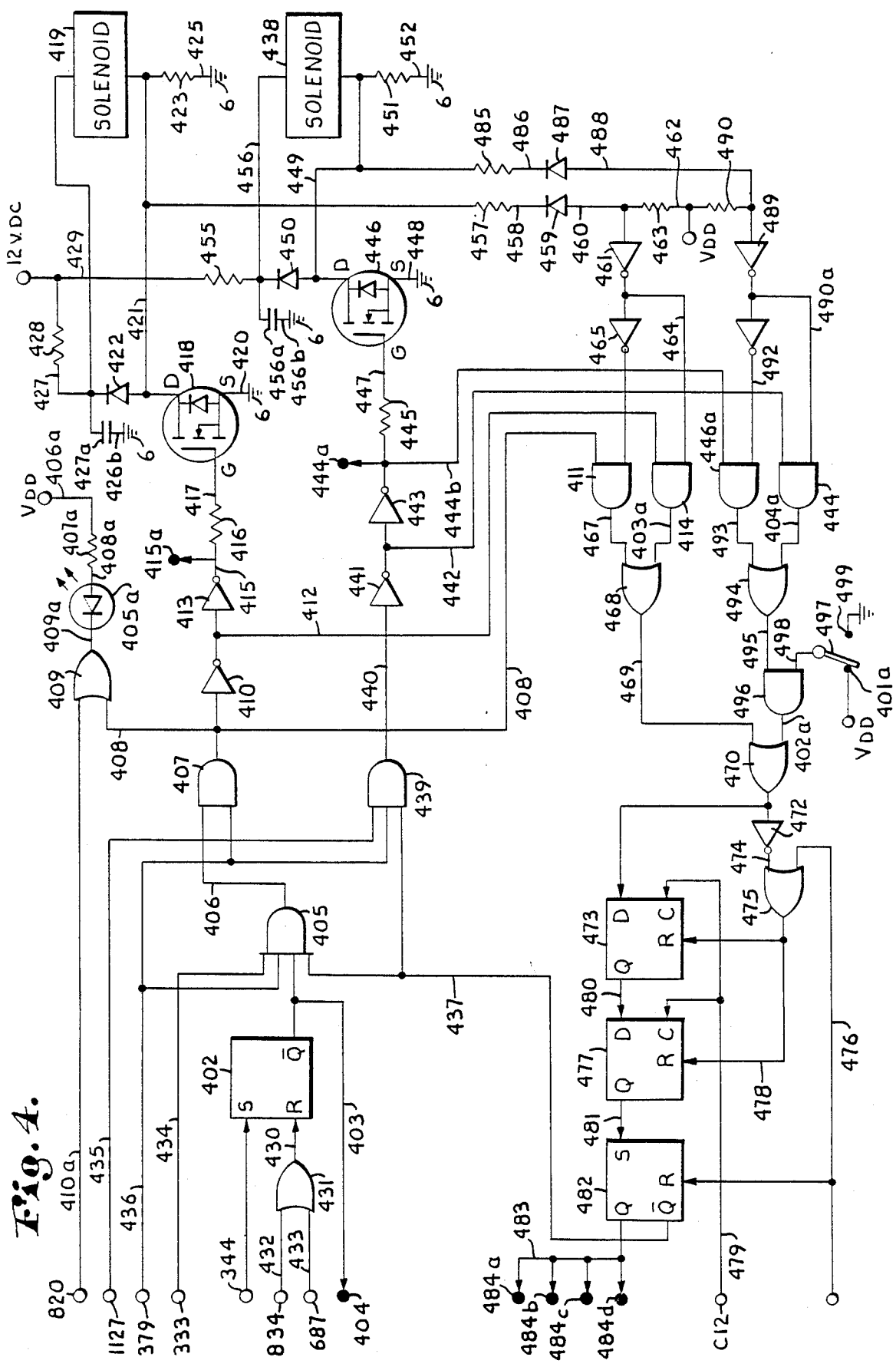
FIG. 4 is an electrical schematic drawing depicting the solenoid control and monitoring circuit of the overall device.

4. FIG. 4, Solenoid Control and Monitor 400

Solenoid Control and Monitor module 400 has two main purposes. The first purpose is to energize and de-energize the solenoid coils of solenoid valves 20 and 22. The second purpose is to monitor the status of the coils in conformity with the control signals and to provide output signals if no abnormality exists. In the hospital use of the present invention two solenoid valves 20 and 22 are used; however, in the home version, solenoid valve 20 is not present. The description that follows in this section is for the more complicated hospital version.

Solenoid Control and Monitor 400 receives a flow initiation signal at terminal 344, which is the output of Flow Initiation and Rezeroing module 300, and which signal indicates that a valid inhalation has occurred. This signal is transmitted via line 401 to flip-flop 402 which is a conventional "S" flip-flop with reset and having a set function terminal S, a reset terminal R, and an output terminal $\overline{Q}$. (Output terminal Q is not shown because it is not used.) When terminal S receives the on signal via line 401, $\overline{Q}$ goes off, which output is transmitted via line 403 to output terminal 404 and AND gate 405. When line 403 goes off, AND 405 goes off via line 406 to AND 407, which output also goes off via line 408 to OR 409, inverter 410 goes off, inverter 410 output goes on via line 412 to inverter 413 and AND gate 414. When the input to inverter 413 goes on, the output from inverter 413 goes off via line 415 to current limiting resistor 416 (100K) and terminal 415a. The other side of resistor 416 is connected via line 417 to the gate of field effect transistor [FET] 418. With the gate to FET 418 de-energized, solenoid coil 419 associated with solenoid valve 22 is de-energized and solenoid valve 22 allows oxygen to flow to the patient.

The source S of FET 418 is clamped to ground 6 via line 420. The drain of FET 418 is connected via line 421 to the anode of diode 422, one side of solenoid coil 419, and resistor 423 (4.02K). The other side of resistor 423 is clamped to ground 6 via line 425.

The cathode of diode 422 is connected via line 427 to the other side of solenoid coil 419, capacitor 427a (68 micro f.) the other side of which is clamped to ground 6 via line 427b, and to current limiting resistor 428 (100 ohms). Operating voltage at 12 V.D.C. is supplied to the other side of resistor 428 via line 429. Diode 422 serves to limit surge current through FET 418 when solenoid coil 419 is de-energized. Capacitor 427a provides a "snap" to quickly energize coil 419.

Briefly then, the reception of an on signal at terminal 344, which indicates that valid inhalation has occurred, causes solenoid coil 419 to be de-energized thus allowing oxygen to flow to the patient. This marks the beginning of the oxygen flow pulse.

Flip-flop 402 keeps $\overline{Q}$ off until a reset signal is received at terminal R via line 430 from OR 431. The output of OR goes on when it receives an on signal via line 432 from terminal : 834 or via line 433 from terminal 687. Terminal 834 is on only if a reset condition exists and is thus normally off. An on signal is received at terminal 687 when Flow Pulse Circuit module 600 completes the timing out of the oxygen pulse. At this time flip-flop 402 receives a reset signal at terminal R and $\overline{Q}$ goes on. However, AND 405 is not yet satisfied because it has not yet received an end of conversion signal from terminal 333 via line 434 indicating that successive approximation register 364 of Flow Initiation and Rezeroing module 300 has completed its conversion of the new analog signal.

The input to AND 405 via line 435 from terminal 1127 is normally on unless an abnormality exists. Similarly, the input via line 437 is normally on also unless an abnormality is detected by the solenoid monitor. Thus, inputs to AND 405 via lines 437, 403, and 435 are on, but the input via line 434 is off until the end of conversion state of shift approximation register 364. When the input via line 434 goes on, AND 405 output goes on to AND 407. AND 407 input via line 440 is normally on from terminal 379 unless an abnormal overrange condition exists on shift approximation register 364. Thus, AND 407 goes on, inverter 410 goes off, inverter 413 goes on, and FET 418 goes on to energize solenoid coil 419. Coil 419 is energized by way of 12 volt supply via line 429, resistor 428, line 427, through coil 419 to line 421, FET 418, line 420, to ground 6.

During operation of the hospital unit, solenoid coil 438 associated with solenoid valve 20 is normally energized to thereby connect the high flow orifice into the pneumatic system. To accomplish this, the output of AND 439 is on because line 405 from terminal 1127 is on unless an abnormal condition exists, line 436 from terminal 379 is energized unless an overrange condition exists oh SAR 364 and line 437 i on unless a solenoid abnormality is detected. The on output from AND 439 is transmitted via line 440 to inverter 441 which output is off via line 442 to inverter 443 and AND 444. The output from inverter 443 is on which is transmitted via line 444b to current limiting resistor 445 (100K), terminal 444a, and AND 446a. The other side of resistor 445 connects to the gate G of field effect transistor [FET] 446 via line 447.

The circuit for energizing solenoid coil 438 is similar to that for energizing solenoid coil 419. The on signal to gate G of FET 446 causes FET 446 to conduct from drain D through to source S and via line 448 to ground 6. Drain D of FET 446 is connected via line 449 to the anode of diode 450, to one side of solenoid coil 438, and to resistor 451 (4.02K) the other side of which is connected to ground 6 via line 452. When FET 446 is conducting, current flows through line 429 from the 12 V.D.C. source through current limiting resistor 455 (100 ohms), then through line 456, coil 438, line 449, FET 446, line 448, to ground 6. Diode 450 is in parallel with coil 438 to protect the FET 446 from surge currents when coil 438 is de-energized. Line 456 also connects to capacitor 456a the other side of which is connected to ground 6 via line 456b; capacitor 456a provides a "snap" to quickly energize coil 438. If any of the inputs to AND 439 go off in the event of an abnormal condition, AND 439 goes off, this by way of inverters 441 and 443 and resistor 445 turns off FET 446. When FET 446 turns off, solenoid coil 438 is de-energized.

The balance of the circuit of Solenoid Control and Monitor module 400 is the monitoring portion which detects a solenoid coil status different from nominal.

For the sake of an example, assume that FET 418 has failed so that an open circuit exists continuously between drain D and source S. Furthermore, assume that the patient is in the exhale portion of the breath cycle, which means that FET 418 is receiving voltage at gate G and that without the failure FET 418 would be conducting to thereby energize solenoid coil 419. With the open circuit on FET 418, a voltage value exists at line 421 by virtue of the circuit connection through resistor 423 and through coil 419, line 427, resistor 428 to the 12 V.D.C. voltage source.

This voltage is transmitted via line 421 to resistor 457 (1K) and from the other side of resistor 457 via line 458 to the anode of diode 459, from the cathode of diode 459 via line 460 to inverter 461. Voltage source $V_{DD}$ provides a proper digital biasing voltage via line 462 and resistor 463 (lOOK) to line 460. Thus by virtue of the open circuit across the drain and source of FET 418, inverter 461 receives an input voltage. Inverter 461 output is off which output is connected via line 464 to inverter 465 and AND 414. Because the input to inverter 465 is off, its output is on via line 466 to AND 411. The other input to AND 411 is on via 408 because the output of AND 407 is on indicating that the solenoid coil 419 should be energized. Thus AND 411 is on via line 467 to OR 468. The on output of OR 468 is transmitted via line 469 to OR 470 whose output is transmitted via line 471 to inverter 472 and flip-flop 473. Because the input to inverter 472 is on, its output via line 474 to OR 475 is off. The other input to OR 475 via line 476 from terminal 828 is normally off unless a reset condition exists. Thus, the output of OR 475 is off which removes a reset signal from flip-flops 473 and 477 via line 478.

Flip-flops 473 and 477 are conventional "D" flip-flops with reset, each having reset terminal R, clock input terminal C, data input terminal D, and output terminal Q. Terminal C of flip-flops 473 and 477 each receive ten hertz up pulse clock pulses from terminal C12 via line 479.

Because of the on input at terminal D of flip-flop 473, terminal Q goes on at the next incoming clock pulse at terminal C. The on output at terminal Q of flip-flop 473 is transmitted via line 480 to terminal D. of flip-flop 477. At the very next clock pulse terminal Q of flip-flop 477 goes on. The use of the two flip-flops 473 and 477 in combination with the ten hertz clock pulses produces a delay of about 200 milliseconds, which is necessary because of the real time delay in the operation of solenoids 419 and 438.

The output from terminal Q of flip-flop 477 is transmitted via line 481 to terminal S of flip-flop 482 which is a conventional "S" type flip-flop with set and reset and includes set terminal S, reset terminal R, output terminal Q, and output terminal $\overline{Q}$. The on signal at terminal S of flip-flop 482 causes terminal Q to go on and $\overline{Q}$ to go off.

When terminal Q of flip-flop 482 goes on, this output is transmitted via line 483 to terminal 484a, 484b, 484c and 484d. The on signal at terminal 484a-d indicates to various circuits (described in detail below) that an abnormal condition exists. When terminal $\overline{Q}$ of flip-flop 482 goes off, the output of AND gates 405 and 439 go off to de-energize both solenoid coil 419 and 438 through the circuitry described above. Because of the open circuit failure of FET 418, solenoid coil 419 is already de-energized.

The operation of the monitor circuitry associated with solenoid coil 438 is very similar to that associated with solenoid coil 419. For the t sake of a second example, assume that FET 446 has 1 failed with a continuous open circuit between drain D and source S and that gate G is receiving a voltage signal indicating that solenoid coil 438 should be energized. The voltage produced across the open circuit of FET 446 and across resistor 451 to ground 6 is transmItted via line 449 to resistor 485 (1K) and from there via line 486 to the anode of diode 487. From the cathode of diode 487 voltage is transmitted via line 488 to inverter 489. Digital biasing voltage is supplied from terminal $V_{DD}$ via line 462 to resistor 490 (100K) and from there to line 488. Resistor 490 in combination with diode 487 bias the analog voltage to the proper digital voltage to provide the proper input to inverter 489.

Because the input to inverter 489 is on, its output is off via line 490a to inverter 491 and AND 444. The on output of inverter 491 is transmitted via line 492 to AND 446a. AND 446a is on because its other input via line 444 is also on because of the on signal from inverter 443. The on output of AND 446a is transmitted via line 493 to OR. 494. The on output from OR 494 is transmitted via line 495 to AND 496.

The second input to AND 496 is supplied from switch 497 via line 498. Switch 497 is selectable between a position at terminal 499 which is clamped to ground 6 or a position 401a which is clamped to voltage $V_{DD}$. When switch 497 is switched to terminal 499 the input to AND 496 by line 498 is off continuously which continuously disables AND 496. The grounded position of switch 497 is selected at the factory when the device is used in the home application. In this application solenoid 20 is not provided and thus there is no need to monitor the status of a nonexistent solenoid coil. However, the circuitry is provided as a matter of manufacturing economics. In the hospital application, solenoid 20 is provided and there is a need to monitor the status of the circuit associated with solenoid coil 438. Thus, in this mode, switch 497 is set at the factory to terminal 401a thus providing a constant on signal via line 498 to AND 496. The switch is shown in the position for the hospital application and thus the on input via line 498 causes AND 496 to go on via line 402a to OR 470. The on output from OR 470 activates flip-flops 482, 477, and 473, as described above.

Another monitoring function also exists. If AND 407 is off indicating that solenoid coil 419 should be de-energized but FET 418 is conducting instead, then a very low voltage exists at line 421. In this situation AND 414 is on because it is receiving a signal via line 412 from inverter 410 and the other input to AND 414 is on via line 464 from inverter 461. The on output from AND 414 is transmitted via line 403a to OR 468. The on output of OR 468 activates flip-flops 482, 477, and 473 as described above.

If a similar abnormality exists associated with solenoid coil 438, then AND 444 is receiving an on input via line 442 from inverter 441. Additionally, AND 444 is receiving an on input via line 490 from inverter 489. Thus, AND 444 goes on which output is transmitted via line 404a to OR 494. The on output from OR 494 activates flip-flops 482, 477 and 473 as described above.

In summary, whenever AND 407 is on, very low voltage should exist at the drain of FET 418. If instead voltage exists at drain D of FET 418 then AND 411 goes on and flip-flop 482 produces an output at Q and turn off $\overline{Q}$. 1 If AND 407 is off then the voltage should exist at drain D of FET 418. If this relationship does not exist then AND 414 goes on to similarly activate flip-flop 482. An analogous situation exists for solenoid coil 438. If AND 439 is on then, low voltage should exist at drain D of FET 446. If this relationship does not exist, and 446 goes on and flip-flop 482 output Q goes on and $\overline{Q}$ goes off. If AND 439 is off then a voltage should exist at drain D of FET 446. If this relationship does not exist, the output of AND 444 goes on which causes output Q of flip-flop 482 to go on and $\overline{Q}$ to go off.

Flip-flops 473, 477, and 482, once activated by data inputs require a reset signal at terminal R via line 476 from terminal 828 to deactivate the abnormal indication status.

Solenoid Control and Monitor 400 also includes a visual indication whenever AND 407 is off to indicate visually that solenoid coil 419 is de-energized and allowing oxygen to flow continuously. This function is provided by light emitting diode 405a. Whenever the output of OR 409 is off, current supplied by voltage source $V_{DD}$ flows through line 406a, current limiting resistor 407a (1K), line 408a, diode 405a, and line 409a to the output of OR 409. Light emitting diode 405a is off whenever OR 409 receives an input via line 408 from AND 407 or when OR 409 receives an input via line 410a from terminal 820.

Figure 5:
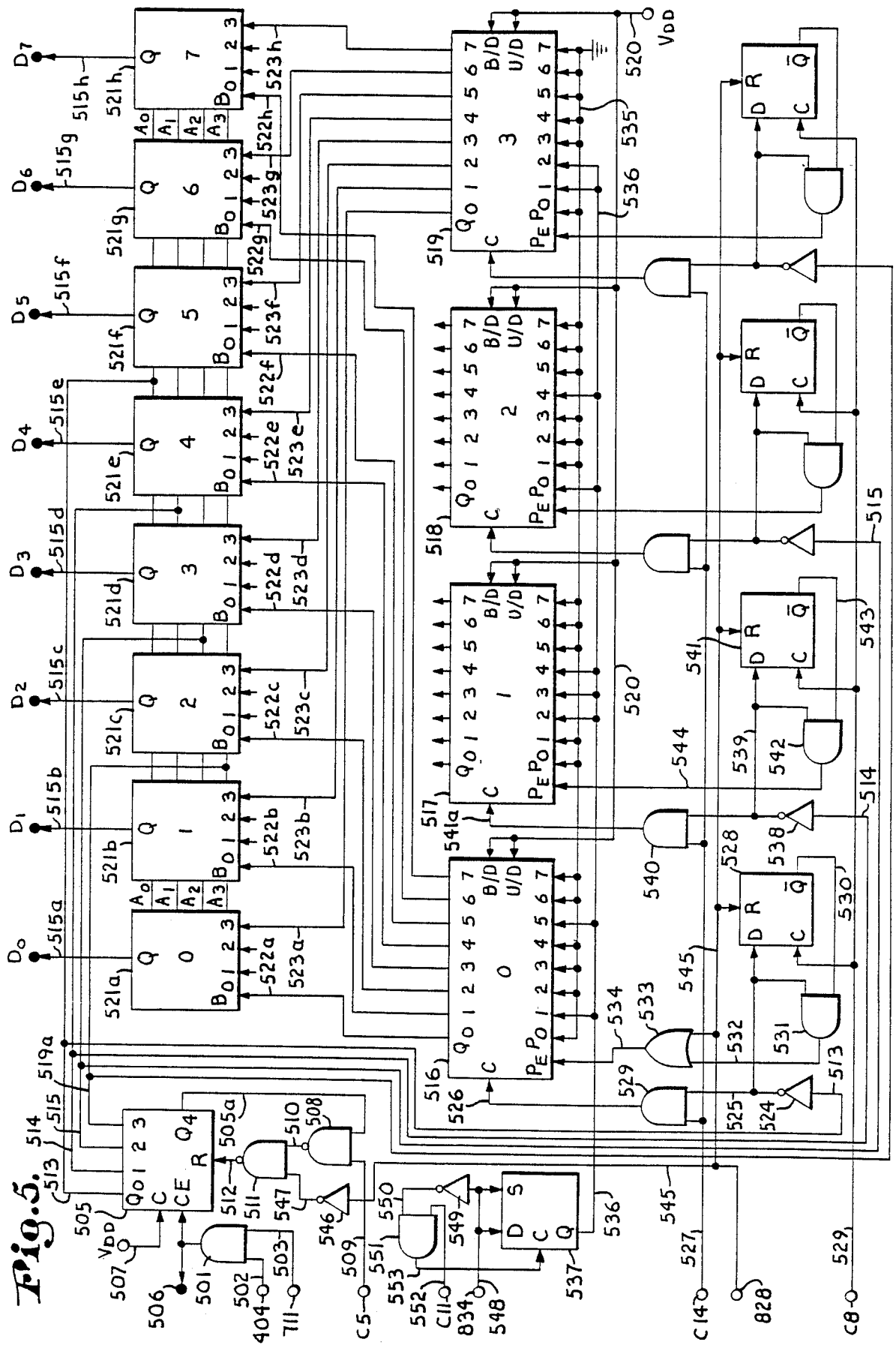
FIG. 5 is an electric schematic drawing illustrating the preferred three-breath timer circuitry forming a part of the complete controller device.

5. FIG. 5, Three-Breath Timer 500

The purpose of Three-Breath Timer module 500 is to determine and transmit count data corresponding to the total duration of the immediately preceding three breath cycles. Four eight-bit counters are used for this purpose. At the beginning of inhalation one of the counters in sequence is selected or coupled, which selection or coupling stops that counter from counting input clock pulses. The other three counters, not selected, that is, decoupled, continue to count input clock pulses. As each counter is selected or coupled in sequence, the count existing on the selected or coupled counter corresponds to the total count of the three previous breaths. Thus, by the use of four counters, one of which is transmitting data at any one time while the other three are counting clock pulses, the circuit is able to provide data corresponding to the duration of the three previous breaths. Similarly, if the data from one previous breath were desired, two counters would be required; if the data from the four previous breaths were desired, five counters would be required, and so forth. Data from the three previous breaths is used in this preferred embodiment as a matter of design choice to provide data that is very recent but also representative.

The operation of Three-Breath Timer 500 begins with reception of an on signal from terminal 404 of Solenoid Control and Monitor 400 which is transmitted to AND 501 via line 502. AND 501 receives its other input from terminal 711 via line 503. The off signal at terminal 711 indicates that blanking 700 has received a flow initiation signal. The input at terminal 404 indicates that solenoid control 400 has de-energized solenoid valve 22 to allow oxygen to flow to the patient. The output from AND 501 is transmitted via line 504 to counter selector or coupler 505 and to output terminal 506. The output from terminal 506 is delivered to the flow initiation section 302 as explained above in connection with that circuit to form the flow initiation signal into a pulse.

Counter selector 505 is a conventional eight-bit Johnson counter, here using only the first five bits. Counter selector 505 includes reset terminal R, clock enable terminal CE, clock input terminal C, and bit output terminals $Q_0$, $Q_1$, $Q_2$, $Q_3$, and $Q_4$ (output terminal for bits $Q_5$, $Q_6$, $Q_7$ are not shown because they are not used). Terminal C is clamped on continuously by voltage $V_{DD}$ via line 507. Terminal CE receives input from AND 501 via line 504.

For the sake of this illustrative example, assume that terminal $Q_3$ is on and terminals $Q_0$, $Q_1$ and $Q_4$, are off, all just before receiving an input at terminal CE. When AND 501 output goes off to terminal CE of selector 505, $Q_3$ goes off and $Q_4$ goes on. The output from $Q_4$ is transmitted via line 505a to NAND 508. NAND 508 receives its other input via line 509 from terminal C5 which is a 100 kilohertz up pulse signal. NAND 508 output then goes off at the very next input clock pulse received on line 509 after terminal $Q_4$ of selector 505 goes on. When the output from NAND 508 goes off via line 510 to NAND 511, NAND 511 then goes on via line 512 to terminal R of selector 505 to set $Q_1$ on and $Q_1$–$Q_4$ off. However, the input to terminal CE is off and the input to terminal C is on, which causes terminal $Q_0$ to go on immediately. When the reset signal was received at terminal R, $Q_4$ immediately went off to remove the reset signal thus allowing $Q_0$ to go on. At this point $Q_1$, $Q_2$, $Q_3$, and $Q_4$ are all off. Also at this point the input to AND 501 via line 503 is off because the on signal received from terminal 711 goes off when Blanking 700 receives a flow initiation signal. With AND 501 off, selector 505 is disabled, which thereby holds the output $Q_0$ on. In the next breath cycle, when another valid inhalation is sensed the inputs to AND 501 will both go off, which will advance selector 505 on output from $Q_0$ to $Q_1$ and so on with each valid inhalation.

In this way, selector 505 sequentially turns on output $Q_0$, $Q_1$, $Q_2$, and $Q_3$ and back again to $Q_0$ making a rapid transition through $Q_4$ for reset purposes only.

The output from terminal $Q_0$ of selector 505 is transmitted via line 513 to line $A_0$ which line is common to all eight data decoders 521a, 521b, 521c, 521d, 521e, 521f, 521g, and 521h. The on signal existing on line $A_0$ enables each decoder 521a–h to transmit the input signal existing on the $B_0$ of each to the Q terminal of each. Similarly, if terminal $Q_1$ of selector 505 were on instead, it is connected via line 514 to line $A_1$ and the on status of A1 would transfer the data on all the $B_1$ terminals of data selectors 521a–h to the output Q of each data decoder. Similarly, terminal $Q_2$ of counter selector 505 is connected via line 515 to line $A_2$, and terminal $Q_3$ of counter selector 505 is connected via line 516 to line $A_3$. If $Q_2$ of counter selector 505 is on, line $A_2$ is on and $B_2$ input is transferred to terminal Q output of each decoder 521a-h respectively. Similarly, if $Q_3$ of counter selector 505 is on, $A_3$ is on, and the data on terminal $B_3$ is transferred to output terminal Q of each data selector 521a-h. In this example, terminal $B_0$ of each data selector 521a-h transfers its incoming data to output terminal Q of each data sender 521a-h which is transmitted respectively via lines 515a, 515b, 515c, 515d, 515e, 515f, 515g, and 515h respectively to terminals $D_0$, $D_1$, $D_2$, $D_3$, $D_4$, $D_5$, $D_6$ and $D_7$ respectively.

Counters 516, 517, 518, and 519, are each composed of two conventional four-bit up counters conventionally connected to form an eight-bit counter. Each eight-bit counter 516-519 includes output terminals $Q_0$ (least significant bit), $Q_1$, $Q_2$, $Q_3$, $Q_4$, $Q_5$, $Q_6$, and $Q_7$ (most significant bit). Each counter also includes preset input terminals for each bit, $P_0$ (least significant bit), $P_1$, $P_2$, $P_3$, $P_4$, $P_5$, $P_6$, and $P_7$ (most significant bit). Additionally each counter includes clock input terminal C, binary decimal selector terminal B/D, count up-down selector terminal U/D, and preset enable terminal $P_E$. Terminals B/D and U/D on each counter are clamped high via line 520 from voltage source $V_{DD}$ to select a binary up count.

Each bit output terminal $Q_{0-7}$ from each counter 516-519 is connected individually to the appropriate input of each decoder 521a-h. That is, the eight outputs from counter 516 are connected respectively to the $B_0$ input terminal of each decoder 521a-h. Specifically regarding counter 516, $Q_0$ is connected to $B_0$ of decoder 521a by line 522a; $Q_1$ is connected to $B_0$ of decoder 522b by line 522b; $Q_2$ is connected to terminal $B_0$ of decoder 521c via line 522c; $Q_3$ is connected to terminal $B_0$ of decoder 521d via line 522d; $Q_4$ is connected to terminal $B_0$ of decoder 521e via line 522e; $Q_5$ is connected to terminal $B_0$ of decoder 521f via line 522f; $Q_6$ is connected to terminal $B_0$ of decoder 521g via line 522g, $Q_7$ is connected to terminal $B_0$ of decoder 521h via line 522h. Similarly, the outputs of $Q_{0-7}$ of counter 517 are connected to the $B_1$ terminals of decoders 521a-h respectively and the outputs $Q_{O-7}$ of counter 518 are connected to the $B_2$ terminals of decoders 521a-h respectively. The output connections between counters 517 and 518 and decoders 521a-h are not shown in FIG. 5 because the multitude of connecting lines would make the drawing difficult to read. In order to further illustrate, the connections between counter 519 and the $B_3$ terminal of decoders 521a-h respectively are shown via lines 523a, b, d, c, e, f, g, h, respectively.

The output $Q_0$ of counter ,selector 505 is transmitted via line 513 to line $A_0$ of decoders 521a-h as discussed above and also to inverter 524 whose output immediately goes off at line 525 when $Q_0$ goes on. When inverter 524 goes off, and 525 output goes off via line 526 to terminal C of counter 516. When AND 529 goes off, the 4.16 hertz up pulses received via line 527 from terminal C14 can no longer clock through AND 525 and the up count on counter 516 stops. Because the output via line 513 to line $A_0$ of decoders 521a-h is on, the output from counter 516 transmits on through terminal $B_0$ of each decoder to the output Q of each decoder to data output terminals $D_O-D_7$. Thus, when the up count on counter 516 was stopped, the accumulated count data transmitted through to terminals $D_{0-7}$. This up count represents the accumulated count of the three previous breath cycles. It will be appreciated that this accumulated count inherently represents a measured breath rate.

When inverter 524 went off, this output was transmitted via line 525 to flip-flop 528. Flip-flop 528 is a conventional D type with reset and includes data input terminal D, reset terminal R, clock input terminal C, and output terminal $\overline{Q}$. (Output terminal Q is not shown because it is not used.) Terminal C receives a one kilohertz downpulse signal via line 529 from terminal C8. When inverter 524 output went off, the input data received at terminal D of flip-flop 528 also went off and upon the rising edge of the very next clock input at terminal C, Q went on via line 530 to AND 531. AND 531 receives its other input from inverter 524 via line 525. When counter selector 505 advances on the next breath cycle from $Q_0$ to $Q_1$, the input to inverter 524 will go off and its output will go on to AND 531. Because the other input via line 529 is already on, AND 531 output goes on via line 532 to OR 533 which goes on via line 534 to terminal $P_E$ of counter 516. With an on input at terminal $P_E$, counter 516 25 is enabled to load the preset values existing at $P_{0-7}$. Terminals $P_{0'\ 2'\ 3'\ 4'\ 6'}$ and $7'$ are clamped to ground 6 via line 535. Terminals $P_1$ and $P_5$ are connected via line 536 to the output Q terminal of flip-flop 537. At this point in the sequence the output from flip-flop 537 is off and so all of the values at preset terminals $P_{O-7}$ are off and when counter 516 receives the preset enable signal at $P_E$, it loads all of these zero values into bits $Q_{0-7}$. In this way, counter 516 is reset to zero for all output bits when counter selector 505 advances from $Q_0$ to $Q_1$. At the same time, when inverter 524 goes on, AND 525 will be enabled to begin transmitting clock pulses to terminal C of counter 516. Thus, when counter 516 is de-selected or decoupled by counter selector 505 by virtue of terminal $Q_0$ of selector 505 going off, inverter 524 goes on which causes flip-flop 528 to set all counter values to zero, which allows counter 516 to again receive clock pulses at terminal C.

The operation of counter 517 is very similar to that of counter 516. When $Q_1$ of selector 505 goes on, this output is transmitted via line 514 to inverter 538 whose output goes off via line 539 to AND 540. When inverter 538 goes off, AND 540 output goes off via line 541 to terminal C of counter 517. When the output of inverter 538 went off the input to terminal D of flip-flop 541 went off also. Flip-flop 541 is identical to flip-flop 528. Additionally, AND 542 was disabled via line 539 when inverter 538 went off. When counter selector advances from $Q_1$ to $Q_2$ and inverter 538 thus goes back on, AND 542 is enabled via line 539 and line 543 from the $\overline{Q}$ output of flip-flop 541. The on output from AND 542 is transmitted via line 544 to terminal $P_E$ of counter 517 which loads zeroes into all eight bits of counter 517 thus resetting the counter. Additionally, with inverter 538 output on, AND 540 is enabled to transmit clock signals via line 541 to terminal C of counter 517. The construction and operation of counters 518 and 519 are identical to those described for counter 517.

The reset and preset enable function of counter 516 differs from that of 517-519 only in the addition of OR 533 with counter 516. This is provided to enable a master reset signal to be received by OR 533 from terminal 828 via line 545. Line 545 also connects to the input of inverter 546 whose output is connected via line 547 to NAND 511.

The preset function of counters 516-519 is used to preload values into counters 516-519 whenever flip-flop 537 output is on. This occurs only when terminal 834 is on during conditions to be described below in the description of Reset and Power Monitor 800 (e.g. solenoid failure, power up). Flip-flop 537 is a conventional "D" type flip-flop with set function and includes data input terminal D, set input terminal S, clock input terminal C, and output terminal Q, which output is transmitted via line 536 to various preset terminals (P$_{0-7}$) of counters 516–519. An on signal at terminal 834 is transmitted via line 548 to terminals D and S of flip-flop 537 and to inverter 549. The on input to inverter 549 causes its output to go off via line 550 to AND 551. AND 551 then transmits 100 hertz up pulses received via line. 552 from terminal C11. These clock output pulses from AND 551 are transmitted via line 553 to terminal C of flip-flop 537. The provision of the clock signals to AND 551 provides a slight time delay before terminal Q of flip-flop 537 goes on.

With line 536 being on, each counter 516–519 is able to load predetermined counts. counter 516 is wired for a preloaded count of decimal 34 by applying the on signal to bits P$_1$ and P$_5$. Counter 517 is loaded with a count of decimal 28 by providing the on signal to bits P$_2$, P$_3$, and P$_4$. Counter 518 is preloaded with decimal 17 by connecting terminals P$_0$ and P$_4$ Counter 519 is preloaded with decimal value 6 by connecting terminals P$_1$ and P$_2$. The balance of the preset terminals are clamped low, i.e. zero, by line 535 to ground 6. It is necessary to preload count data into counters 516–519 whenever a three breath history does not exist for the counters. For example, when the unit is first turned on.

Figure 6:
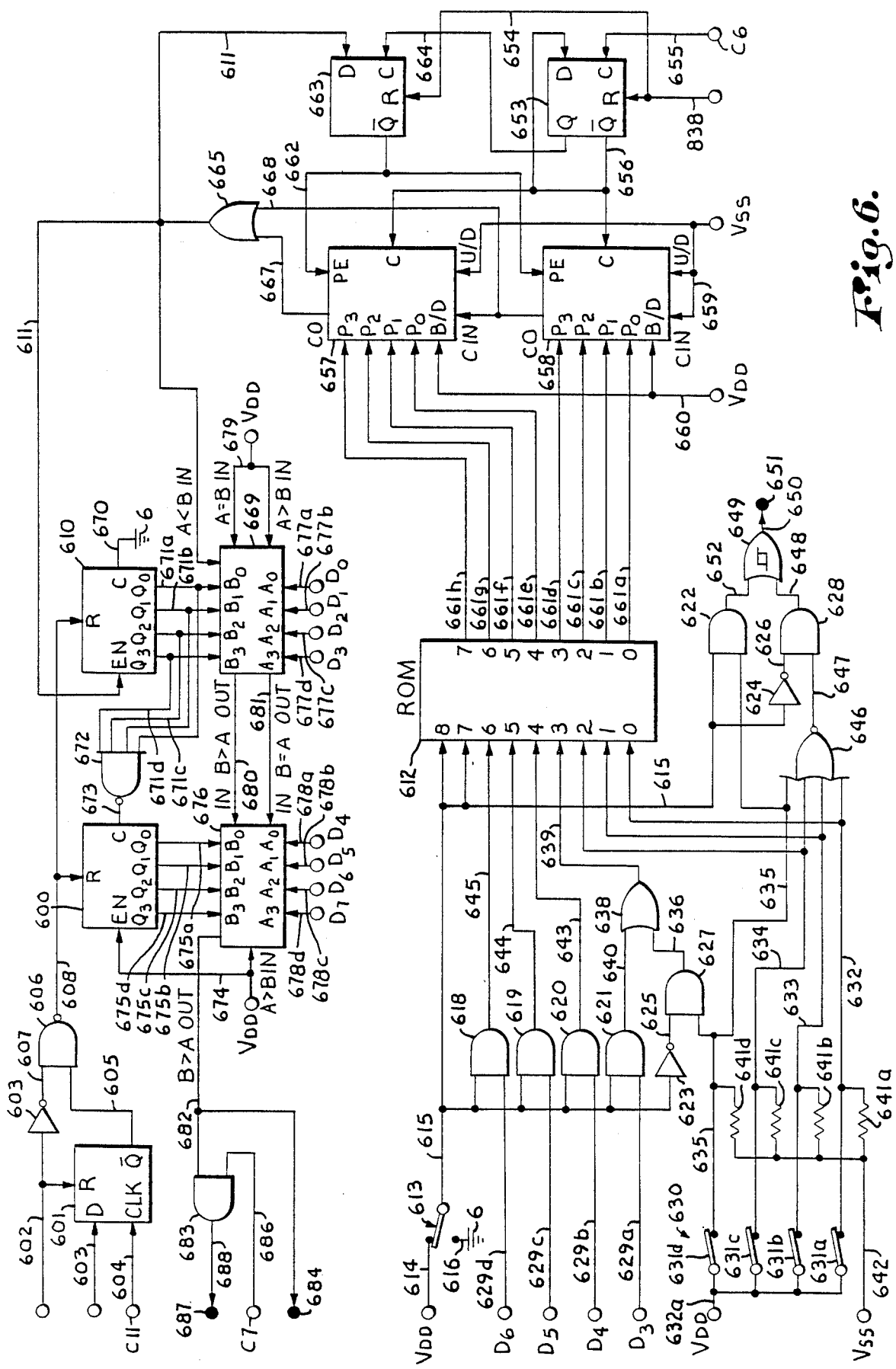
FIG. 6 is an electrical schematic drawing showing the preferred flow pulse circuitry making up a part of the complete controller device.

6. FIG. 6, Flow Pulse Circuit 600

Flow Pulse Circuit module 600 determines the time duration of the oxygen pulse supplied to the patient. The circuit does this by selecting a value in a read-only memory which value is selected based on the pulse count data received from Three Breath Timer module 500 and based on binary encoded decimal information received from the prescription flow dial mechanically attached to solenoid valve 20. The values stored in the read-only memory are determined so that the patient receives the substantially physiologically equivalent oxygen from the pulse as the patient would receive from continuous oxygen flow. That is to say, the preferred values in memory are based on an assumed I/E ratio of 1 to 1.5 as discussed above in connection with graph 1305, to provide a constant "minute volume" of oxygen; this is a conservative ratio assuring adequate oxygen to the patient under normal conditions. Other ratios are of course possible (and easily substitutable into memory), as is the expedient of continuously measuring the I/E ratio.

The operation of Flow Pulse Circuit 600 begins with conventional "D" type flip-flop with reset 601 which includes data input terminal D, clock input terminal C, reset terminal R, and output terminal $\overline{Q}$ (terminal Q is not shown because it is not used). Terminal R can receive a reset input from terminal 834 via line 602 which line is also connected to inverter 603. Terminal D receives an input from terminal 404 which is an output from solenoid control and monitor 400 via line 603. Terminal C receives 100 hertz up pulse clock signals from terminal C11 via line 604. Terminal $\overline{Q}$ transmits its output via line 605 to NAND 606 which receives its other input via line 607 from inverter 603. Terminal 834 is normally off unless a reset condition exists (e.g. solenoid failure, power up).

In normal operation before the patient has inhaled, terminal 404 is on and as a result terminal $\overline{Q}$ of flip-flop, 601 is off, which disables NAND 606 whose output is thus on via line 608 to hold counters 609 and 610 in a reset condition.

When the patient inhales, Solenoid Control and Monitor 400 receives a flow initiation pulse which causes terminal 404 to go off When this occurs, the very next clock input pulse at terminal C of flip-flop 601 causes Q to go on. This delay of one clock pulse between the time terminal 404 goes off and $\overline{Q}$ goes on gives Three Breath Timer 500 the amount of time necessary to select the next counter. With terminal $\overline{Q}$ of flip-flop 601 on via line 605 to NAND 606, the output from NAND 606 goes off; inverter 603 is on to satisfy the other input to NAND 606 because no reset signal is being received at terminal 834. When the output of NAND 606 goes off, up counters 609 and 610 are no longer in reset condition and are able to begin counting pulses received to up counter 610 via line 611. At this point Flow Pulse Circuit 600 begins timing the duration of the oxygen flow pulse.

The timing function of flow pulse circuit 600 centers about read-only-memory [ROM] 612. ROM 612 is a conventional read-only-memory structure having 512 locations of eight bits each. Nine address inputs are provided and the output is provided as eight bits of data. In the drawing, the address inputs are represented on the leftmost side of ROM 612 at terminals 0, 1, 2, 3, 4, 5, 6, 7, and 8. In the drawing, the output terminals are on the rightmost side of ROM 612 and labeled 0, 1, 2, 3, 4, 5, 6, and 7 ranging from the least significant bit to the most significant bit respectively. The memory of ROM 612 is mapped into a plurality of sections only two of which are used for the hospital and home embodiments respectively. Memory locations 0 through 9 are used for the hospital mode and 10 through 99 for the home unit application.

Switch 613 is connected to voltage source V$_{DD}$ (+5 V.D.C.) via line 614 which is the position (as shown) for home unit application and switch 613 is clamped to ground 6 via line 616 for the hospital unit. In the home unit application, switch 613 is positioned as shown to supply a continuous on voltage via line 615, address inputs 7 and 8 are on, AND gates 618, 619, 620, 621, and 622 are enabled, and the outputs of inverters 623 and 624 are off via lines 625 and 626 respectively to disable AND gates 627 and 628.

In the hospital mode with switch 613 selected to ground, AND gates 618–621 are disabled which prevents any input to the memory of ROM 612 from terminals D3, D4, D5, and D6 via lines 629a, 629b, 629c, 629d respectively. The data input from terminals D3–D6 are not needed in the hospital unit application because the oxygen pulse wave form is a regular square wave pulse (See FIG. 13, graph 1305) and as such, is more predictable in its physiological effect on the patient's partial pressure of arterial oxygen. Thus, not as many empirically derived values need be stored in ROM 612 and for this reason the address input in the hospital unit comes only from the flow selector dial which provides the binary encoded decimal output [BCD] 630. With switch 613 thus selected to the hospital unit, address inputs at terminals 4–8 are always off and inputs at terminals 0–3 of the address input are needed.

BCD 630, to address the hospital memory section, basically comprises four switches 631a, 631b, 631c, and 631d which range from the least significant bit to the most significant bit respectively. One side of each switch 631a–d is connected via line 632 to voltage source $V_{DD}$. The other side of switches 631a–c are connected via lines 632, 633, and 634 to address terminals 0, 1, and 2 respectively. The output from switch, 631d is transmitted via line 635 to AND 627 whose output is transmitted via line 636, OR 638, and line 639 to terminal 3.

The four switches can convey a total count of decimal 15 when all switches are closed as shown. However, in the home unit the maximum allowable prescription flow rate is seven liters per minute, when switch 613 is selected to the home unit, the input to inverter 623 is on and its off output disables AND 627 thus preventing any data flow to the address from switch 631d which in turn represents the most significant bit which represents a count of decimal 8 when switch 631d is closed. Thus, in the home mode address, terminal 3 receives input terminal $D_3$ via line AND 621, 621a via line 640, OR 638, and line 639.

In the hospital mode however, a continuous flow rate greater than seven is selectable and the bit data from all four switches is needed. In this mode AND 627 is enabled because inverter 623 is on and AND 627 thereby transmits a bit count from switch 631d.

The outputs from switches 631a–d at lines 632–635 are tied to $V_{SS}$ (which is D.C. ground) through resistors 641a, 641b, 641c, and 641d respectively via line 642. This is necessary because of the nature of the CMOS (complimentary metal oxide semiconductor) devices used in this circuit in order to prevent line voltage from drifting when any of switches 631a–d open.

In the home embodiment, a more complicated oxygen flow pulse shape is encountered because of the pneumatic structure of the device (see FIG. 13 graph 1305). Because of this fact, a greater number of values are needed to be stored in the memory of ROM 612 and address data is needed at address terminal 3–8 in addition to that provided by BCD 630 at address terminal 0–2. In the home mode as described above, address terminals 7 and 8 are on, AND gates 618–621 are enabled and the output of inverter 623 is off to thereby disable AND 627 to prevent address data from BCD switch 631d. With AND gates 618–621 enabled ROM 612 can received address data at terminals 3–6 from input data terminals D3, D4, D5, D6, which represent count data from Three Breath Circuit 500. The data input from D3–D6 only is used because the additional resolution that would be provided by the use of data from terminals D0, D1, D7 is not needed for the purposes of the ROM 612 address.

As described above, input data from terminal D3 is transmitted to address terminal 3. Address data from terminal D4 is received at address terminal 4 via line 629b, AND 620, and line 643. Address data from terminal D5 is received at address terminals 5 via line 629c, AND 619, and line 644. Input data from terminal D6 is transmitted to address terminal 6 via line 629d, AND 618, and line 645.

The data from BCD 630 is also transmitted to NOR 646 via lines 632–635. If the continuous flow dial is selected to zero liters per minute all four inputs to NOR 646 are off and NOR 646 goes on via line 647 to AND 628. If the hospital mode is selected at switch 613, the in put to inverter 624 is off whose output is on to AND 628. With both inputs on, AND 628 output goes on via line 648 to Schmitt-trigger OR 649 whose on output is transmitted via line 650 to output terminal 651 which, through circuitry described in more detail below, resets the system to provide continuous oxygen flow. That is, in the hospital mode, if a continuous flow of zero is selected the entire system is disabled from supplying oxygen pulses.

In the home mode, the same continuous flow rate selector dial is provided but with an additional mechanical stop which inhibits a continuous flow rate selection greater than seven. However, if the dial would be mechanically forced beyond the seven liter per minute position, line 635 would be on to AND 622. The other input to AND 622 is also on and the output of AND goes on via line 652, OR 649, line 650, to terminal 651. Thus a forced selection above seven liters per minute on the home embodiment indicates a malfunction which resets the system and puts it into a continuous oxygen flow mode.

The next part of flow pulse circuit 600 takes an incoming clock pulse and scales the frequency to an output determined by the data of ROM 612.

Conventional "D" flip-flop with reset 653 includes input data terminal D, clock terminal C, reset terminal R, and output terminals Q and $\overline{Q}$. Terminal R can receive a reset signal from terminal 838 via line 654 which is off unless a reset condition or flow initiation pulse exists. Terminal C receives a ten kilohertz downpulse clock signal from terminal C6 via line 655. Terminal D receives input from terminal $\overline{Q}$ via line 656. With this arrangement flip-flop 653 scales the incoming ten kilohertz downpulse signal to a five kilohertz square wave signal with a 50% duty cycle at terminal Q. This occurs because an input of one-on terminal D causes $\overline{Q}$ to go off at the very next incoming clock pulse which changes the input to terminal D to 0 which causes $\overline{Q}$ to then go on at the very next incoming clock pulse. In this way the outputs of both $\overline{Q}$ and Q are five kilohertz signals.

The five kilohertz output from terminal $\overline{Q}$ of flip-flop 653 is also transmitted via line 656 to the clock input terminals of conventional four-bit downcounters 657 and 658. Counters 657 and 658 are identical four-bit downcounters connected to one another to effectively form an eight-bit downcounter. Each counter 657 and 658 includes input data preset terminals $P_0$, $P_1$, $P_2$, and $P_3$. Additionally, each counter includes carry in terminal CI, carry out terminal C0, binary decimal selector terminal B/D, and up or downcount selector terminal U/D. Both U/D terminals are clamped low to terminal $V_{SS}$ via line 659 so that each downcounts. The B/D terminal of each counter is clamped high to $V_{DD}$ via line 660 to select the binary count mode. Additionally, terminal CI of counter 658 is clamped low via line 659 to voltage terminal $V_{SS}$ Counter 658 receives input data at terminals $P_{0-3}$ via lines 661a, 661b, 661c, 661d respectively from ROM 612 output terminals 0–3 respectively. Counter 657 receives input data at terminals P0–3 via lines 661e, 661f, 661g, 661h respectively from ROM 612 output terminals 4–7 respectively. Counter 657 and 658 each receive inputs at terminals $P_E$ via line 662 from flip-flop 663.

Flip-flop 663 is identical to flip-flop 653 except that terminal Q is not shown because it is not used.

A flow initiation pulse sets terminal 838 on momentarily which is transmitted to terminal R of both flip-flops 653 and 663 via line 654 which initially sets the $\overline{Q}$ output of both flip-flops 653 and 663 on. When the reset pulse is removed, and $\overline{Q}$ of flip-flop 663 goes on, counters 657 and 658 are enabled via line 662 to load data from ROM 612. As soon as data is loaded, each CO terminal of counters 657 and 658 go on via lines 667 and 668 respectively to OR 665. OR 665 output is on until all of the bits of counters 657 and 658 are off. The on output of OR 665 is transmitted via line 611 to terminal D of flip-flop 663. Upon the next clock pulse input at terminal C via line 664, $\overline{Q}$ goes off which disables counters 657 and 658 from loading data from ROM 612. At this point counters 657 and 658 can begin downcounting with each input pulse received at their respective C terminals via line 656.

When the count on both counters 657 and 658 reaches zero, both outputs at CO via lines 667 and 668 go off and OR 665 goes off. When OR 665 output goes off, flip-flop 663 terminal $\overline{Q}$ output goes on at the next incoming clock pulse at terminal C. When terminal $\overline{Q}$ goes on, counters 657 and 658 are again-enabled to load data from ROM 612. As soon as the data is loaded OR 665 goes on again, $\overline{Q}$ of flip-flop 663 goes off which removes the enabling input to both counters 657 and 658, and each counter again begins its countdown. The net effect of the repeated data loading and countdown of counters 657 and 658 is an output from OR 665 which is a downpulse of frequency equal to five kilohertz divided by the sum of the ROM data number plus one. Thus the incoming ten kilohertz input clock signal is scaled according to the selected ROM data which was selected by the address provided by BCD 630 and data from three breath timer 500 (when the home use is selected).

The last portion of Flow Pulse Circuit 600 uses the downpulse output of OR 665 as the frequency with which to count the data provided by three breath time 500.

The output of OR 665 is transmitted via line 611 to upcounter 610 and comparator logic circuit 669. Upcounter 610 is a conventional four-bit counter with reset and includes reset terminal R, clock terminal C, enable terminal EN, and output bit terminals $Q_0$ (least significant bit), $Q_1$, $Q_2$, and $Q_3$ Terminal C is clamped to ground 6 via line 670. When the reset signal from NAND 606 is removed from terminal R of upcounter 610, counter 610 begins counting the rising edge of the incoming down-pulses from OR 665. The outputs from terminals $Q_{0-3}$ are transmitted via lines 671a, 671b, 671c, and 671d respectively to NAND 672. When all outputs $Q_{0-3}$ of counter 610 are on, NAND 672 output goes off via line 673 to upcounter 609.

Upcounter 609 is identical to counter 610 but with terminal EN clamped high via line 674 to $V_{DD}$ and terminal C connected via line 673 to the output of NAND 672. This arrangement combines upcounters 609 and 610 into a functional eight-bit counter with counter 609 receiving the overflow count from upcounter 610. That is, when NAND 672 goes off which occurs when a full count exists on counter 610, the very next input pulse to counter 610 causes all of its bits to go off, which causes NAND 672 to go on which provides one count of input to counter 609. In this way counter 609 receives one bit of input each time counter 610 overflows. The reset signal to terminal R of counter 609 was removed via line 608 at the same time it was removed from counter 610. The output from counter 609 at terminals $Q_0$ (least significant bit), $Q_1$, $Q_2$, and $Q_3$ (most significant bit) is transmitted via lines 675a, 675b, 675c, and 675d respectively to comparator logic circuit 676.

Circuits 669 and 676 are conventional count comparator logic circuits. Each circuit 669 and 676 includes input terminals $B_0$, $B_1$, $B_2$, and $B_3$ and input terminals $A_0$, $A_1$, $A_2$, and $A_3$ Circuit 669 receives input data at terminals $B_{0-3}$ from upcounter 610 via lines 671a-d respectively. Logic circuit 669 receives input data from terminals $D_0$, $D_1$, $D_2$, and $D_3$ of three breath timer 500 via lines 677a, 677b, 677c, and 677d respectively to terminals $A_{0-3}$ respectively. Similarly logic circuit 676 receives inputs at terminals $B_{0-3}$ from upcounter 609 via lines 675a-d respectively. Additionally, logic circuit 676 receives input at terminals $A_{0-3}$ from terminals $D_4$, $D_5$, $D_6$, and $D_7$ of three breath timer 500 via lines 678a, 678b, 678c, and 678d respectively.

In logic circuit 669, the terminals A=B IN and A>B IN are clamped high via line 669 to $V_{DD}$. The B>A OUT terminal of logic circuit 669 is connected via line 680 to the B>IN terminal of logic circuit 676. The B=A OUT terminal of logic circuit 669 is coupled via line 681 to the B=A IN terminal of logic circuit 676 the A>B IN terminal of circuit 676 is clamped high via line 674 to $V_{DD}$.

When the functional eight-bit count represented on the outputs of upcounters 609, 610 exceeds the count delivered by three breath timer terminals $D_0$-$D_7$ to logic circuits 676 and 669, then B>A OUT of logic circuit 676 goes on which output is transmitted via line 682 to AND 683, and output terminals 684 and 685. AND 683 receives its other input as a ten kilohertz up pulse from terminal C7 via line 686. On the very next clock pulse received by AND 683 after line 682 goes on, AND 683 goes on to terminal 687 via line 688.

The output from terminal 684 goes to Flow Initiation and Rezeroing 300 to start the conversion process of successive approximation register 364. The output at terminal 687 goes to Solenoid Control and Monitor 400 to reset flip-flop 402.

7. FIG. 7, Blanking 700

When Flow Pulse Circuit 600 times out the duration of the oxygen pulse and flow initiation and rezeroing 300 completes the conversion on successive approximation register 364, solenoid valve 22 is energized to end the oxygen flow to the patient. However, the oxygen pulse ends while the patient is still inhaling and as a result inhalation sensor 100 begins indicating that patient inhalation is occurring. The main purpose of Blanking module 700 is to prevent inhalation sensor 100 from triggering another oxygen pulse during the same period of inhalation. Blanking 700 accomplishes this by preventing Three Breath Timer 500 from being triggered by AND 501.

Blanking 700 receives the output from Flow Initiation and Rezeroing 300 indicating that a valid inhalation has occurred at terminal 347 which on signal is transmitted via line 701 to flip-flop 702 and inverter 703. When inverter 703 receives this on signal its output goes off via line 704 to AND 705. AND 705 then goes off via line 706 to OR 707. The other input to OR 707 is from terminal 834 via line 708 which is normally off unless a reset condition exists. When the output of AND 705 goes off the output from OR 707 goes off via line 709 to remove the reset input to flip-flop 702.

Flip-flop 702 is a conventional "S" flip-flop with set and reset and includes input set terminal S, reset terminal R, and output terminal $\overline{Q}$ (output terminal Q is not shown because it is not used).

With the reset signal at terminal R removed and an on signal received at terminals S, $\overline{Q}$ of flip-flop 702 goes off which is transmitted via line 710 to terminal 711 and flip-flop 712. The off output at terminal 711 prevents AND gate 501 (FIG. 5) from going on at least as long as the output from flip-flop 702 is off.

Flip-flop 712 is a conventional "D" type flip-flop with a set function and includes data input terminal D, clock input terminal C, set input terminal S, and output terminal Q. Flip-flop 712 can receive a set signal from terminal 834 via line 708 at terminal S which input is normally off. Flip-flop 712 also receives a one kilohertz downpulse clock signal from terminal C8 via line 713. Upon reception of the very next clock pulse at terminal C, the off signal at terminal D (from $\overline{Q}$ of flip-flop 702) clocks through and turns off terminal Q of flip-flop 712.

When terminal Q of flip-flop 712a goes off via line 714, downcounters 714 and 715 begin downcounting against the count received from Three Breath Timer 500. The clock pulse delay of flip-flop 712 in turning off terminal Q output gives Three Breath Timer 500 time to advance to the next counter and allows downcounters 714 and 715 time to load in the data from the new counter selected by Three Breath 500, all this occurring before the output from terminal Q goes off.

Counters 714 and 715 are conventional four-bit counters connected to function as an eight-bit counter. Each counter 714 and 715 includes binary decimal selector terminal B/D, clock input terminal C, carry in terminal CI, up/down count selector terminal U/D, preset enable terminal $P_E$, carry out terminal CO, and data input terminals $P_0$ (least significant bit), $P_1$, $P_2$, and $P_3$. Each B/D terminal is clamped high to voltage source $V_{DD}$ via line 716 to thereby select the binary count mode. Each U/D terminal is clamped to ground 6 via lines 717 and 718 respectively to select the downcount mode. Additionally, each counter 714, 715 receives twenty hertz up pulse clock signals from terminal C13 via line 719. Terminals $P_{0-3}$ of counter 715 receive input data from terminals D0, D1, D2, and D3 from Three Breath Timer 500 via lines 719, 720, 721, and 722 respectively. Terminals $P_{0-3}$ of counter 714 receive input data from terminals D4, D5, D6, D7 of Three Breath Timer 500 via lines 723, 724, 725, and 726 respectively. Terminal CI of counter 715 is clamped to ground 6 via line 718.

When counter 715 completes the downcount of the data loaded at terminals $P_{0-3}$, terminal CO, which is on whenever any bit is on, goes off which output is transmitted via line 727 to NOR 728 and CI of counter 714. When the input to counter 714 at CI goes off, counter 714 then begins downcounting the data loaded at terminals $P_{0-3}$. When the downcount is complete and all bits are off, terminal CO goes off via line 729 to NOR 728. With both inputs off, the output from NOR 728 goes on via line 730 to AND 705. The other input to AND 705 is on because the input to inverter 703 was on only during the short duration flow initiation pulse received at terminal 347. The output from AND 705 thus goes on through OR 707 to terminal R of flip-flop 702 which resets flip-flop 702 so that terminal $\overline{Q}$ goes on. When terminal $\overline{Q}$ goes on, AND 501 of Three Breath Timer 500 is enabled for another cycle. The on output at terminal Q of 702 is input to terminal D of flip-flip 712 and after one clock pulse terminal Q of flip-flop 712 goes on to the $P_E$ terminals of counters 714 and 715 which enables counters 714 and 715 to reload data existing on terminals $D_{0-7}$ and both counters 714 and 715 are thus ready for the next cycle as are flip-flops 702 and 712.

Counters 714 and 715 downcount the data received from Three Breath Timer 500 at a faster rate (20 HZ) than which that count data was generated (4.16 HZ). That is, the data is counted down at the rate of 20 hertz but was generated at the rate of 4.16 hertz. However, the count data generated by Three Breath Timer 500 covered three breath cycles where the countdown of blanking 700 takes less than one cycle. Thus, the countdown of blanking 700 is scaled to extend the blanking time into the exhale portion of the same breath cycle in which the blanking time started (see FIG. 13).

8. FIG. 8, Reset and Power Monitor 800

The purpose of Reset and Power Monitor module 800 is to reset the memory elements of the various circuits such as flip-flop counters and registers, to initialize the system, and various components reset if an abnormality occurs.

The power monitor portion of Reset and Power Monitor 800 monitors the 12 V.D.C. power supply for any dip in voltage. That is, this portion activates if the 12 volt power supply drops below approximately 10.7 volts. Power supply voltage at 12 V.D.C. is supplied through a voltage divider to a conventional differential operational amplifier 801 including a positive input terminal, a negative input terminal and an output. Operating voltage for amplifier 801 is supplied from $V_{EE}$ (+8 V.D.C.) via line 802 and is referenced to ground 6 via line 803. Nominal 12 volt D.C. power is supplied via line 804, resistor 805 (290K), and line 806 to the positive input terminal of amplifier 801. The balance of the 12 V.D.C. voltage divider network is formed by line 806 to resistor 807 (100K) the other side of which is connected to ground 6 by line 803. The input to negative input terminal of amplifier 801 comes from line 808 which is part of voltage divider network starting with terminal $V_{DD}$ (+5 V.D.C.), line 809, resistor 810 (100K), line 808, resistor 811 (100K), and line 803 to ground 6.

When the voltage supplied to the positive input terminal of amplifier 801 is greater than that supplied to the negative input terminal, the output of amplifier 801 is on. If the 12 V.D.C. supply voltage drops, the voltage supplied by $V_{DD}$ should still remain steady because this voltage at +5 V.D.C. is less than the supply voltage of 12 V.D.C. When the supply voltage drops to approximately 10.0 volts, the voltage at the negative input terminal of amplifier 801 is greater than the voltage at the positive input terminal and amplifier 801 output goes of via line 812 to resistor 815 (4.02K), and then via line 816 to inverter 817 and capacitor 818. Resistor 815 properly biases the output of amplifier 810 for digital operation. The other side of capacitor 818 is connected to ground 6 via line 803.

In normal operation, amplifier 801 output is on with the result that the output of inverter 817 is off. If the 12 V.D.C. power supply voltage drops, amplifier 801 goes off and the output from inverter 817 goes on.

Capacitor 818 is used at power up to delay the on input to inverter 817 to allow the system to reset to initial values. When amplifier 801 initially goes on, current flow into capacitor 818 delays the rise of the input voltage to inverter 817 and provides about a one second delay.

The output from inverter 817 is transmitted via line 819 to terminal 820 which connects with Failure Indicator 900 explained in more detail below, and with OR 821. OR 821 receives its other input from terminal 651 via line 822. An on input at terminal 651 indicates that the selector dial for solenoid valve 20 is set at a flow rate of zero for the hospital unit which is indicated on BCD 630 (or a flow setting over seven for the home unit) as explained in connection with Flow Pulse Circuit 600.

The output from OR 921 is transmitted via line 823 to terminal 825 which initiates a conversion cycle for successive approximation register 364 and to Schmitt-trigger OR gate 826. OR 826 receives its other input via line. 827 to terminal 222 which is on in the event of an abnormality in oscillator 201.

The output from OR 826 is transmitted via line 827 to terminal 828, and OR gates 829 and 830. The output from terminal 828 is conveyed to the various individual circuits as described in connection with each circuit and functions as a master reset to put virtually all of the memory elements in an initial status.

OR 829 also receives inputs from terminal 484b via line 831 which is on in the event of a solenoid coil abnormality as detected by Solenoid Control and Monitor 400, and terminal 1127 via line 832 which is on in the event Seek/ Deliver 1100 is activated which is explained in more detail below. The output from OR 829 is conveyed via line 833 to terminal 834 and OR 835.

OR 835 receives its other input from flow initiation 302, terminal 347 via line 836 which comes on when a valid inhalation is detected. The output from OR 835 is transmitted via line 837 to terminal 838. The second input to OR 830 is also from terminal 346 of flow initiation 302 which is on when a valid inhalation is detected.

9. FIG. 9, Failure Indicator 900

The purpose of failure indicator 900 is to provide a visual signal in the event of a system failure or reset. NOR gate 901 receives inputs from terminal 376 of rezero 301 via line 902 which is on in the event an overrange exists on successive approximation register 364; from terminal 828 of Reset and Power monitor 800 which is on in the event of clock failure, zero oxygen flow selection, power failure or briefly on power up; from terminal 1161 of Seek/Deliver 1100 via line 904 which is on whenever Seek/Deliver 1100 is activated; and from terminal 484c of Solenoid Control and Monitor 400 which is on whenever a solenoid abnormality is detected. If any of the inputs to NOR 901 are on, NOR 901 output is off via line 906 to OR 907.

The other input to OR 907 is from terminal 820 of Reset and Power Monitor 800 via line 908 which is on in the event of low power supply voltage or briefly on power up. If both inputs to OR 907 are off which occurs in the event of any of the abnormalities described above, then the off output from OR 907 allows light emitting diode 909 to go on. The cathode of diode 909 is connected to the output of OR 907 via line 910. Power is supplied to diode 909 from voltage source $V_{DD}$ via line 911, resistor 912 (1K), and line 913 connected to the anode of diode 909.

10. FIG. 10, Audible Alarm 1000

Conventional audible alarm 1001 is activated by an output from OR 1002 via line 1003. OR 1002 is on if any of its four inputs are on which indicates an abnormal condition. OR 1002 receives input from terminal 376 of rezeroing 301 via line 1004 which indicates an overrange condition on successive approximation register 364. The second input to OR 1002 is from terminal 484d of Solenoid Control and Monitor 400 via line 1005 which indicates an abnormal solenoid control condition The third input to OR 1002 is from terminal 828 of Reset and Power Monitor 800 via line 1006 which indicates clock failure, zero oxygen flow selection, low voltage power supply, and briefly on power up. The fourth input to OR 1002 is from flip-flop 1007 via line 1008. An output from flip-flop 1007 indicates that Seek/Deliver 1100 has not detected a valid inhalation for 97.5 seconds.

Flip-Flop 1007 is a conventional "D", type flip-flop with reset and includes data input terminal D, clock input terminal C, reset terminal R, and output terminals Q and $\overline{Q}$. Flip-flop 1007 is reset at terminal R via line 1009 from terminal 840 of Reset and Power Monitor 800 which terminal goes on when a flow initiation pulse occurs or upon reset conditions described under Reset and Power Monitor 800. Flip-flop 1007 receives 10 kilohertz up pulses from terminal C7 via line 1010.

During the normal reset condition of flip-flop 1007, $\overline{Q}$ is on via line 1011 to AND 1012. The other input to AND 1012 is from terminal S of Seek/Deliver 1100 via line 1013 which goes on if Seek/Deliver 1100 has not detected a flow initiation pulse for 7.5 seconds, the details of which will be described in connection with Seek/Deliver 1100 below. If this abnormal condition occurs AND 1012 goes on via line 1014 to flip-flop 1015.

Flip-flop 1015 is a conventional "S" type flip-flop with set function and includes input set terminal S, reset terminal R, and output terminals Q (terminal $\overline{Q}$ is not shown because it is not used). When terminal S of flip-flop 1015 receives an on signal from AND 1012, terminal Q goes on via line 1016 to serial register 1017.

Counter 1017 is a conventional eight-bit Johnson counter with input clock terminal C, count enable terminal CE which is clamped to ground 6 via line 1018 which continuously enables register 1017, and output terminal $Q_7$ which represents the eighth bit (terminals for bits are not shown because they are not used), and reset terminal R which receives a reset signal from terminal 840 via line 1009 whenever a flow initiation pulse occurs or under the other reset conditions described under Reset and Power Monitor 800.

Upon receiving the first input on signal at terminal C from flip-flop 1015, bit $Q_0$ (not shown) of counter 1017 goes off and bit $Q_1$ goes on, and so forth with each input signal at terminal C to terminal $Q_7$ if no reset signal is received in the interim, that is, if no valid inhalation has been detected to cause a reset at terminal R.

The on/off input signals at terminal C of counter 1017 are generated by flip-flop 1015. After Seek/Deliver 1100 has delivered continuous oxygen for 7.5 seconds, terminal 1128a of Seek/Deliver 1100 comes on via line 1019 to terminal R of flip-flop 1015 to reset flip-flop 1015. This causes terminal Q to go off At this time, Seek/Deliver 1100 is waiting for 7.5 seconds for a valid inhalation to occur. If none occurs at the end of this time, terminal 1123 again goes on, AND 1012 goes on, and terminal Q of flip-flop 1015 again goes on to advance serial register 1017 to bit 2. Thus, one cycle of Seek/Deliver 1100 advanced one bit to the next register 1017 takes 15 seconds. If this cycle continues for a total of 97.5 seconds, bit $Q_7$ goes on via line 1020 to terminal D of flip-flop 1007 which turns on terminal $\overline{Q}$ and turns on terminal Q of flip-flop 1007. When terminal Q of flip-flop 1007 goes on audible alarm 1001 is sounded.

The 97.5 second lapse in detection of the valid inhalation signal is most likely to occur if the patient removes the cannula. The audible alarm sounds as a reminder to turn off the unit and the oxygen flow in order to avoid oxygen waste. This feature can also be used to sound an alarm in the event of patient breathing failure or apneic condition.

Figure 11:
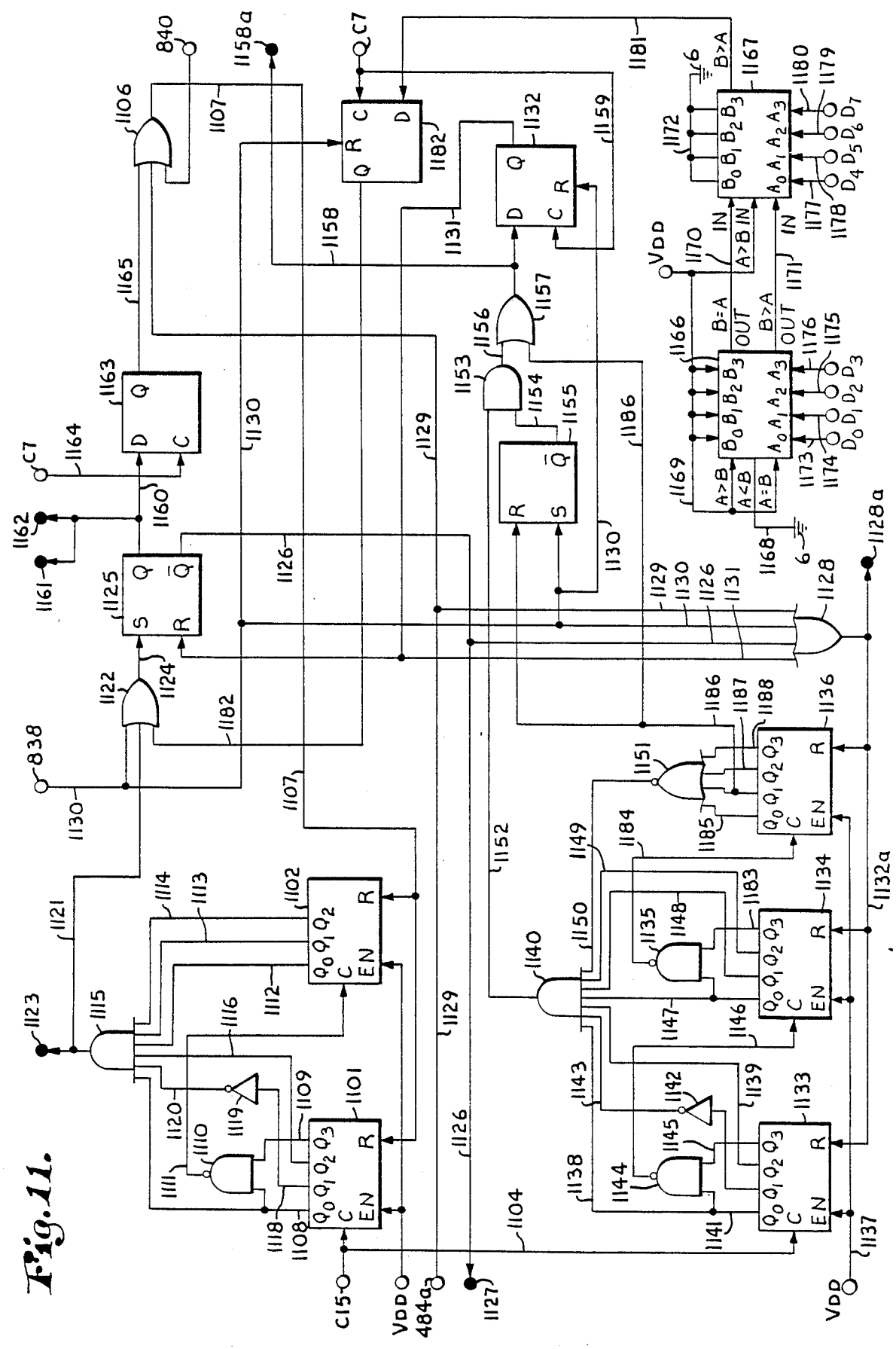
FIG. 11 is an electrical schematic drawing depicting the preferred seek/deliver circuitry.

11. FIG. 11, Seek/Deliver 1100

Seek/Deliver module 1100 monitors patient breath rate and if that breath rate is outside predetermined norms, causes oxygen to be delivered continuously for 7.5 seconds at the end of which time, solenoid 22 is re-energized for 7.5 seconds during which time Seek/Deliver 1100 waits to detect a valid inhalation. If a valid inhalation does not occur during this "seek" time, solenoid valve 22 is again de-energized to "deliver" oxygen again for 7.5 seconds. This cycle continues indefinitely. A breath rate below 8 per minute corresponds to 7.5 second gap between valid inhalation pulses and is detected by use of pulse count timers. Patient breath rate above 53 per minute is detected by use of the count data of Three Breath Timer 500. Additionally, Seek/Deliver 1100 provides a 20 second delay on power up before allowing solenoid valve 22 to be energized to allow the circuitry to warm up and stabilize.

"Seek" timing is provided by pulse counters 1101 and 1102. Counters 1101 and 1102 are conventional four-bit binary counters identical to counters 230, 234, 239, 247 and 254 of clock 203. Each counter includes enable terminals EN which are enabled continuously by clamping them high via line 1103 to voltage source $V_{DD}$, clock terminals C, and reset terminals R. Counter 1101 includes output terminals $Q_0$ (least significant bit), $Q_1$, $Q_2$ and $Q_3$ Counter 1102 includes output terminals $Q_0$ (least significant bit), $Q_1$ and $Q_2$ Terminal C of counter 1101 receives 10 hertz down pulses from terminal C15 via line 1104.

During normal operation, counters 1101 and 1102 receive a reset signal terminal R when a flow initiation pulse occurs at terminal 840 which is transmitted to counters 1101 and 1102 via line 1105, OR 1106 and line 1107. After the flow initiation pulse, counter 1101 begins counting 10 hertz input signals at terminal C. When counter 1101 reaches a count of 9, terminals $Q_0$ and $Q_3$ go on via lines 1108 and 1109 respective to NAND 1110 which then goes off via line 1111 to terminal C of counter 1102. At the very next count on counter 1101 (10the input clock pulse), all bits are reset to zero, AND 1110 goes on and $Q_0$ of counter 1102 goes on which corresponds to a time duration of one second (10 pulses at 10 hertz on counter 1101). In this way, counters 1101, 1102 are effectively combined. After 7.5 seconds, bits $Q_0$ and $Q_2$ of counter 1102 are on and bits $Q_1$ and $Q_3$ are off which together represent 0.5 seconds, and bits $Q_0$, $Q_1$ and $Q_2$ of counter 1102 are on corresponding to 7 seconds. The outputs from terminals of counter 1101 are transmitted via lines 1112, 1113 and 1114 respectively to AND 1115. The on signals from terminals $Q_0$ and $Q_2$ of counter 1101 are transmitted via lines 1108 and 1116 respectively to AND 1115. The off status of $Q_1$ of counter 1101 is conveyed via line 1118 to inverter 1119 which goes on via line 1120 to AND 1115. Thus, at 7.5 seconds without a reset signal on counters 1101 and 102, AND 1115 goes on which output is transmitted via line 1121 to OR 1122 and terminal 1123, which terminal output goes to the 97.5 second timer of audible alarm 1000.

When OR 1122 goes on, its output is transmitted via line 1124 to flip-flop 1125. Flip-flop 1125 is a conventional "S" flip-flop with set and reset and includes input set terminal S, reset terminal R, and output terminals Q and $\overline{Q}$. When the input to terminal S goes on, terminal Q goes on and $\overline{Q}$ goes off. The off output from terminal $\overline{Q}$ is transmitted via line 1126 to output terminal 1127 which off output causes Solenoid Control and Monitor 400 to de-energize solenoid valves 20 and 22 which then causes the system to "deliver" oxygen to the patient.

The off status via line 1126 of terminal of flip-flop 25 is also transmitted to OR 1128 at this point in the cycle, the other three inputs to OR are normally off. OR 1128 receives an input via line 1129 from terminal 484a which is normally off unless Solenoid Control and Monitor 400 detects a solenoid coil abnormality. Input to OR 1128 via line 1130 from terminal 828 of Reset and Power Monitor 800 is normally off unless a reset condition exists. Input to OR 1128 via line 1131 from flip-flop 1132 is off at this point in the Seek/Deliver cycle. Thus, when flip-flop 1125 output at terminal $\overline{Q}$ goes off, the output from OR 1128 goes off via line 1132a to remove the reset signals from deliver counters 1133 and 1134.

Counters 1133 and 1134 are identical to counters 1101 and 1102 and are interconnected in the same way to time out a 7.5 second delay duration (in addition, counter 1134 uses terminal $Q_3$ in combination with NAND 1135 and warm-up counter 1136 for the warm-up cycle which will be explained in more detail below). Counter 1133 receives 10 hertz clock input pulses via line 1104 from terminal C15 at terminal C. Both counters are continuously enabled by clamping them to voltage $V_{DD}$ via line 1137. Both receive the reset input from OR 1128 via line 1132 at terminal R. The output from terminals $Q_0$ and $Q_2$ of counter 1133 are conveyed via lines 1138, 1139 respectively to AND 1140. The output from terminal $Q_1$ of counter 1133 is transmitted via line 1141 to inverter 1142 which output is transmitted via line 1143 to AND 1140. NAND 1144 receives its inputs from terminals $Q_0$ and $Q_3$ of counter 1133 via lines 1138 and 1145 respectively. The output of NAND is transmitted via line 1146 to terminal C of counter 1134. The output from terminals $Q_0$, $Q_1$, $Q_2$ of counter 1134 are transmitted via lines 1147, 1148 and 1149 respectively to AND 1140. The input to AND 1140 via line 1150 from NOR 1151 is normally on except during the warm-up time.

When the output from OR 1128 goes off and removes the reset from counters 1133 and 1134, AND 1140 goes on after 7.5 seconds which output is transmitted via line 1152 to AND 1153.

The other input to AND 1153 is a continuously on output via line 1154 from terminal $\overline{Q}$ of flip-flop 1155 which output comes on after the initial warm-up period and stays on thereafter to continuously enabling AND 1153. The output from AND 1153 is transmitted via line 1156 to OR 1157. The other output to OR 1157 is off after the initial warm-up period. The output from OR 1157 is transmitted via line 1158 to terminal 1158a and to flip-flop 1132, which is a conventional "D" flip-flop including input data terminal D, clock terminal C, reset terminal R and output terminal Q (terminal $\overline{Q}$ is not shown because it is not used). Terminal R receives a reset input from terminal 828 via line 1130 which is normally off except during a reset condition. Terminal C receives 10 kilohertz up clock pulses from terminal C7 via line 1159.

When the input to terminal D of flip-flop 1132 receives the on input signal from OR 1157, the very next clock pulse received at terminal C turns on terminal Q which output is transmitted via line 1131 to reset flip-flop 1125 and to reset counters 1133 and 1134 via OR 1128. When counters 1133 and 1134 are reset, AND 1140 goes off, AND 1153 goes off as does OR 1157. On the next clock pulse received at terminal C of flip-flop 1132 terminal Q goes off to remove the reset signal from flip-flop 1125, and to remove the input on signal to OR 1128 via line 1131. However, as soon as flip-flop 1125 was reset, terminal $\overline{Q}$ of flip-flop 1125 went on via line 1126 which causes the output of OR 1128 to stay on and hold a reset signal on counters 1133 and 1134. Thus, at the end of the 7.5 second delivery time on counters 1133 and 1134, these counters are reset and held in that condition by flip-flop 1125. This marks the end of one deliver and seek cycle.

When flip-flop 1125 was reset by flip-flop 1132, terminal Q of flip-flop 1125 went off which output was transmitted via line 1160 to terminals 1161 and 1162 and flip-flop 1163. Flip-flop 1163 is a conventional "D" type flip-flop including input data terminal D, clock terminal C, and output terminal Q (terminal $\overline{Q}$ is not shown because it is not used). Terminal C receives one kilohertz up clock pulse from terminal C1 via line 1164.

When the input to terminal D of flip-flop 1163 goes off via line 1160, upon the very next clock pulse received at terminal C, terminal Q goes off via line 1165 to OR 1106, which removes the reset signal from counters 1101 and 1102 allows them to begin counting pulses an "seek" a valid inhalation for 7.5 seconds.

When flip-flop 1125 was reset, terminal $\overline{Q}$ went on to terminal 1127 which enabled Solenoid Control and Monitor 400 to again energize solenoid valves 20 and 22.

If during the time that counters 1101 and 1102 are counting pulses, a valid inhalation occurs, then terminal 840 goes on which resets counters 1101 and 1102. Thus, as long as counters 1101 and 1102 get reset before 7.5 seconds, AND 1116 never goes on and the Seek/Deliver cycling is not actuated. The Seek/Deliver cycle described was initiated by a low breath rate which allowed timers 1101 and 1102 to turn on AND 1115 which initiated delivery of oxygen for 7.5 seconds as determined by delivery counters 1133 and 1134.

Oxygen flow for 7.5 seconds is also initiated by a breath rate greater than 53 breaths per minute as determined by count comparators 1166 and 1167. These counter comparators are identical to comparators 669 and 676 of Flow Pulse Circuit 600. Terminal A<B IN of comparator 1166 is clamped to ground 6 via line 1168. Terminals A>B IN and A=B IN are both clamped high via line 1169 to voltage source $V_{DD}$. Terminals $B_0$, $B_1$, $B_2$ and $B_3$ of comparator 1166 are also clamped high by 1169 to voltage source $V_{DD}$ Terminal B=A OUT of comparator 1166 is connected via line 1170 to terminal B=A IN of comparator 1167. Terminal B>A OUT of comparator 1166 is connected via line 1171 to terminal B>A IN of comparator 1167. Terminal A>B IN of comparator 1167 is clamped high via line 1169 to $V_{DD}$, Terminals $B_0$, $B_1$, $B_2$ and $B_3$ of comparator 1167 are clamped to ground 6 by line 1172.

Comparators 1166 receives input data from terminals $D_0$, $D_1$, $D_2$ and $D_3$ of Three Breath Timer 500 via lines 1173, 1174, 1175 and 1176 respectively, to terminals $A_0$, $A_1$, $A_2$ and $A_3$ of comparator 1166 respectively (terminal $A_0$ being the least significant bit). Terminals $D_4$, $D_5$, $D_6$ and $D_7$ of Three Breath Timer 500 are connected via lines 1177, 1178, 1178, 1179 and 1180 respectively to terminals $A_0$, $A_1$, $A_2$ and $A_3$ respectively of comparator 1167 (terminal $A_3$ being the most significant bit).

Because the terminals $B_{0-3}$ of comparator 1166 are clamped high and the terminals $B_{0-3}$ of comparator 1167 are clamped low, a count of decimal 15 is represented in binary. Whenever this count is greater than the input data count received at the $A_{0-3}$ terminals, then the output of comparator 1167 at terminal B>A OUT goes on via line 1181 to flip-flop 1182. A count of decimal 14 or less represented in binary terminals $D_{0-7}$ represents a short interval for Three Breath Timer 500 which corresponds to a frequent breath rate. Thus, whenever Three Breath Timer 500 puts out a three breath count of decimal 14 or less, then the output of comparator 1167 goes on indicating a breath rate higher than the value predetermined at the B terminals of the comparators 1166 and 1167.

The output from comparator 1167 is transmitted via line 1181 to flip-flop 1182 which is a conventional "D" type flip-flop with reset including data input terminal D which receives its input on line 1181, input clock terminal C which receives 10 kilohertz up clock pulses from terminal C7 via line 1159, reset terminal R which is connected via line 1130 to terminal 828, and output terminal Q (terminal $\overline{Q}$ is not shown because it is not used).

If flip-flop 1182 receives an input at terminal D, at the very next clock pulse received at terminal C, Q goes on via line 1182 to OR 1122. An on output from OR 1122 initiates the deliver cycle as described in the paragraphs above. Flip-flop 1182 can only be reset to stop the Seek/Deliver cycle by a reset input at terminal 828 (e.g. by setting BCD to zero flow rate or turning the input of then on again).

The last function performed by Seek/Deliver 100 is to delay energizing of solenoid valves 20 and 22 for 20 seconds when the unit is initially turned on to provide a warm-up time to stabilize the electrical components described herein. When the unit is initially turned on and assuming a non-zero value is selected on the oxygen flow dial, a reset signal exists at terminal 828 for approximately one second until capacitor 818 of Reset and Power Monitor 800 is charged. During the time terminal 828 is on, the flip-flops and counters of Seek/Deliver 1100 are either reset or set with initial value. The on signal at terminal 828 sets flip-flop 1125 on which sets flip-flop 1163 output on, and via OR 1106, a reset signal is held on seek counters 1101 and 1102 even after terminal 828 goes off.

When the on signal at terminal 828 goes off, the output from OR 1128 goes off removing the reset signal from counters 1133, 1134 and 1136, and counter 1133 begins counting input clock pulses received at its terminail C. When terminals $Q_0$ and $Q_3$ of counter 1134 go on after nine seconds, this output is transmitted via lines 1147 and 1183 respectively to NAND 1135, which output goes off via line 1184 to terminal C of warm-up counter 1136 (counter 1136 identical to counters 1133 and 1134). At ten seconds, bits $Q_{0-3}$ are reset to zero and NAND 1135 goes back on.

Terminal EN of counter 1136 is enabled continuously via line 1137 from $V_{DD}$ Counter 1136 receives reset signal at terminal R via line 132 and transmits output from terminals $Q_0$, $Q_1$, $Q_2$ and $Q_3$ via lines 1185, 1186, 1187 and 1188 respectively to NOR 1151. Counter 1136 receives the overflow from counter 1134 and each input pulse to terminal C when NAND 1135 goes on corresponds to a time duration of 10 seconds. When NAND 1135 again goes off and then back on at 20 seconds, terminal $Q_1$ counter 1136 goes on. When this occurs, the output from terminal $Q_1$ is transmitted via line 1186 to terminal R of flip-flop 1155 and OR 1157. When flip-flop 1155 is reset, terminal Q goes on to enable AND 1153 to transmit signals from AND 1140. When OR 1157 receives the input from terminal Q₁ of counter 1136, the output of OR 1157 goes on which causes the output of flip-flop 1132 at terminal Q to go on after 1 clock pulse received at terminal C. When flip-flop 1132 goes on, it resets counters 1133, 1134, 1136 and also flip-flop 1125 which turns on terminal Q on flip-flop 1125 and enables Solenoid Control and Monitor 400 to energize solenoid valves 20 and 22.

Once counter 1136 gets reset, normally it never again receives an input from NAND 1135 while power remains on because the nature of the Seek/Deliver cycle never allows counters 1133 and 1134 to achieve a count greater than that corresponding to 7.5 seconds. Flip-flop 1155, after on receiving an input at terminal R from terminal Q₁ of counter 1136, keeps terminal $\overline{Q}$ continuously energized unless a reset signal is received from terminal 828. Additionally, once counter 1136 is reset, its Q₁ output to OR 1157 remains off also so that only an output from AND 1140 can cause flip-flop 1132 output to go on.

The output of NOR 1151 goes on and stays on when counter 1136 is reset after the warm-up time because the inputs to NOR 1151 via lines 1185, 1186, 1187, and 1188 go off. In the event of some malfunction which allows counter 1134 to count to ten seconds without being reset, then Q₀ of counter 1130 goes on, NOR 1151 goes off, and AND 1140 goes off.

III. Summary of Advantages

As those skilled in the art will appreciate in light of the foregoing detailed description, the apparatus of the present invention provides a number of unique advantages which are not achieved or suggested by the prior art. Chief among these advantages is the fact that the apparatus provides short duration "custom tailored", relatively high flow rate pulses of medicinal gas which vary to meet and accommodate the patient's breathing efforts. By the same token, these "custom tailored" pulses of gas are carefully designed to achieve the physiological equivalent of the usual relatively low flow rate continuous administration of gas. In practice, it has been found that a system in accordance with the invention will save over 50% of the oxygen normally used in conventional continuous flow devices.

By virtue of the fact that the system of the invention tracks and calculates breathing rate and continuously calculates and delivers the medically desire pulse volume during each breath, the invention delivers a preprogrammed volume of gas per unit of time which meets both the physician's prescription and patient's needs. By preprogramming a patient breathing on a continuous cannula this device compensates for the variability of continuous cannula breathing and delivers a known volume over each minute of time.

Another consequence of the structure of the invention resides in the fact that the need for system humidification is largely if not entirely eliminated. This results in a cost saving inasmuch as no humidifier is required, and moreover a propensity of such humidifiers to be a significant vector for transmission of disease to the patient is avoided.

Apart from the normal pulse mode operation of the apparatus, the system of the invention is designed to automatically convert to continuous flow operation in the event of power failure or circuit malfunctions. Hence, in the event of such abnormalities the patient is not deprived of medicinal gas. As an adjunct to this safety feature, appropriate alarms and signal lights are also activated to warn attendants of the malfunction.

Another very significant feature of the invention involves the so-called seek/deliver function. That is to say, if the patient breath rate is abnormally low (e.g., an apneic event) or high, the seek/deliver circuitry forming a part of the invention will deliver the relatively long oxygen pulses on an intermittent basis while in the interim monitoring the patient to ascertain if normal breathing rates have resumed. In the latter instance, the system again automatically reverts to the normal pulse flow operation.

The overall reliability of the apparatus hereof is further enhanced by virtue of the rezeroing function built into the control circuitry. As noted above, in order to achieve the lowest desirable pulse flow operation, it is necessary to use very sensitive pressure or flow sensing equipment. However, with such equipment there is a possibility of ambient-induced signal drift which can lead to improper timing of delivered doses or even possibly skipping of pulses. This potential problem is overcome, however, by virtue of the described rezeroing apparatus.

Finally, the invention has wide applicability in diverse situations where supplemental gas is necessary or desirable. Thus, the specifically disclosed "hospital" and "home" units are but two examples of the scope of the invention. If desired, portable units can be produced in accordance with the invention to be carried by patients or for use with oxygen concentrators; such devices would be within the skill of the art upon appreciation of the concepts of the present invention.

While the specific circuitry herein disclosed or described is designed to be incorporated on one or more semiconductor chips for ease of manufacture, reliability and cost reduction, one skilled in the art will appreciate that the present invention can be embodied using a microprocessor with a program, for example, or alternately with totally pneumatic instrumentation.

In addition, the breathing cycle sensing means and correspondingly coupled measuring means of the invention can at the discretion of the designer be used to measure virtually any parameter or time interval which will characterize a patient's breathing cycle or part thereof. While in one disclosed embodiment herein the patient's breath rate is effectively measured, in other instances the duration of inhalation for example could be measured and used in providing a value. Accordingly, the terminology "breathing cycle sensing means" and "measuring means" as used herein should be taken in a broad sense to encompass all such devices and embodiments which may be employed to derive characterizing information.

We claim:

1. A pulse translation apparatus for translating a series of input signals occurring at variable time intervals into a series of corresponding output signals such that each of the output signals commences in predetermined time relationship to the occurrence of a corresponding input signal and represents a time duration correlated in predetermined manner with the time intervals corresponding to a predetermined plurality if preceding input signals, said apparatus comprising:

input means for receiving said input signals;
output means for delivering said output signals;
a plurality of timer means greater in number than said predetermined plurality of preceding input signals, and each operable for measuring a time interval between events characterizing the occurrence of the first and last signals of said predetermined plurality of preceding input signals, and for generating an output signal representative of a time duration correlated in predetermined manner with said time interval;

means for sequentially coupling each of said timer means with said input means in response to a successive one of said input signals; and means for sequentially decoupling each of said timer means from said input means, and for sequentially coupling each of said timer means with said output means in response to the last signal of said predetermined plurality of input signals.

2. The apparatus as set forth in claim 1, including means for delivering clock signals at regular intervals to each of said timer means, each of said timer means including means for receiving and counting said clock signals for said time interval to produce a total count of said clock signals received during said time interval, said output signals being representative of said total count.

3. The apparatus as set forth in claim 2, said input, output and clock signals being electrical digital signals.

4. The apparatus as set forth in claim 2, said apparatus including four timer means.

5. In an apparatus for delivering medicinal gas to a patient, said apparatus having means for tracking the breathing efforts of the patient and for producing a plurality of breath cycle signals corresponding to a predetermined event in each of a plurality of patient breathing cycles, a method of using said apparatus for determining the breathing rate of the patient comprising the steps of:

(a) starting one of a plurality of timers upon the occurrence of a first one of a plurality of said breath cycle signals;

(b) stopping said one time upon the occurrence of a subsequent breath cycle signal, said subsequent breath cycle signal being at least the second signal after said first signal, (c) producing an output signal representative of the time interval between said first one and said subsequent breathing cycle signals, said output signal being correlated with and representative of the patient's breathing rate, (d) continuously repeating steps (a), (b), and (c) for each of said plurality of timers upon the occurrence of successive breath cycle signals respectively.

6. The method as set forth in claim 5, wherein said first one of said breath cycle signals corresponding to each of said timers are consecutive breath cycle signals.

7. The method as set forth in claim 5, said plurality of timers including at least three timers, said subsequent breathing cycle signal being the sequentially subsequent signal equal to the number of said timers less one.

8. An apparatus for translating a series of input signals occurring at variable time intervals into a series of corresponding output signals wherein the series input signals presents a plurality of sets of input signals with each set having a predetermined plurality of input signals included therein, and in which each output signal is associated with an input signal set and represents the time interval between the first and the last input signals of an associated set, said apparatus comprising:

a plurality of selectively activatable and deactivatable timer means greater in number than said predetermined plurality, each of said timer means including means for producing an output signal representative of the time interval between activation and deactivation thereof; and input means operably coupled with said timer means for receiving the input signals and for activating each timer means in response to the first input signal of the set respectively associated therewith, and for deactivating each timer means in response to the last input signal of the set respectively associated therewith whereby each of said timer means produces a respective output signal representative of the time interval between the first and last input signal of an associated set of input signals and thereby representative of an average of variable time intervals between input signals included in the associated set.

9. The apparatus as set forth in claim 8, the respective first input signals of the sets being sequential input signals and said timer means being one greater in number than said predetermined plurality wherein said timer means produce respective sequential output signals representative of the respective time intervals between the first and last input signals of the respectively associated sets and thereby representative of a moving average of the variable time intervals of the predetermined plurality of input signals.

10. The apparatus as set forth in claim 9, including four of said timer means.

11. The apparatus as set forth in claim 8, said timer means including solid state digital timers.

* * * * *